United States Patent
Ji et al.

(10) Patent No.: US 10,273,246 B2
(45) Date of Patent: Apr. 30, 2019

(54) METHODS AND COMPOSITIONS OF SUBSTITUTED 5H-[1,2,5] OXADIAZOLO [3',4':5,6] PYRAZINO[2,3-B] INDOLE ANALOGS AS INHIBITORS OF β-CATENIN/T-CELL FACTOR PROTEIN-PROTEIN INTERACTIONS

(71) Applicant: University of Utah Research Foundation, Salt Lake City, UT (US)

(72) Inventors: Haitao Ji, Salt Lake City, UT (US); Yongqiang Zhang, Salt Lake City, UT (US); Min Zhang, Salt Lake City, UT (US); Jonathan L. Catrow, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 15/575,253

(22) PCT Filed: May 13, 2016

(86) PCT No.: PCT/US2016/032482
§ 371 (c)(1),
(2) Date: Nov. 17, 2017

(87) PCT Pub. No.: WO2016/187050
PCT Pub. Date: Nov. 24, 2016

(65) Prior Publication Data
US 2018/0134729 A1    May 17, 2018

Related U.S. Application Data

(60) Provisional application No. 62/163,346, filed on May 18, 2015.

(51) Int. Cl.
*C07D 498/14* (2006.01)
*A61P 43/00* (2006.01)
*A61P 35/00* (2006.01)

(52) U.S. Cl.
CPC ............ *C07D 498/14* (2013.01); *A61P 35/00* (2018.01); *A61P 43/00* (2018.01)

(58) Field of Classification Search
CPC .................................................. C07D 498/14
See application file for complete search history.

(56) References Cited

U.S. PATENT DOCUMENTS

| 7,875,613 B2 | 1/2011 | Guedat et al. |
| 8,071,597 B2 | 12/2011 | Gaillard et al. |
| 2011/0245315 A1* | 10/2011 | Chen .................... C07D 209/08 514/415 |

FOREIGN PATENT DOCUMENTS

| WO | WO-2010/014948 A1 | 2/2010 | |
| WO | WO-2013/120045 A1 | 8/2013 | |
| WO | WO-2014/041125 A1 | 3/2014 | |
| WO | WO-2014041125 A1 * | 3/2014 | .......... C07D 311/58 |
| WO | PCT/US2016/032482 | 5/2016 | |

OTHER PUBLICATIONS

M. Zhang et al., 424 Analytical Biochemistry, 57-63 (2012) (Year: 2012).*
V. Korinek et al., 275 Science, 1785-1787 (1997) (Year: 1997).*
A. Klaus et al., 8 Nature Reviews Cancer, 387-398 (2012); H. Clever et al., 149 Cell, 1192-1205 (2012) (Year: 2012).*
M Chilosi et al., 162 American Journal of Pathology, 1495-1502 (2008) (Year: 2008).*
A.P. Lam et al., 23 Current Opinion in Rheumatology, 562-567 (2011) (Year: 2011).*
Y. Guo et al., 61 Physiological Research, 337-346 (2012) (Year: 2012).*
J.L. Catrow et al., 58 Journal of Medicinal Chemistry, 4678-4692 (2015) (Year: 2015).*
H. Clevers et al., 149 Cell, 1192-1205 (2012) (Year: 2012).*
Ashihara, E. et al., β-Catenin Small Interfering RNA Successfully Suppressed Progression of Multiple Myeloma in a Mouse Model. Clin Cancer Res. 2009;15(8):1731-8.
Baell, J. and Walters, M.A., Chemistry: Chemical Con Artists Foil Drug Discovery. Nature. 2014; 513(7519):481-3.
Baell, J.B. and Holloway, G.A., New Substructure Filters for Removal of Pan Assay Interference Compounds (PAINS) from Screening Libraries and for Their Exclusion in Bioassays. J Med Chem. 2010; 53(7):2719-40.
Baell, J.B., Observations on Screening-Based Research and Some Concerning Trends in the Literature. Future Med Chem. 2010; 2(10):1529-46.
Barker, N. et al., Crypt Stem Cells as the Cells-of-Origin of Intestinal Cancer. Nature. 2009; 457(7229):608-11.
Bhat, V.T. et al., Nucleophilic Catalysis of Acylhydrazone Equilibration for Protein-Directed Dynamic Covalent Chemistry. Nat Chem. 2010; 2(6):490-7.
Bunyapaiboonsri, T. et al., Dynamic Deconvolution of a Pre-Equilibrated Dynamic Combinatorial Library of Acetylcholinesterase Inhibitors. ChemBioChem. 2001; 2(6):438-44.
Bunyapaiboonsri, T. et al., Generation of Bis-Cationic Heterocyclic Inhibitors of *Bacillus subtilis* HPr Kinase/Phosphatase from a Ditopic Dynamic Combinatorial Library. J Med Chem. 2003; 46(26):5803-11.
Che, J .et al., Chemical and Biological Properties of Frequent Screening Hits. J Chem Inf Model. 2012; 52(4):913-26.

(Continued)

*Primary Examiner* — Alexander R Pagano
(74) *Attorney, Agent, or Firm* — Ballard Spahr LLP

(57) ABSTRACT

In one aspect, the invention relates to substituted 5H-[1,2, 5]oxadiazolo [3',4':5,6]pyrazino[2,3-b]indole analogs, derivatives thereof, and related compound; synthetic methods for making the compounds; pharmaceutical compositions comprising the compounds; and A methods of treating disorders, e.g., various tumors and cancers, associated with a β-catenin/T-cell factor interaction dysfunction using the compounds and compositions. This abstract is intended as a scanning tool for purposes of searching in the particular art and is not intended to be limiting of the present invention.

21 Claims, 56 Drawing Sheets
Specification includes a Sequence Listing.

(56) References Cited

OTHER PUBLICATIONS

Choi, H.-J. et al., Interactions of Plakoglobin and β-Catenin with Desmosomal Cadherins: Basis of Selective Exclusion of α- and β-Catenin from Desmosomes. J Biol Chem. 2009; 284(46):31776-88.
Choi, H.-J. et al., Thermodynamics of β-Catenin-ligand Interactions: the Roles of the N- and C-terminal Tails in Modulating Binding Affinity. J Biol Chem. 2006; 281(2):1027-38.
Clevers, H. and Nusse, R., Wnt/β-Catenin Signaling and Disease. Cell. 2012; 149(6):1192-205.
Cousins, G.R.L. et al., Dynamic Combinatorial Libraries of Pseudo-Peptide Hydrazone Macrocycles. Chem Commun. 1999; 0:1575-6.
Dahlin, J.L. et al., PAINS in the Assay: Chemical Mechanisms of Assay Interference and Promiscuous Enzymatic Inhibition Observed During a Sulfhydryl-Scavenging HTS. J Med Chem. 2015; 58(5):2091-113.
Dai, R. et al., Inhibition of *Mycobacterium tuberculosis* Transaminase BioA by Aryl Hydrazines and Hydrazides. ChemBioChem. 2014; 15(4):575-86.
Eklof Spink, K. et al., Molecular Mechanisms of β-Catenin Recognition by Adenomatous Polyposis *coli* Revealed by the Structure of an APC-β-Catenin Complex. EMBO J. 2001; 20(22):6203-12.
Freisner, R.A. et al., Glide: A New Approach for Rapid, Accurate Docking and Scoring. 1. Method and Assessment of Docking Accuracy. J Med Chem. 2004; 47(7):1739-49.
Gail, R. et al., Systematic Peptide Array-based Delineation of the Differential β-Catenin Interaction with Tcf4, E-Cadherin, and Adenomatous Polyposis *coli*. J Biol Chem. 2005; 280(8):7107-17.
Gonsalves, F.C. et al., An RNAi-based Chemical Genetic Screen Identifies Three Small-Molecule Inhibitors of the Wnt/wingless Signaling Pathway. Proc Natl Acad Sci USA. 2011; 108(15):5954-63.
Graham, T.A. et al., Crystal Structure of a β-Catenin/Tcf Complex. Cell. 2000; 103(6):885-96.
Graham, T.A. et al., Tcf4 Can Specifically Recognize β-Catenin Using Alternative Conformations. Nat Struct Biol. 2001; 8(12):1048-52.
Grossmann, T.N. et al., Inhibition of Oncogenic Wnt Signaling Through Direct Targeting of β-Catenin. Proc Natl Acad Sci USA. 2012; 109(44)1 7942-7.
Ha, N.-C. et al., Mechanism of Phosphorylation-dependent Binding of APC to β-Catenin and Its Role in β-Catenin Degradation. Mol Cell. 2004; 15(4):511-21.
Halbedl, S. et al., Synthesis of Novel Inhibitors Blocking Wnt Signaling Downstream of β-Catenin. FEBS Lett. 2013; 587(5):522-7.
He, L. et al., Discovering Potent Inhibitors Against the β-Hydroxyacyl-Acyl Carrier Protein Dehydratase (FabZ) of *Helicobacter pylori*: Structure-Based Design, Synthesis, Bioassay, and Crystal Structure Determination. J Med Chem. 2009; 52(8):2465-81.
He, T.-C. et al., Identification of c-MYC as a Target of the APC Pathway. Science. 1998; 281(5382):1509-12.
Helissey, P .e al., Alkylation of 5- and 6-Methylindolo[2,3-b]quinoxalines: Revised Structures of the N,N'-Dimethylated Salts. Eur J Org Chem. 2005; 2005(2)410-5.
Huang, Z. et al., Targeting the Tcf4 $G^{13}$ and $ANDE^{17}$ Binding Site to Selectively Disrupt β-Catenin/T-Cell Factor Protein—Protein Interactions. ACD Chem Biol. 2014; 9(1):193-201.
Huber, A.H. and Weis, W.I., The Structure of the β-Catenin/E-Cadherin Complex and the Molecular Basis of Diverse Ligand Recognition by β-Catenin. Cell. 2001; 105(3):391-402.
Huth, J.R. et al., Toxicological Evaluation of Thiol-Reactive Compounds Identified Using a La Assay to Detect Reactive Molecules by Nuclear Magnetic Resonance. Chem Res Toxicol. 2007; 20(12):1752-9.
Ichikawa, T. et al., New Synthesis of Adenine and 4-Aminoimidazole-5-Carboxamide. J Heterocyclic Chem. 1965; 2:253-5.

Ilyas, M. et al., β-Catenin Mutations in Cell Lines Established from Human Colorectal Cancers. Proc Natl Acad Sci USA. 1997; 94(19):10330-4.
Jadhav, A. et al., Quantitative Analyses of Aggregation, Autofluorescence, and Reactivity Artifacts in a Screen for Inhibitors of a Thiol Protease. J Med Chem. 2010; 53(1):37-51.
Jiang, Q.-Q. et al., Discovery of Potent Inhibitors of Human β-Tryptase from Pre-Equilibrated Dynamic Combinatorial Libraries. Chem Sci. 2015; 6:1792-800.
Kim, J.-S. et al., Proof-of-Principle: Oncogenic β-Catenin is a Valid Molecular Target for the Development of Pharmacological Inhibitors. Mol Cancer Ther. 2002; 1(14):1355-9.
Kim, P.J. et al., Survlvln and Molecular Pathogenesis of Colorectal Cancer. Lancet. 2003; 362(9379):205-9.
Klaus, A. and Birchmeier, W., Wnt Signaling and Its Impact on Development and Cancer. Nat Rev Cancer. 2008; 8(5):387-98.
Knapp, S. et al., Thermodynamics of the High-Affinity Interaction of TCF4 with β-Catenin. J Mol Biol. 2001; 306(5):1179-89.
Korinek, V. et al., Constitutive Transcriptional Activation by a β-Catenin-Tcf Complex in $APC^{-/-}$ Colon Carcinoma. Science. 1997; 275(5307):1784-7.
Lee, E. et al., Inhibition of Androgen Receptor and β-Catenin Activity in Prostate Cancer. Proc Natl Acad Sci USA. 2013; 110(39):15710-5.
Lepourcelet, M. et al., Small-Molecule Antagonists of the Oncogenic Tcf/β-Catenin Protein Complex. Cancer Cell. 2004; 5(1):91-102.
Leung, J.Y. et al., Activation of AXIN2 Expression by β-Catenin-T-cell Factor. A Feedback Repressor Pathway Regulating Wnt Signaling. J Biol Chem. 2002; 277(4):21657-65.
Liu, J. et al., The Third 20 Amino Acid Repeat is the Tightest Binding Site of APC for β-Catenin. J Mol Biol. 2006; 360(1):133-44.
Malanchi, I. et al., Cutaneous Cancer Stem Cell Maintenance is Dependent on β-Cantenin Signalling. Nautre. 2008; 452(7187):650-3.
Malvezzi, A. et al., Uncovering False Positives on a Virtual Screening Search for Cruzain Inhibitors. Bioorg Med Chem Lett. 2008; 18(1):350-4.
Metz, J.T. et al., Enhancement of Chemical Rules for Predicting Compound Reactivity Towards Protein Thiol Groups. J Comput Aided Mol Des. 2007; 21(1-3):139-44.
Mondal, M. et al., Structure-Based Design of Inhibitors of the Aspartic Protease Endothiapepsin by Exploiting Dynamic Combinatorial Chemistry. Angew Chem Int Ed Engl. 2014; 53:3259-63.
Morris, G.M. et al., AutoDock4 and AutoDockTools4: Automated Docking with Selective Receptor Flexibility. J Comput Chem. 2009; 30(16):2785-91.
Mysinger, M.M. et al., Structure-based Ligand Discovery for the Protein—Protein Interface of Chemokine Receptor CXCR4. Proc Natl Acad Sci USE. 2012; 109(14):5517-22.
Narang, R. et al., A Review on Biological Activities and Chemical Synthesis of Hydrazide Derivatives. Curr Med Chem. 2012; 19(4):569-612.
Nikolovska-Coleska, Z. et al., Development and Optimization of a Binding Assay for the XIAP BIR3 Domain Using Fluorescence Polarization. Anal Biochem. 2004; 332(2):261-73.
Okabe, K. et al., Development of Hydrophile Fluorogenic Derivatization Reagents for Thiols: 4-(N-acetylaminosulfonyl)-7-fluoro-2,1,3-benzoxadiazole and 4-(N-trichloroacetylaminosulfonyl)-7-fluoro-2,1,3-benzoxadiazole. J Chromatogr A. 2002; 982(1):111-8.
Orsulic, S. et al., E-Cadherin Binding Prevents β-Catenin Nuclear Localization and β-Catenin/LEF-1-mediated Transactivation. J Cell Sci. 1999; 112(Pt 8):1237-45.
Poulsen, S.-A, Direct Screening of a Dynamic Combinatorial Library Using Mass Spectrometry. J Am Soc Mass Spectrom. 2006; 17:1074-80.
Poy, F. et al., Structure of a Human Tcf4-β-Catenin Complex. Nat Struct Biol. 2001; 8(12):1053-7.
Ramström, O. and Lehn, J.-M., Drug Discovery by Dynamic Combinatorial Libraries. Nat Rev Drug Discov. 2002; 1(1):26-36.

(56) References Cited

OTHER PUBLICATIONS

Řeha, D. et al., Intercalators. 1. Nature of Stacking Interactions Between Intercalators (Ethidium, Daunomycin, Ellipticine, and 4'6-Diaminide-2-phenylindole) and DNA Base Pairs. Ab Initio Quantum Chemical, Density Functional Theory, and Empirical Potential Study. J Am Chem Soc. 2002; 124(13):3366-76.

Reynisson, J. et al., Intercalation of Trioxatriangulenium Ion in DNA: Binding, Electron Transfer, X-ray Crystallography, and Electronic Structure. J Am Chem Soc. 2003; 125(8):2072-83.

Roubínek, F. et al., Substituted 5- and 6-quinoxalinecarboxylic Acids and Their Tuberculostatic Activity. Collect Czech Chem Commun. 1984; 49(1):285-94.

Sampietro, J. et al., Crystal Structure of a β-Catenin/Tcf/Tcf4 Complex. Mol Cell. 2006; 24(2):293-300.

Scholer-Dahirel, A. et al., Maintenance of Adenomatous Polyposis *coli* (APC)-mutant Colorectal Cancer is Dependent on Wnt/β-Catenin Signaling. Proc Natl Acasd Sci USA. 2011; 108(41):17135-40.

Smith, M.C. and Gestwicki, J.E., Features of Protein-Protein Interactions that Translate into Potent Inhibitors: Topology, Surface Area and Affinity. Expert Rev Mol Med. 2012; 14:e16 (24 pages).

Sparks, A.B. et al., Mutational Analysis of the APC/β-Catenin/Tcf Pathway in Colorectal Cancer. Cancer Res. 1998; 58(6):1130-4.

Sun, J. and Wei, W.I., Biochemical and Structural Characterization of β-Catenin Interactions with Non-Phosphorylated and CK2-Phosphorylated Lef-1. J Mol Biol. 2011; 405(2):519-30.

Takabatake, T. et al., Reaction of 4,7-dimethylbenzofurazan with Singlet Oxygen. Tetrahedron Lett. 2001; 42(6):987-9.

Tetsu, O. and McCormick, F., β-Catenin Regulates Expression of Cyclin D1 in Colon Carcinoma Cells. Nature. 1999; 398:422-6.

Thomas, K.R.J. and Tyagi, P., Synthesis, Spectra, and Theoretical Investigations of the Triarylamines Based on 6H-indolo[2,3-b]quinoxaline. J Org Chem. 2010; 75(23):8100-11.

Tian, W. et al., Structure-Based Discovery of a Novel Inhibitor Targeting the β-Catenin/Tcf4 Interaction. Biochemistry. 2012; 51(2):724-31.

Tickenbrock, L. et al., Differences Between the Interactions of β-Catenin with Non-Phosphorylated and Single-mimicked Phosphorylated 20-Amino Acid Residue Repearts of the APC Protein. J Mol Biol. 2003; 327(2):359-67.

Tomašić, T. and Mašic, L.P., Rhodanine as a Privileged Scaffold in Drug Discovery. Curr Med Chem. 2009; 16(13):1596-629.

Trosset, J.-Y. et al., Inhibition of Protein—Protein Interactions: The Discovery of Druglike β-Catenin Inhibitors by Combining Virtual and Biophysical Screening. Proteins. 2006; 64(1):60-7.

Trott, O. and Olson, A.J., AutoDock Vina: Improving the Speed and Accuracy of Docking with a New Scoring Function, Efficient Optimization, and Multithreading. J Comput Chem. 2010; 31(2):455-61.

Von Kries, J.P. et al., Hot Spots in β-Catenin for Interactions with LEF-1, Conductin and APC. Nat Struct Biol. 2000; 7(9):800-7.

Wang, L. et al., X-ray Crystal Structures of the Estrogen-Related Receptor-? Ligand Binding Domain in Three Functional States Reveal the Molecular Basis of Small Molecule Regulation. J Biol Chem. 2006; 281(49):37773-81.

Xing, Y. et al., Crystal Structure of a β-Catenin/Axin Complex Suggests a Mechanism for the β-Catenin Destruction Complex. Genes Dev. 2003; 17(22):2753-64.

Xing, Y. et al., Crystal Structure of a β-Catenin/APC Complex Reveals a Critical Role for APC Phosphorylation in APC Function. Mol Cell. 2004; 15(4):523-33.

Yeung, J. et al., β-Catenin Mediates the Establishment and Drug Resistance of MLL Leukemic Stem Cells. Cancer Cell. 2010; 18(6):606-18.

Yu, B. and Reynisson, J., Bond Stability of the "Undesirable" Heteroatom—Heteroatom Molecular Moieties for High-Throughput Screening Libraries. Eur J Med Chem. 2011; 46(12):5833-7.

Yu, B. et al., Rational Design of Small-Molecule Inhibitors for β-Catenin /T-Cell Factor Protein—Protein Interactions by Bioisotere Replacement. ACS Chem Biol. 2013; 8(3):524-9.

Zhang, L. et al., Structural Basis for Catalytic and Inhibitory Mechanisms of β-Hydroxyacyl-acyl Carrier Protein Dehydratase (FabZ). J Biol Chem. 2008; 283(9):5370-9.

Zhang, M. et al., High-Throughput Selectivity Assays for Small-Molecule Inhibitors of β-Catenin/T-Cell Factor Protein—Protein Interactions. ACS Med Chem Lett. 2013; 4:306-11.

Zhang, M. et al., New Homogeneous High-Throughput Assays for Inhibitors of β-Catenin/Tcf Protein—Protein Interactions. Anal Biochem. 2012; 424(1):57-63.

International Search Report and Written Opinion dated Aug. 25, 2016 by the International Searching Authority for Patent Application No. PCT/US2016/032482, which was filed on May 13, 2016 and published as WO 2016/187050 on Nov. 24, 2016 (Inventor—Ji et al.; Applicant—University of Utah Research Foundation; (8 pages).

International Preliminary Report on Patentability dated Nov. 21, 2017 by the International Searching Authority for Patent Application No. PCT/US2016/032482, which was filed on May 13, 2016 and published as WO 2016/187050 on Nov. 24, 2016 (Inventor—Ji et al.; Applicant—University of Utah Research Foundation) (6 pages).

U.S. Appl. No. 62/163,346, filed May 18, 2015, Haitao Ji (University of Utah Research Foundation).

\* cited by examiner

```
B                          DXθθXΦXXE
  hLef1       13    GDPELCATDEMIPFKDEGD 31
  hTcf3       28    GGDDLGANDELIPFQDEGG 46
  hTcf4        8    GGDDLGANDELISFKDEGE 26   (green)
  hE-Cadherin 820   TDPTAPPYDSLLVFDYEGS 838  (yellow)
  hAPC-R3    1478   RVQVLPDADTLLHFATEST 1496 (cyan)
```

METHODS AND COMPOSITIONS OF SUBSTITUTED 5H-[1,2,5] OXADIAZOLO [3',4':5,6] PYRAZINO[2,3-B] INDOLE ANALOGS AS INHIBITORS OF β-CATENIN/T-CELL FACTOR PROTEIN-PROTEIN INTERACTIONS

CROSS-REFERENCE TO RELATED APPLICATIONS

This Application is a national stage filing under 35 U.S.C. § 371 of International Application No. PCT/US16/32482, filed on May 13, 2016, which claims the benefit of U.S. Provisional Application No. 62/163,346, filed on May 18, 2015, the contents of which are incorporated herein by reference in their entireties.

REFERENCE TO SEQUENCE LISTING

The Sequence Listing submitted Nov. 17, 2017 as a text file named "21101 0309U2_ST25.txt," created on Nov. 17, 2017, and having a size of 2,533 bytes is hereby incorporated by reference pursuant to 37 C.F.R. § 1.52(e)(5).

BACKGROUND

The canonical Wnt/β-catenin pathway is of particular importance in regulating cell proliferation, differentiation, and cell-cell communication. The aberrant activation of Wnt/β-catenin signaling leads to the initiation and progression of many cancers such as colorectal cancers, leukemia, and multiple myeloma. Moreover, Cancer stem cells, which are resistant to conventional chemo- and radiotherapies and especially virulent, are also controlled by the hyperactivation of canonical Wnt signaling. The formation of the β-catenin/Tcf complex in the cell nucleus is the penultimate step of canonical Wnt signaling. The overactivation of canonical Wnt signaling correlates with the formation of this complex. Selective inhibition of the β-catenin/Tcf protein-protein interaction (PPI) represents an appealing therapeutic strategy.

Despite advances in research directed to identifying inhibitors the Wnt signaling pathway generally, and specifically inhibitors of β-catenin/Tcf PPIs, there remains a scarcity of compounds that are both potent, efficacious, and selective inhibitors of β-catenin/Tcf PPIs and also effective in the treatment of cancers and other diseases associated with uncontrolled cellular proliferation, e.g., cancers and fibrotic diseases. These needs and other needs are satisfied by the present invention.

SUMMARY

In accordance with the purpose(s) of the invention, as embodied and broadly described herein, the invention, in one aspect, relates to compounds useful as inhibitors of β-catenin/Tcf PPIs, methods of making same, pharmaceutical compositions comprising same, and methods of treating disorders, e.g., various tumors and cancers, associated with a β-catenin/T-cell factor interaction dysfunction using same.

Disclosed are compound having a structure represented by a formula:

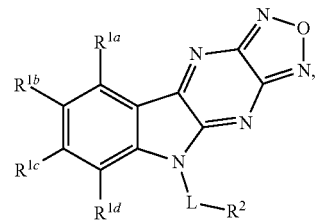

wherein each of $R^{1a}$, $R^{1b}$, $R^{1c}$, and $R^{1d}$ is independently hydrogen, halogen, —CN, C1-C4 alkyl, or C1-C4 haloalkyl; wherein L is $(CH_2)_n$ or a moiety having a structure represented by a formula:

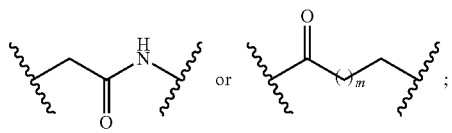

wherein m is an integer with a value of 0 or 1; wherein n is an integer with a value of 0, 1, 2, 3, or 4; and wherein $R^2$ is —CN or a moiety having a structure represented by a formula:

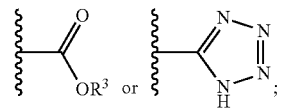

wherein $R^3$ is hydrogen or C1-C4 alkyl; or a pharmaceutically acceptable salt thereof.

Also disclosed are pharmaceutical compositions comprising a therapeutically effective amount of a disclosed compound, or a pharmaceutically acceptable salt thereof, and a pharmaceutically acceptable carrier.

Also disclosed are methods for the treatment of a disorder of uncontrolled cellular proliferation associated with a β-catenin/Tcf dysfunction in a mammal comprising the step of administering to the mammal an effective amount of at least one disclosed compound, or a pharmaceutically acceptable salt thereof.

Also disclosed are methods for inhibiting protein-protein interactions of β-catenin and Tcf in a mammal comprising the step of administering to the mammal a therapeutically effective amount of at least one disclosed compound, or a pharmaceutically acceptable salt thereof.

Also disclosed are methods for inhibiting protein-protein interactions of β-catenin and Tcf in at least one cell, comprising the step of contacting the at least one cell with an effective amount of at least one disclosed compound, or a pharmaceutically acceptable salt thereof.

Also disclosed are uses of at least one disclosed compound for inhibiting β-catenin/Tcf activity.

Also disclosed are uses of at least one disclosed compound for administration to a subject; wherein the subject has a disorder of uncontrolled cellular proliferation.

Also disclosed are kits comprising at least one disclosed compound, or a pharmaceutically acceptable salt thereof; and one or more of:

(a) at least one agent known to increase Tcf activity;
(b) at least one agent known to increase β-catenin activity;

(c) at least one agent known to decrease Tcf activity;
(d) at least one agent known to decrease β-catenin activity;
(e) at least one agent known to treat a disease of uncontrolled cellular proliferation;
(f) instructions for treating a disorder associated uncontrolled cellular proliferation; or
(g) instructions for treating a disorder associated with a β-catenin/Tcf dysfunction.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figures 1A, 1B:
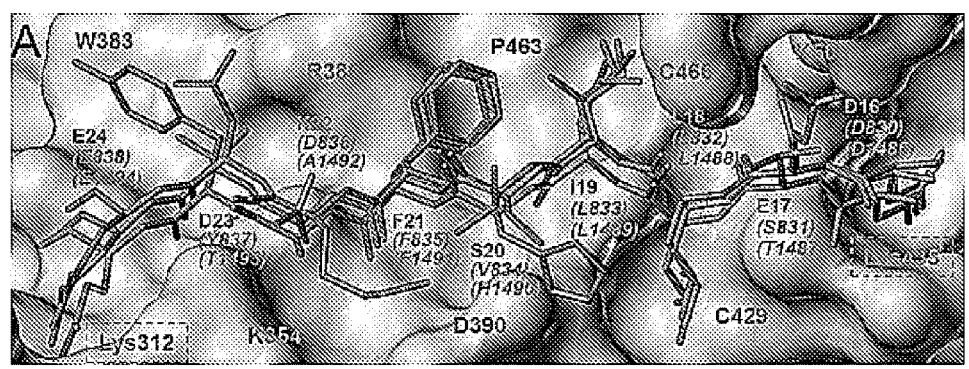
FIG. 1A shows a representative model of the charge-button-recognition region of β-catenin and its interaction with Tcf4 (PDB id, 2GL7), E-Cadherin (PDB id, 1I7W), and APC-R3 (PDB id, 1TH1).
FIG. 1B shows a sequence alignment of human Lef1 (Q9UJU2), human Tcf3 (Q9HCS4), human Tcf4 (Q9NQB0), human E-cadherin (P12830), and human APC-R3 (P25054) that bind with the charge-button-recognition region (underscored). θ and Φ are the hydrophobic and aromatic residues, respectively.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $—(CH_2)_a—$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1-OA^2$ or $—OA^1-(OA^2)_aOA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1$C(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2$O$A^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1$S(O)$_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1$S(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

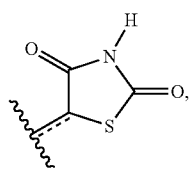

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$ respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

It is also appreciated that certain compounds described herein can be present as an equilibrium mixture of tautomers. For example, ketones with an α-hydrogen can exist in an equilibrium mixture of the keto form and the enol form.

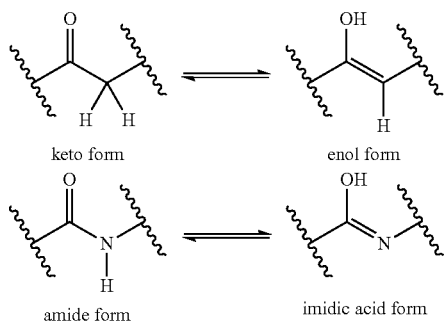

keto form           enol form amide form           imidic acid form

Likewise, amides with an N-hydrogen can exist in an equilibrium mixture of the amide form and the imidic acid form. As another example, tetrazoles can exist in two tautomeric forms, $N^1$-unsubstituted and $N^2$-unsubstituted, as shown below.

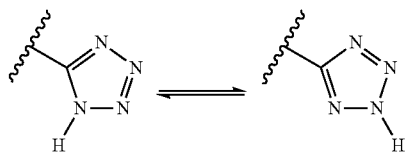 [SMILES: *c1nnn[nH]1 ; *c1nn[nH]n1]

Unless stated to the contrary, the invention includes all such possible tautomers.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

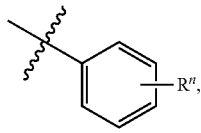

which is understood to be equivalent to a formula:

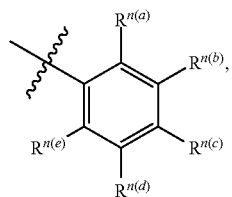

wherein n is typically an integer. That is, $R^n$ is understood to represent five independent substituents, $R^{n(a)}$, $R^{n(b)}$, $R^{n(c)}$, $R^{n(d)}$, $R^{n\ (e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful as inhibitors of β-catenin/Tcf protein-protein interactions, and thus down-regulating Wnt signaling. In a further aspect, the compound selectively inhibits β-catenin/Tcf interactions compared to β-catenin/cadherin interactions. In a still further aspect, the compound inhibits Wnt signaling. In yet a further aspect, the compound inhibits transcription of at least one β-catenin target gene.

In a further aspect, the compound inhibits cell viability. In a still further aspect, the compound inhibits cell migration. In yet a further aspect, the compound inhibits angiogenesis. In an even further aspect, the compound inhibits tumor metastasis. In a still further aspect, the compound inhibits tumor progression.

In a further aspect, the compound exhibits inhibition with an Ki of less than about $1.0 \times 10^{-4}$ M when determined in competitive inhibition assay. In a still further aspect, the compound exhibits inhibition with an Ki of less than about $7.0 \times 10^{-5}$ M when determined in competitive inhibition assay. In yet a further aspect, the compound exhibits inhibition with an Ki of less than about $5.0 \times 10^{-5}$ M when determined in competitive inhibition assay. In an even further aspect, the compound exhibits inhibition with an Ki of less than about $2.5 \times 10^{-5}$ M when determined in competitive inhibition assay. In a still further aspect, the compound exhibits inhibition with an Ki of less than about $1.0 \times 10^{-5}$ M when determined in competitive inhibition assay. In yet a further aspect, the compound exhibits inhibition with an Ki of less than about $7.5 \times 10^{-6}$ M when determined in competitive inhibition assay. In a still further aspect, the compound exhibits inhibition with an Ki of less than about $5.0 \times 10^{-6}$ M when determined in competitive inhibition assay. In a yet further aspect, the compound exhibits inhibition with an Ki of less than about $2.5 \times 10^{-6}$ M when determined in competitive inhibition assay. In yet a further aspect, the compound exhibits inhibition with an Ki of less than about $1.0 \times 10^{-6}$ M when determined in competitive inhibition assay.

In one aspect, the compounds of the invention are useful in the treatment of disorders, e.g., various tumors and cancers, associated with a β-catenin/Tcf protein-protein interaction dysfunction or a Wnt pathway dysregulation using same, and other diseases in which β-catenin/Tcf or the Wnt signaling pathway are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

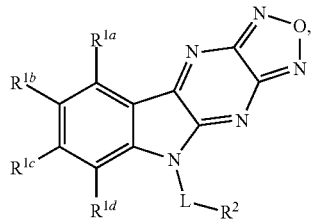

each of $R^{1a}$, $R^{1b}$, $R^{1c}$, and $R^{1d}$ is independently hydrogen, halogen, —CN, C1-C4 alkyl, or C1-C4 haloalkyl; L is $(CH_2)_n$ or a moiety having a structure represented by a formula:

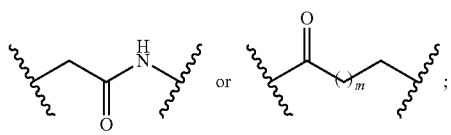 [SMILES: *CC(=O)N* ; *CCC(*)=O]

m is an integer with a value of 0 or 1; n is an integer with a value of 0, 1, 2, 3, or 4; and $R^2$ is —CN or a moiety having a structure represented by a formula:

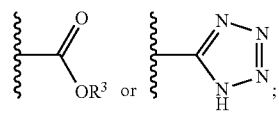

$R^3$ is hydrogen or C1-C4 alkyl; or a pharmaceutically acceptable salt thereof.

In a further aspect, the compound has a structure represented by a formula:

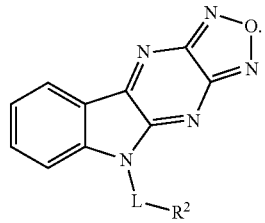

In a further aspect, the compound has a structure represented by a formula:

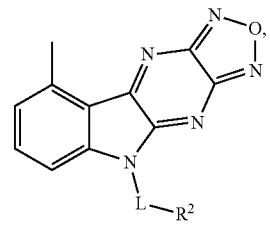

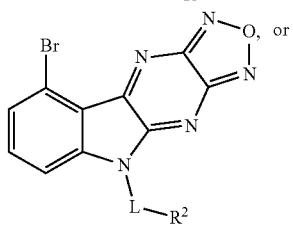

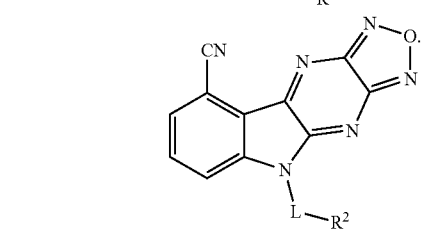

In a further aspect, the compound has a structure represented by a formula:

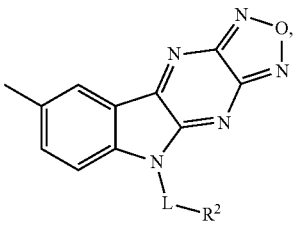

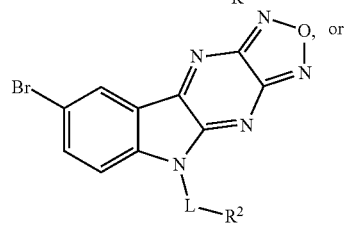

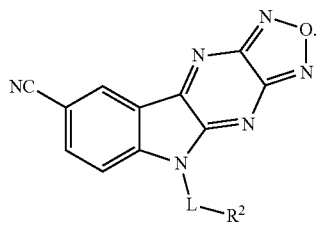
In a further aspect, the compound has a structure represented by a formula:
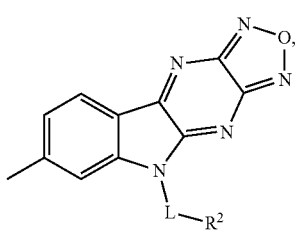
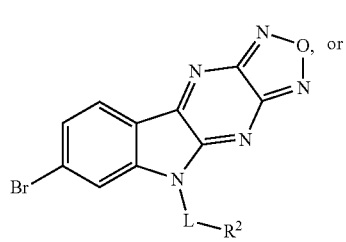
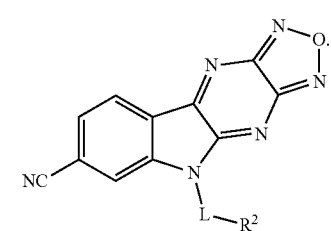
In a further aspect, the compound has a structure represented by a formula:
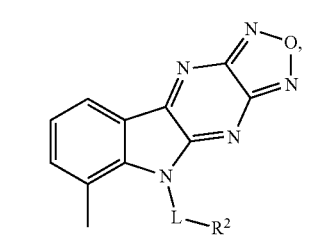
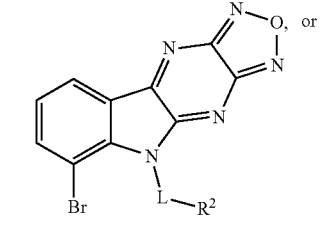
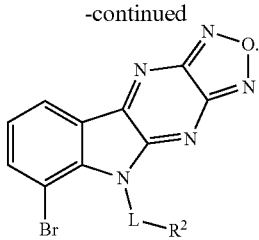
In a further aspect, the compound has a structure represented by a formula:
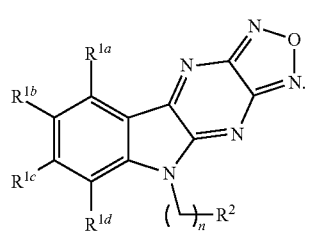
In a further aspect, the compound has a structure represented by a formula:
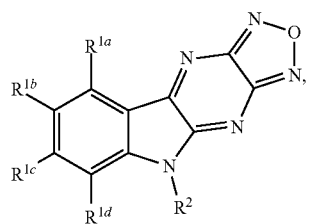
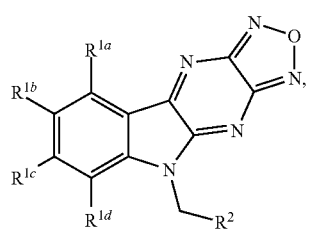
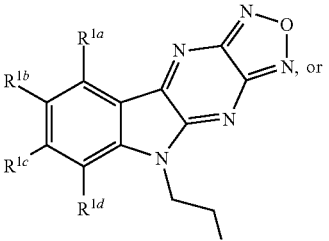
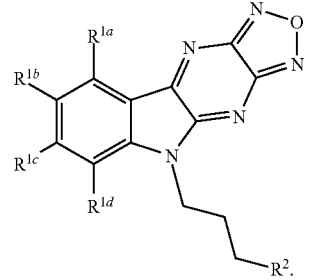

In a further aspect, the compound has a structure represented by a formula:

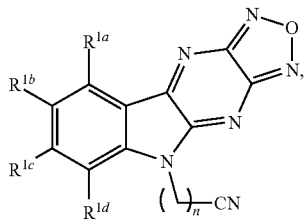

n is an integer selected from 1, 2, 3, and 4.

In a further aspect, the compound has a structure represented by a formula:

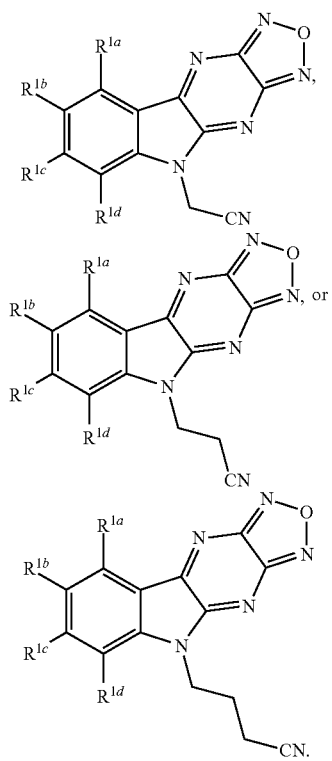

In a further aspect, the compound has a structure represented by a formula:

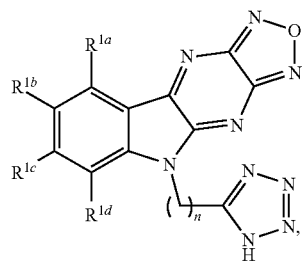

n is an integer selected from 1, 2, 3, and 4.

In a further aspect, the compound has a structure represented by a formula:

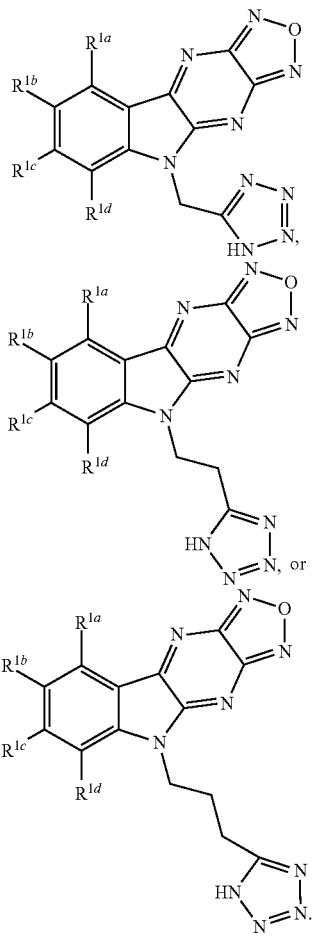

In a further aspect, m is an integer with a value of 0 or 1. In a still further aspect, m is an integer with a value of 0. In a yet further aspect, m is an integer with a value of 1.

In a further aspect, n is an integer with a value of 0, 1, 2, 3, or 4. In a still further aspect, n is an integer with a value of 0, 1, 2, or 3. In a yet further aspect, n is an integer with a value of 0, 1, or 2. In an even further aspect, n is an integer with a value of 0 or 1. In a still further aspect, n is an integer with a value of 0. In a yet further aspect, n is an integer with a value of 1. In an even further aspect, n is an integer with a value of 2. In a still further aspect, n is an integer with a value of 3. In a yet further aspect, n is an integer with a value of 4.

a. $R^{1A}$, $R^{1B}$, $R^{1C}$, and $R^{1D}$ Groups

In various aspects, each of $R^{1a}$, $R^{1b}$, $R^{1c}$, and $R^{1d}$ is independently hydrogen, halogen, —CN, C1-C4 alkyl, or C1-C4 haloalkyl. In a further aspect, each of $R^{1a}$, $R^{1b}$, $R^{1c}$, and $R^{1d}$ is hydrogen.

In a further aspect, each of $R^{1a}$, $R^{1b}$, $R^{1c}$, and $R^{1d}$ is independently hydrogen, halogen, —CN, methyl, ethyl, propyl, isopropyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, or —(CH$_2$)$_2$CI$_3$.

In a further aspect, each of $R^{1a}$, $R^{1b}$, $R^{1c}$, and $R^{1d}$ is independently hydrogen, halogen, —CN, methyl, ethyl, propyl, isopropyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, or —(CH$_2$)$_2$CBr$_3$. In a still further aspect, each of $R^{1a}$, $R^{1b}$, $R^{1c}$, and $R^{1d}$ is independently hydrogen, halogen, —CN, methyl, ethyl, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, or —CH$_2$CBr$_3$. In a yet further aspect, each of $R^{1a}$, $R^{1b}$, $R^{1c}$, and $R^{1d}$ is independently hydrogen, halogen, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In an even further aspect, each of $R^{1a}$, $R^{1b}$, $R^{1c}$, and $R^{1d}$ is independently hydrogen, —F, —Cl, —Br, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$.

In a further aspect, each of $R^{1a}$, $R^{1b}$, and $R^{1c}$ is hydrogen; and $R^{1d}$ is hydrogen, halogen, —CN, methyl, ethyl, propyl, isopropyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, or —(CH$_2$)$_2$CI$_3$.

In a further aspect, each of $R^{1a}$, $R^{1b}$, and $R^{1c}$ is hydrogen; and $R^{1d}$ is hydrogen, halogen, —CN, methyl, ethyl, propyl, isopropyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, or —(CH$_2$)$_2$CBr$_3$. In a still further aspect, each of $R^{1a}$, $R^{1b}$, and $R^{1c}$ is hydrogen; and $R^{1d}$ is hydrogen, halogen, —CN, methyl, ethyl, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, or —CH$_2$CBr$_3$. In a yet further aspect, each of $R^{1a}$, $R^{1b}$, and $R^{1c}$ is hydrogen; and $R^{1d}$ is hydrogen, halogen, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In an even further aspect, each of $R^{1a}$, $R^{1b}$, and $R^{1c}$ is hydrogen; and $R^{1d}$ is hydrogen, —F, —Cl, —Br, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$.

In a further aspect, each of $R^{1a}$, $R^{1b}$, and $R^{1d}$ is hydrogen; and $R^{1c}$ is hydrogen, halogen, —CN, methyl, ethyl, propyl, isopropyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, or —(CH$_2$)$_2$CI$_3$.

In a further aspect, each of $R^{1a}$, $R^{1b}$, and $R^{1d}$ is hydrogen; and $R^{1c}$ is hydrogen, halogen, —CN, methyl, ethyl, propyl, isopropyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, or —(CH$_2$)$_2$CBr$_3$. In a still further aspect, each of $R^{1a}$, $R^{1b}$, and $R^{1d}$ is hydrogen; and $R^{1c}$ is hydrogen, halogen, —CN, methyl, ethyl, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, or —CH$_2$CBr$_3$. In a yet further aspect, each of $R^{1a}$, $R^{1b}$, and $R^{1d}$ is hydrogen; and $R^{1c}$ is hydrogen, halogen, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In an even further aspect, each of $R^{1a}$, $R^{1b}$, and $R^{1d}$ is hydrogen; and $R^{1c}$ is hydrogen, —F, —Cl, —Br, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$.

In a further aspect, each of $R^{1a}$, $R^{1c}$, and $R^{1d}$ is hydrogen; and $R^{1b}$ is hydrogen, halogen, —CN, methyl, ethyl, propyl, isopropyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, or —(CH$_2$)$_2$CI$_3$.

In a further aspect, each of $R^{1a}$, $R^{1c}$, and $R^{1d}$ is hydrogen; and $R^{1b}$ is hydrogen, halogen, —CN, methyl, ethyl, propyl, isopropyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, or —(CH$_2$)$_2$CBr$_3$. In a still further aspect, each of $R^{1a}$, $R^{1c}$, and $R^{1d}$ is hydrogen; and $R^{1b}$ is hydrogen, halogen, —CN, methyl, ethyl, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, or —CH$_2$CBr$_3$. In a yet further aspect, each of $R^{1a}$, $R^{1c}$, and $R^{1d}$ is hydrogen; and $R^{1b}$ is hydrogen, halogen, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In an even further aspect, each of $R^{1a}$, $R^{1c}$, and $R^{1d}$ is hydrogen; and $R^{1b}$ is hydrogen, —F, —Cl, —Br, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$.

In a further aspect, each of $R^{1b}$, $R^{1c}$, and $R^{1d}$ is hydrogen; and $R^{1a}$ is hydrogen, halogen, —CN, methyl, ethyl, propyl, isopropyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, or —(CH$_2$)$_2$CI$_3$.

In a further aspect, each of $R^{1b}$, $R^{1c}$, and $R^{1d}$ is hydrogen; and $R^{1a}$ is hydrogen, halogen, —CN, methyl, ethyl, propyl, isopropyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, or —(CH$_2$)$_2$CBr$_3$. In a still further aspect, each of $R^{1b}$, $R^{1c}$, and $R^{1d}$ is hydrogen; and $R^{1a}$ is hydrogen, halogen, —CN, methyl, ethyl, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, or —CH$_2$CBr$_3$. In a yet further aspect, each of $R^{1b}$, $R^{1c}$, and $R^{1d}$ is hydrogen; and $R^{1a}$ is hydrogen, halogen, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In an even further aspect, each of $R^{1b}$, $R^{1c}$, and $R^{1d}$ is hydrogen; and $R^{1a}$ is hydrogen, —F, —Cl, —Br, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$.

In a further aspect, each of $R^{1a}$, $R^{1b}$, and $R^{1c}$ is hydrogen; and $R^{1d}$ is halogen, —CN, methyl, ethyl, propyl, isopropyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, or —(CH$_2$)$_2$CI$_3$.

In a further aspect, each of $R^{1a}$, $R^{1b}$, and $R^{1c}$ is hydrogen; and $R^{1d}$ is halogen, —CN, methyl, ethyl, propyl, isopropyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, or —(CH$_2$)$_2$CBr$_3$. In a still further aspect, each of $R^{1a}$, $R^{1b}$, and $R^{1c}$ is hydrogen; and $R^{1d}$ is halogen, —CN, methyl, ethyl, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, or —CH$_2$CBr$_3$. In a yet further aspect, each of $R^{1a}$, $R^{1b}$, and $R^{1c}$ is hydrogen; and $R^{1d}$ is halogen, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In an even further aspect, each of $R^{1a}$, $R^{1b}$, and $R^{1c}$ is hydrogen; and $R^{1d}$ is —F, —Cl, —Br, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In a still further aspect, each of $R^{1a}$, $R^{1b}$, and $R^{1c}$ is hydrogen; and $R^{1d}$ is —Br or methyl.

In a further aspect, each of $R^{1a}$, $R^{1b}$, and $R^{1d}$ is hydrogen; and $R^{1c}$ is halogen, —CN, methyl, ethyl, propyl, isopropyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, or —(CH$_2$)$_2$CI$_3$.

In a further aspect, each of $R^{1a}$, $R^{1b}$, and $R^{1d}$ is hydrogen; and $R^{1c}$ is halogen, —CN, methyl, ethyl, propyl, isopropyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, or —(CH$_2$)$_2$CBr$_3$. In a still further aspect, each of $R^{1a}$, $R^{1b}$, and $R^{1d}$ is hydrogen; and $R^{1c}$ is halogen, —CN, methyl, ethyl, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, or —CH$_2$CBr$_3$. In a yet further aspect, each of $R^{1a}$, $R^{1b}$, and $R^{1d}$ is hydrogen; and $R^{1c}$ is halogen, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In an even further aspect, each of $R^{1a}$, $R^{1b}$, and $R^{1d}$ is hydrogen; and $R^{1c}$ is —F, —Cl, —Br, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In a still further aspect, each of $R^{1a}$, $R^{1b}$, and $R^{1d}$ is hydrogen; and $R^{1c}$ is —Br or methyl.

In a further aspect, each of $R^{1a}$, $R^{1c}$, and $R^{1d}$ is hydrogen; and $R^{1b}$ is halogen, —CN, methyl, ethyl, propyl, isopropyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, or —(CH$_2$)$_2$CI$_3$.

In a further aspect, each of $R^{1a}$, $R^{1c}$, and $R^{1d}$ is hydrogen; and $R^{1b}$ is halogen, —CN, methyl, ethyl, propyl, isopropyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, or —(CH$_2$)$_2$CBr$_3$.

In a further aspect, each of $R^{1a}$, $R^{1c}$, and $R^{1d}$ is hydrogen; and $R^{1b}$ is halogen, —CN, methyl, ethyl, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, or —CH$_2$CBr$_3$. In a still further aspect, each of $R^{1a}$, $R^{1c}$, and $R^{1d}$ is hydrogen; and $R^{1b}$ is halogen, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In a yet further aspect, each of $R^{1a}$, $R^{1c}$, and $R^{1d}$ is hydrogen; and $R^{1b}$ is —F, —Cl, —Br, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In an even further aspect, each of $R^{1a}$, $R^{1c}$, and $R^{1d}$ is hydrogen; and $R^{1b}$ is —Br or methyl.

In a further aspect, each of $R^{1b}$, $R^{1c}$, and $R^{1d}$ is hydrogen; and $R^{1a}$ is halogen, —CN, methyl, ethyl, propyl, isopropyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, or —(CH$_2$)$_2$CI$_3$.

In a further aspect, each of $R^{1b}$, $R^{1c}$, and $R^{1d}$ is hydrogen; and $R^{1a}$ is halogen, —CN, methyl, ethyl, propyl, isopropyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, or —(CH$_2$)$_2$CBr$_3$. In a still further aspect, each of $R^{1b}$, $R^{1c}$, and $R^{1d}$ is hydrogen; and $R^{1a}$ is halogen, —CN, methyl, ethyl, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, or —CH$_2$CBr$_3$. In a yet further aspect, each of $R^{1b}$, $R^{1c}$, and $R^{1d}$ is hydrogen; and $R^{1a}$ is halogen, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In an even further aspect, each of $R^{1b}$, $R^{1c}$, and $R^{1d}$ is hydrogen; and $R^{1a}$ is —F, —Cl, —Br, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$. In a still further aspect, each of $R^{1b}$, $R^{1c}$, and $R^{1d}$ is hydrogen; and $R^{1a}$ is —Br or methyl.

In a further aspect, each of $R^{1a}$, $R^{1b}$, $R^{1c}$, and $R^{1d}$ is independently hydrogen, halogen, —CN, or C1-C4 alkyl. In a still further aspect, each of $R^{1a}$, $R^{1b}$, $R^{1c}$, and $R^{1d}$ is independently hydrogen, —F, —Cl, —Br, —CN, methyl, ethyl, propyl, or isopropyl. In a yet further aspect, each of $R^{1a}$, $R^{1b}$, $R^{1c}$, and $R^{1d}$ is independently hydrogen, —F, —Cl, —Br, —CN, or methyl.

In a further aspect, each of $R^{1a}$, $R^{1b}$, and $R^{1c}$ is hydrogen; and $R^{1d}$ is hydrogen, halogen, —CN, or C1-C4 alkyl. In a still further aspect, each of $R^{1a}$, $R^{1b}$, and $R^{1c}$ is hydrogen; and $R^{1d}$ is hydrogen, —F, —Cl, —Br, —CN, methyl, ethyl, propyl, or isopropyl. In a yet further aspect, each of $R^{1a}$, $R^{1b}$, and $R^{1c}$ is hydrogen; and $R^{1d}$ is hydrogen, —F, —Cl, —Br, —CN, or methyl.

In a further aspect, each of $R^{1a}$, $R^{1b}$, and $R^{1d}$ is hydrogen; and $R^{1c}$ is hydrogen, halogen, —CN, or C1-C4 alkyl. In a still further aspect, each of $R^{1a}$, $R^{1b}$, and $R^{1d}$ is hydrogen; and $R^{1c}$ is —F, —Cl, —Br, —CN, methyl, ethyl, propyl, or isopropyl. In a yet further aspect, each of $R^{1a}$, $R^{1b}$, and $R^{1d}$ is hydrogen; and $R^{1c}$ is hydrogen, —F, —Cl, —Br, —CN, or methyl.

In a further aspect, each of $R^{1a}$, $R^{1c}$, and $R^{1d}$ is hydrogen; and $R^{1b}$ is hydrogen, halogen, —CN, or C1-C4 alkyl. In a still further aspect, each of $R^{1a}$, $R^{1c}$, and $R^{1d}$ is hydrogen; and $R^{1b}$ is hydrogen, —F, —Cl, —Br, —CN, methyl, ethyl, propyl, or isopropyl. In a yet further aspect, each of $R^{1a}$, $R^{1c}$, and $R^{1d}$ is hydrogen; and $R^{1b}$ is hydrogen, —F, —Cl, —Br, —CN, or methyl.

In a further aspect, each of $R^{1b}$, $R^{1c}$, and $R^{1d}$ is hydrogen; and $R^{1a}$ is hydrogen, halogen, —CN, or C1-C4 alkyl. In a still further aspect, each of $R^{1b}$, $R^{1c}$, and $R^{1d}$ is hydrogen; and $R^{1a}$ is hydrogen, —F, —Cl, —Br, —CN, methyl, ethyl, propyl, or isopropyl. In a yet further aspect, each of $R^{1b}$, $R^{1c}$, and $R^{1d}$ is hydrogen; and $R^{1a}$ is hydrogen, —F, —Cl, —Br, —CN, or methyl.

In a further aspect, each of $R^{1a}$, $R^{1b}$, and $R^{1c}$ is hydrogen; and $R^{1d}$ is halogen, —CN, or C1-C4 alkyl. In a still further aspect, each of $R^{1a}$, $R^{1b}$, and $R^{1c}$ is hydrogen; and $R^{1d}$ is —F, —Cl, —Br, —CN, methyl, ethyl, propyl, or isopropyl. In a yet further aspect, each of $R^{1a}$, $R^{1b}$, and $R^{1c}$ is hydrogen; and $R^{1d}$ is —F, —Cl, —Br, —CN, or methyl. In an even further aspect, each of $R^{1a}$, $R^{1b}$, and $R^{1c}$ is hydrogen; and $R^{1d}$ is —CN. In a still further aspect, each of $R^{1a}$, $R^{1b}$, and $R^{1c}$ is hydrogen; and $R^{1d}$ is methyl.

In a further aspect, each of $R^{1a}$, $R^{1b}$, and $R^{1c}$ is hydrogen; and $R^{1d}$ is halogen. In a still further aspect, each of $R^{1a}$, $R^{1b}$, and $R^{1c}$ is hydrogen; and $R^{1d}$ is —F. In a yet further aspect, each of $R^{1a}$, $R^{1b}$, and $R^{1c}$ is hydrogen; and $R^{1d}$ is —Cl. In an even further aspect, each of $R^{1a}$, $R^{1b}$, and $R^{1c}$ is hydrogen; and $R^{1d}$ is halogen each of $R^{1a}$, $R^{1b}$, and $R^{1c}$ is hydrogen; and $R^{1d}$ is —Br.

In a further aspect, each of $R^{1a}$, $R^{1b}$, and $R^{1d}$ is hydrogen; and $R^{1c}$ is halogen, —CN, or C1-C4 alkyl. In a still further aspect, each of $R^{1a}$, $R^{1b}$, and $R^{1d}$ is hydrogen; and $R^{1c}$ is —F, —Cl, —Br, —CN, methyl, ethyl, propyl, or isopropyl. In a yet further aspect, each of $R^{1a}$, $R^{1b}$, and $R^{1d}$ is hydrogen; and $R^{1c}$ is —F, —Cl, —Br, —CN, or methyl. In an even further aspect, each of $R^{1a}$, $R^{1b}$, and $R^{1d}$ is hydrogen; and $R^{1c}$ is —CN. In a still further aspect, each of $R^{1a}$, $R^{1b}$, and $R^{1d}$ is hydrogen; and $R^{1c}$ is methyl.

In a further aspect, each of $R^{1a}$, $R^{1b}$, and $R^{1d}$ is hydrogen; and $R^{1c}$ is halogen. In a still further aspect, each of $R^{1a}$, $R^{1b}$, and $R^{1d}$ is hydrogen; and $R^{1c}$ is —F. In a yet further aspect, each of $R^{1a}$, $R^{1b}$, and $R^{1d}$ is hydrogen; and $R^{1c}$ is —Cl. In an even further aspect, each of $R^{1a}$, $R^{1b}$, and $R^{1d}$ is hydrogen; and $R^{1c}$ is —Br.

In a further aspect, each of $R^{1a}$, $R^{1c}$, and $R^{1d}$ is hydrogen; and $R^{1b}$ is halogen, —CN, or C1-C4 alkyl. In a still further aspect, each of $R^{1a}$, $R^{1c}$, and $R^{1d}$ is hydrogen; and $R^{1b}$ is —F, —Cl, —Br, —CN, methyl, ethyl, propyl, or isopropyl. In a yet further aspect, each of $R^{1a}$, $R^{1c}$, and $R^{1d}$ is hydrogen; and $R^{1b}$ is —F, —Cl, —Br, —CN, or methyl. In an even further aspect, each of $R^{1a}$, $R^{1c}$, and $R^{1d}$ is hydrogen; and $R^{1b}$ is —CN. In a still further aspect, each of $R^{1a}$, $R^{1c}$, and $R^{1d}$ is hydrogen; and $R^{1b}$ is methyl.

In a further aspect, each of $R^{1a}$, $R^{1c}$, and $R^{1d}$ is hydrogen; and $R^{1b}$ is halogen. In a still further aspect, each of $R^{1a}$, $R^{1c}$, and $R^{1d}$ is hydrogen; and $R^{1b}$ is —F. In a yet further aspect, each of $R^{1a}$, $R^{1c}$, and $R^{1d}$ is hydrogen; and $R^{1b}$ is —Cl. In an even further aspect, each of $R^{1a}$, $R^{1c}$, and $R^{1d}$ is hydrogen; and $R^{1b}$ is —Br.

In a further aspect, each of $R^{1b}$, $R^{1c}$, and $R^{1d}$ is hydrogen; and $R^{1a}$ is halogen, —CN, or C1-C4 alkyl. In a still further aspect, each of $R^{1b}$, $R^{1c}$, and $R^{1d}$ is hydrogen; and $R^{1a}$ is —F, —Cl, —Br, —CN, methyl, ethyl, propyl, or isopropyl. In a yet further aspect, each of $R^{1b}$, $R^{1c}$, and $R^{1d}$ is hydrogen; and $R^{1a}$ is —F, —Cl, —Br, —CN, or methyl. In an even further aspect, each of $R^{1b}$, $R^{1c}$, and $R^{1d}$ is hydrogen; and $R^{1a}$ is —CN. In a still further aspect, each of $R^{1b}$, $R^{1c}$, and $R^{1d}$ is hydrogen; and $R^{1a}$ is methyl.

In a further aspect, each of $R^{1b}$, $R^{1c}$, and $R^{1d}$ is hydrogen; and $R^{1a}$ is halogen. In a still further aspect, each of $R^{1b}$, $R^{1c}$, and $R^{1d}$ is hydrogen; and $R^{1a}$ is —F. In a yet further aspect, each of $R^{1b}$, $R^{1c}$, and $R^{1d}$ is hydrogen; and $R^{1a}$ is —Cl. In an even further aspect, each of $R^{1b}$, $R^{1c}$, and $R^{1d}$ is hydrogen; and $R^{1a}$ is —Br b. $R^2$ Groups In various aspects, $R^2$ is —CN or a moiety having a structure represented by a formula:

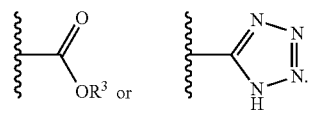

In a further aspect, $R^2$ is —CN.
In a further aspect, $R^2$ is a moiety having a structure represented by a formula:

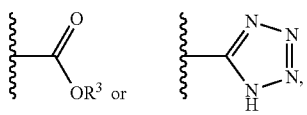

$R^3$ is hydrogen or C1-C4 alkyl.

In a further aspect, $R^2$ is a moiety having a structure represented by a formula:

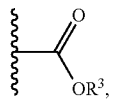

and $R^3$ is hydrogen or C1-C4 alkyl.

In a further aspect, $R^2$ is a moiety having a structure represented by a formula:

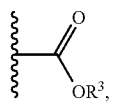

and $R^3$ is hydrogen, methyl, ethyl, propyl, or isopropyl.

In a further aspect, $R^2$ is a moiety having a structure represented by a formula:

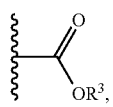

and $R^3$ is methyl.

In a further aspect, $R^2$ is a moiety having a structure represented by a formula:

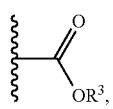

and $R^3$ is ethyl.

In a further aspect, $R^2$ is a moiety having a structure represented by a formula:

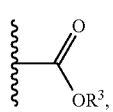

and $R^3$ is hydrogen.

In a further aspect, $R^2$ is a moiety having a structure represented by a formula:

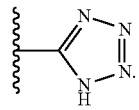

c. $R^3$ Groups

In various aspects, $R^3$ is hydrogen or C1-C4 alkyl. In a further aspect, $R^3$ is hydrogen.

In a further aspect, $R^3$ is hydrogen, methyl, ethyl, propyl, or isopropyl. In a still further aspect, $R^3$ is hydrogen, methyl, or ethyl. In a yet further aspect, $R^3$ is hydrogen or methyl. In an even further aspect, $R^3$ is hydrogen or ethyl. In a yet further aspect, $R^3$ is hydrogen or propyl. In an even further aspect, $R^3$ is hydrogen or isopropyl.

In various aspects, $R^3$ is C1-C4 alkyl. In a further aspect, $R^3$ is methyl, ethyl, propyl, or isopropyl. In a still further aspect, $R^3$ is methyl or ethyl. In an even further aspect, $R^3$ is methyl. In a still further aspect, $R^3$ is ethyl. In a yet further aspect, $R^3$ is propyl. In an even further aspect, $R^3$ is isopropyl.

d. L Groups

In various aspects, L is $(CH_2)_n$ or a moiety having a structure represented by a formula:

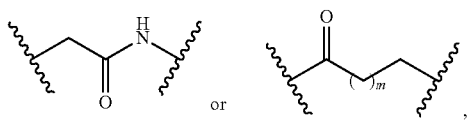

and m is an integer with a value of 0 or 1.

In a further aspect, L is $(CH_2)_n$; and n is an integer with a value of 0, 1, 2, 3, or 4. In a still further aspect, L is $(CH_2)_n$; and n is an integer with a value of 0, 1, 2, or 3. In a yet further aspect, L is $(CH_2)_n$; and n is an integer with a value of 0, 1, or 2. In an even further aspect, L is $(CH_2)_n$; and n is an integer with a value of 0 or 1. In a still further aspect, L is $(CH_2)_n$; and n is an integer with a value of 0. In a yet further aspect, L is $(CH_2)_n$; and n is an integer with a value of 1. In an even further aspect, L is $(CH_2)_n$; and n is an integer with a value of 2. In a still further aspect, L is $(CH_2)_n$; and n is an integer with a value of 3. In a yet further aspect, L is $(CH_2)_n$; and n is an integer with a value of 4.

In a further aspect, L is a moiety having a structure represented by a formula:

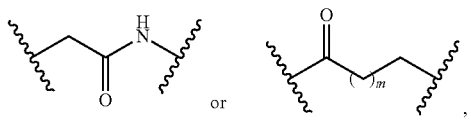

m is an integer with a value of 0 or 1.

In a further aspect, L is a moiety having a structure represented by a formula:

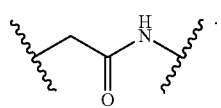 [SMILES: *CC(=O)N*]

In a further aspect, L is a moiety having a structure represented by a formula:

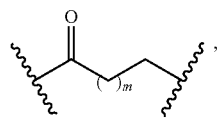

m is an integer with a value of 0 or 1.

In a further aspect, L is a moiety having a structure represented by a formula:

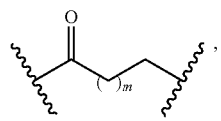

m is an integer with a value of 0.

In a further aspect, L is a moiety having a structure represented by a formula:

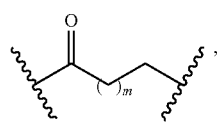

m is an integer with a value of 1.

e. Halogen (X)

In one aspect, halogen is fluoro, chloro, bromo or iodo. In a still further aspect, halogen is fluoro, chloro, or bromo. In a yet further aspect, halogen is fluoro or chloro. In a further aspect, halogen is fluoro. In an even further aspect, halogen is chloro or bromo. In an even further aspect, halogen is chloro. In a yet further aspect, halogen is iodo. In a still further aspect, halogen is bromo.

It is also contemplated that pseudohalogens (e.g. triflate, mesylate, brosylate, etc.) can be used as leaving groups in place of halogens in certain aspects.

2. Example Compounds

In one aspect, a compound can be present as:

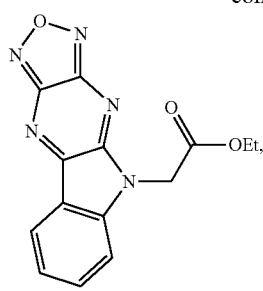
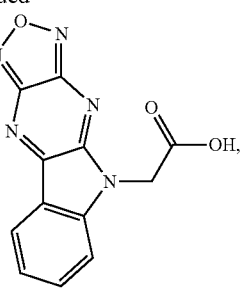

-continued

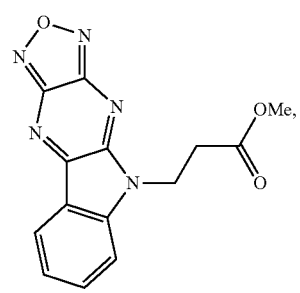

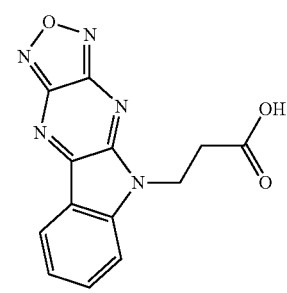

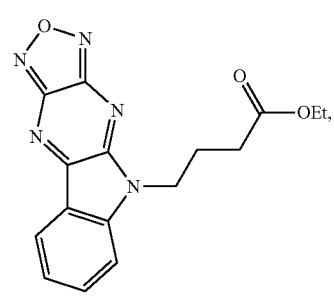

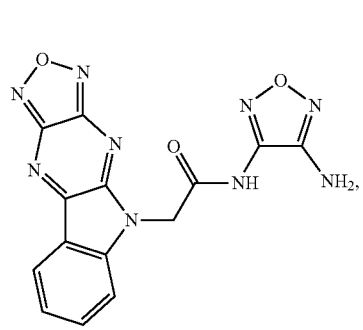
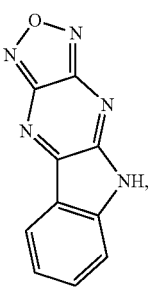
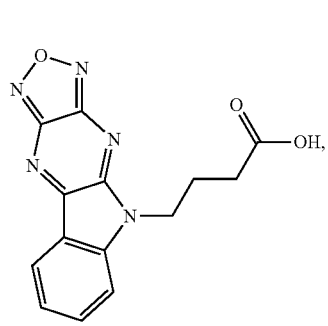
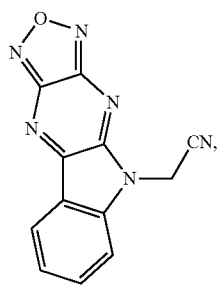

-continued

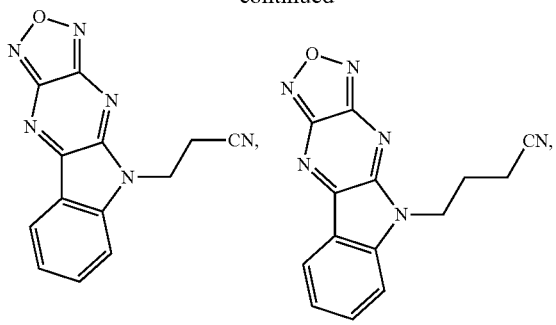

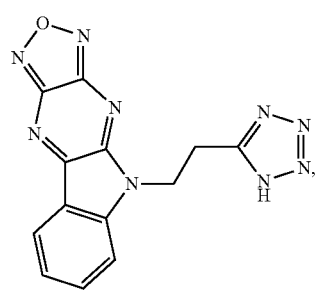

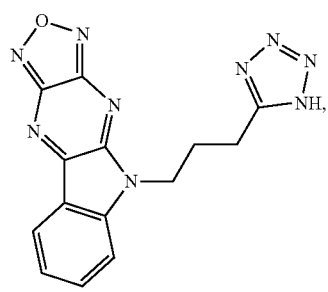

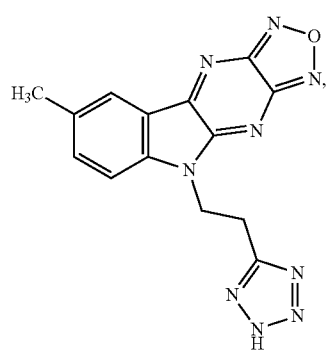

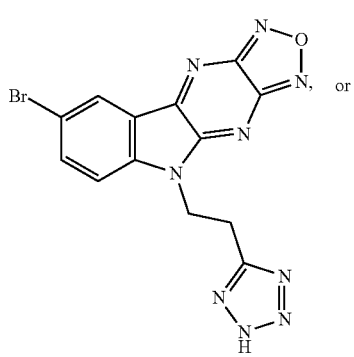 or

-continued

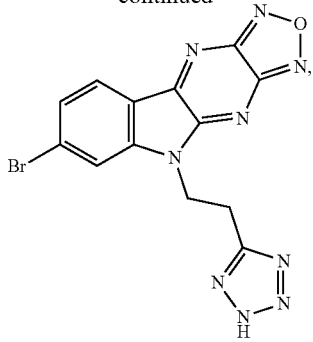

or a combination thereof.

It is contemplated that one or more compounds can optionally be omitted from the disclosed invention.

C. PHARMACEUTICAL COMPOSITIONS

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require inhibition of β-catenin/Tcf protein-protein interactions an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for inhibiting β-catenin/Tcf protein-protein interactions (e.g., treatment of one or more disorders of uncontrolled cellular proliferation associated with β-catenin/Tcf protein-protein interaction dysfunction or Wnt dysregulation) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

In a further aspect, the pharmaceutical composition further comprises a hormone therapy agent. In a still further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the pharmaceutical composition further comprises a chemotherapeutic agent. In a still further aspect, the chemotherapeutic agent is selected from one or more of the group consisting of an alkylating agent, an antimetabolite agent, an antineoplastic antibiotic agent, a mitotic inhibitor agent, a mTor inhibitor agent or other chemotherapeutic agent, or a pharmaceutically acceptable salt thereof. In yet a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof. In an even further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof. In a still further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof. In yet a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof. In an even further aspect, the mTor inhibitor agent is selected from one or more of the group consisting of everolimus, siroliumus, and temsirolimus, or a pharmaceutically acceptable salt thereof.

It is understood that the disclosed pharmaceutical compositions can be prepared from the disclosed compounds. It is also understood that the disclosed pharmaceutical compositions can be employed in the disclosed methods of using.

D. METHODS OF MAKING THE COMPOUNDS

In one aspect, the invention relates to methods of making compounds useful as inhibitors of β-catenin/Tcf PPIs, which can be useful in the treatment of cancers and fibrotic diseases associated with β-catenin/Tcf and other diseases in which β-catenin/Tcf PPIs are involved.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

The disclosed compounds can be prepared by various routes. In certain specific examples, the disclosed compounds can be prepared by Routes I and II, as described and exemplified below.

In a further aspect, a compound comprises the product of the disclosed methods. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, substituted 5H-[1,2,5]oxadiazolo[3',4':5,6]pyrazino[2,3-b]indole analogs can be prepared as shown below.

SCHEME 1A.

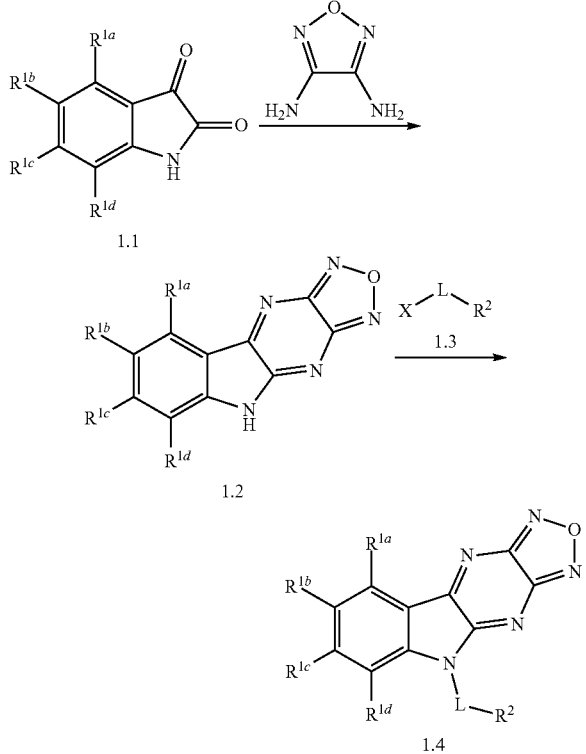

Compounds are represented in generic form, with substituents as noted in compound descriptions elsewhere herein. A more specific example is set forth below.

SCHEME 1B.

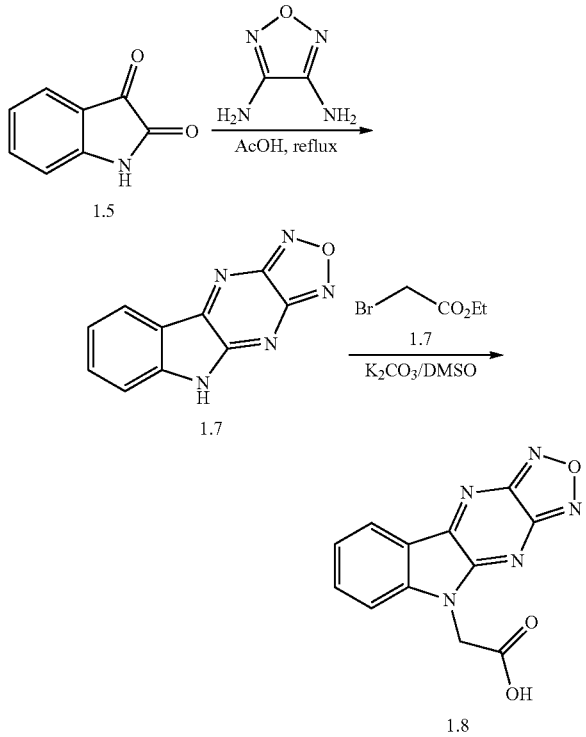

In one aspect, the synthesis of 5H-[1,2,5]oxadiazolo[3',4':5,6]pyrazino[2,3-b]indole analogs can begin with a substituted 4-indoline-2,3-dione. Indoline-2,3-diones are either commercially available or readily prepared by one skilled in the art. Thus, compounds of type 1.8, and similar compounds, can be prepared according to reaction Scheme 1B above. Compounds of type 1.6 can be prepared by a cyclization reaction of 1,2,5-oxadiazole-3,4-diamine. The cyclization reaction is carried out in the presence of an appropriate acid, e.g., acetic acid as shown above, at an appropriate temperature, e.g., refluxing conditions as shown above. Compounds of type 1.8 can be prepared by an aza-Michael addition reaction of an appropriate nucleophile, e.g., 1.7 as shown above. Appropriate nucleophiles are commercially available or prepared by methods known to one skilled in the art. The aza-Michael addition reaction is carried out in the presence of an appropriate base, e.g., potassium carbonate as shown above. As can be appreciated by one skilled in the art, the above reaction provides an example of a generalized approach wherein compounds similar in structure to the specific reactants above (compounds similar to compounds of type 1.1, 1.2, and 1.3), can be substituted in the reaction to provide substituted 5H-[1,2,5]oxadiazolo[3',4':5,6]pyrazino[2,3-b]indole analogs similar to Formula 1.4.

2. Route II

In one aspect, substituted 5H-[1,2,5]oxadiazolo[3',4':5,6]pyrazino[2,3-b]indole analogs can be prepared as shown below.

SCHEME 2A.

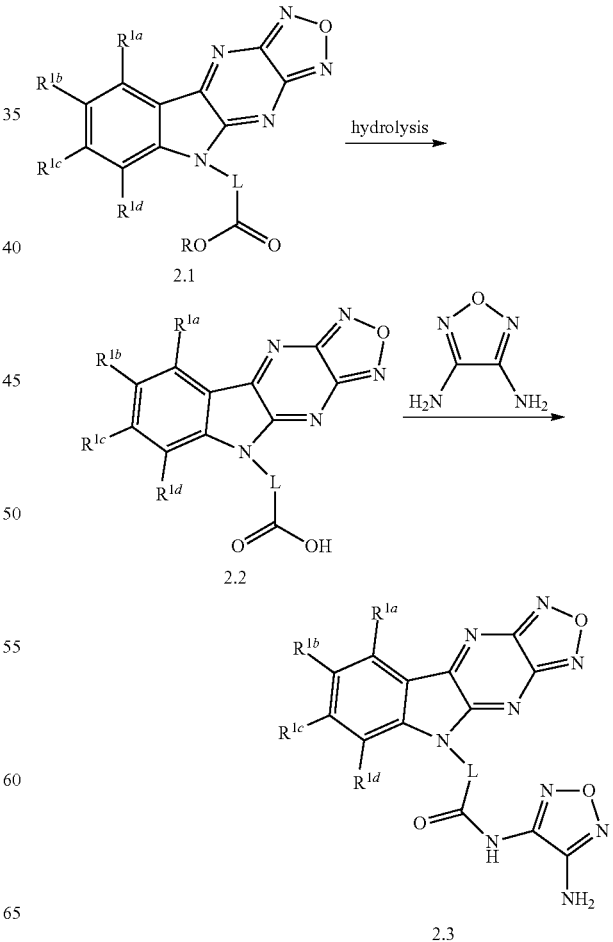

Compounds are represented in generic form, with substituents as noted in compound descriptions elsewhere herein. A more specific example is set forth below.

SCHEME 2B.

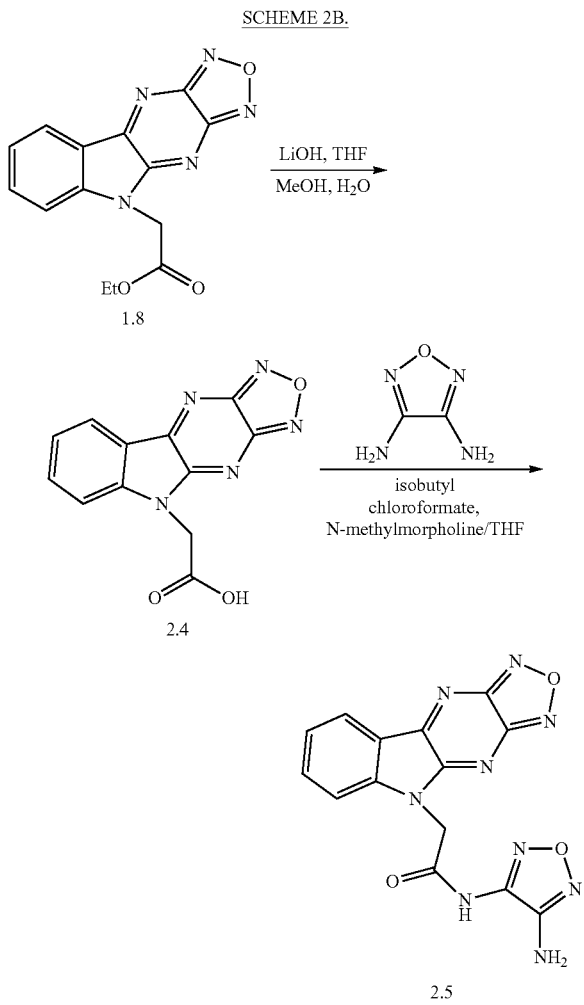

In one aspect, the synthesis of 5H-[1,2,5]oxadiazolo[3', 4':5,6]pyrazino[2,3-b]indole analogs can begin with a substituted ester. Thus, compounds of type 2.5, and similar compounds, can be prepared according to reaction Scheme 2B above. Compounds of type 2.4 can be prepared by a hydrolysis reaction of an appropriate ester, e.g., 1.8 as shown above. The hydrolysis is carried out in the presence of an appropriate base, e.g., lithium hydroxide as shown above, in an appropriate solvent, e.g., methanol and water as shown above. Compounds of type 2.5 can be prepared by a coupling reaction of an appropriate amine, e.g., 1,2,5-oxadiazole-3,4-diamine as shown above. Appropriate amines are commercially available or prepared by methods known to one skilled in the art. The coupling reaction is carried out in the presence of an appropriate coupling agent, e.g., isobutyl chloroformate as shown above, and an appropriate base, e.g., N-methylmorpholine as shown above. As can be appreciated by one skilled in the art, the above reaction provides an example of a generalized approach wherein compounds similar in structure to the specific reactants above (compounds similar to compounds of type 2.1, and 2.2), can be substituted in the reaction to provide substituted 5H-[1,2,5] oxadiazolo[3',4': 5,6]pyrazino[2,3-b]indole analogs similar to Formula 2.3.

E. METHODS OF USING THE COMPOUNDS AND COMPOSITIONS

The pharmaceutical compositions and methods of the present invention can further comprise other therapeutically active compounds as noted herein which are usually applied in the treatment of the above mentioned pathological conditions.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

1. Treatment Methods

The compounds disclosed herein are useful for treating, preventing, ameliorating, controlling or reducing the risk of a variety of disorders wherein the patient or subject would benefit from inhibition or negative modulation of β-catenin/Tcf protein-protein interaction. In one aspect, a treatment can include selective inhibition of β-catenin/Tcf protein-protein interaction to an extent effective to effect down-regulation of Wnt pathway signaling activity. In one aspect, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders, for which β-catenin/Tcf protein-protein interaction inhibition is predicted to be beneficial, in a subject comprising the step of administering to the subject at least one disclosed compound; at least one disclosed pharmaceutical composition; and/or at least one disclosed product in a dosage and amount effective to treat the disorder in the subject.

In one aspect, provided is a method for treating a disorder of uncontrolled cellular proliferation, comprising: administering to a subject at least one disclosed compound; at least one disclosed pharmaceutical composition; and/or at least one disclosed product in a dosage and amount effective to treat the disorder in the subject. In a further aspect, provided is a method for treating or preventing a disorder characterized by fibrosis, comprising: administering to a subject at least one disclosed compound; at least one disclosed pharmaceutical composition; and/or at least one disclosed product in a dosage and amount effective to treat the disorder in the subject. Also provided is a method for the treatment of a disorder in a mammal comprising the step of administering to the mammal at least one disclosed compound, composition, or medicament.

The invention is directed at the use of described chemical compositions to treat diseases or disorders in patients (preferably human) wherein β-catenin/Tcf protein-protein interaction inhibition would be predicted to have a therapeutic effect, such as disorders of uncontrolled cellular proliferation (e.g. tumors and cancers) and disorders characterized by fibrosis (e.g. polycystic kidney disease), by administering one or more disclosed compounds or products.

The compounds disclosed herein are useful for treating, preventing, ameliorating, controlling or reducing the risk of a variety of disorders of uncontrolled cellular proliferation. In one aspect, the disorder of uncontrolled cellular proliferation is associated with dysregulation of the Wnt signaling pathway. In a further aspect, the Wnt signaling pathway dysregulation is associated with a β-catenin/Tcf protein-protein interaction dysfunction.

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

Examples of disorders associated with β-catenin/Tcf protein-protein interaction dysfunction include a disorder of uncontrolled cellular proliferation. In a still further aspect, the disorder is cancer. In yet a further aspect, the cancer is a sarcoma. In an even further aspect, the cancer is a carcinoma. In a still further aspect, the cancer is a hematological cancer. In a yet further aspect, the cancer is a solid tumor.

It is understood that cancer refers to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma, B-cell non-Hodgkin lymphoma, and large B-cell lymphoma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, liver, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In a further aspect, the cancer is selected from a cancer of the breast, cervix, gastrointestinal tract, colorectal tract, brain, skin, prostate, ovary, thyroid, testes, genitourinary tract, pancreas, and endometrias. In a still further aspect, the cancer is a cancer of the breast. In yet a further aspect, the cancer of the breast is a hormone resistant cancer. In an even further aspect, the cancer of the breast is a hormone resistant cancer. In a still further aspect, the cancer is a cancer of the cervix. In yet a further aspect, the cancer is a cancer of the ovary. In an even further aspect, the cancer is a cancer of the endometrias. In a still further aspect, the cancer is a cancer of the genitourinary tract. In yet a further aspect, the cancer is a cancer of the colorectal tract. In an even further aspect, the cancer of the colorectal tract is a colorectal carcinoma. In a still further aspect, the cancer is a cancer of the gastrointestinal tract. In yet a further aspect, the cancer of the gastrointestinal tract is a gastrointestinal stromal tumor. In an even further aspect, the cancer is a cancer of the skin. In a still further aspect, the cancer of the skin is a melanoma. In yet a further aspect, the cancer is a cancer of the brain. In an even further aspect, the cancer of the brain is a glioma. In a still further aspect, the glioma is glioblastoma multiforme. In yet a further aspect, glioma is selected from is selected from a ependymoma, astrocytoma, oligodendroglioma, and oligoastrocytoma. In an even further aspect, the cancer of the brain is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, and hemangiopercytoma. In a still further aspect, the hematological cancer is selected from a leukemia, lymphoma, chronic myeloproliferative disorder, myelodysplastic syndrome, myeloproliferative neoplasm, and plasma cell neoplasm (myeloma). In yet a further aspect, the hematological cancer is leukemia. In an even further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia. In a still further aspect, the leukemia is acute lymphocytic leukemia. In yet a further aspect, the hematological cancer is lymphoma. In an even further aspect, the hematological cancer is myeloma. In a still further aspect, the myeloma is multiple myeloma.

In a further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer is selected from breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma).

In a further aspect, the cancer is treatment-resistant. In a still further aspect, the cancer is resistant to treatment with the at least one chemotherapeutic agent. In yet a further aspect, the cancer is resistant to treatment with the at least one hormone therapy agent.

In various aspects, disorders associated with a β-catenin/Tcf protein-protein interaction dysfunction include disorders characterized by fibrosis. In a further aspect, the fibrotic disease is selected from pulmonary fibrosis, liver fibrosis, and polycystic kidney disease. In a still further aspect, the fibrosis is pulmonary fibrosis.

The compounds are further useful in a method for the prevention, treatment, control, amelioration, or reduction of risk of the diseases, disorders and conditions noted herein. The compounds are further useful in a method for the prevention, treatment, control, amelioration, or reduction of risk of the aforementioned diseases, disorders and conditions in combination with other agents.

The present invention is further directed to administration of a β-catenin/Tcf protein-protein interaction inhibitor for improving treatment outcomes in the context of disorders of uncontrolled cellular proliferation, including cancer. That is, in one aspect, the invention relates to a cotherapeutic method comprising the step of administering to a mammal an effective amount and dosage of at least one compound of the invention in connection with cancer therapy.

In a further aspect, administration improves treatment outcomes in the context of cancer therapy. Administration in connection with cancer therapy can be continuous or intermittent. Administration need not be simultaneous with therapy and can be before, during, and/or after therapy. For example, cancer therapy can be provided within 1, 2, 3, 4, 5, 6, 7 days before or after administration of the compound. As a further example, cancer therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-cancer therapeutic agents. In a further aspect, the anti-cancer therapeutic agent is selected from 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab TiuxetanIdamycin®, Idarubicin, Ifex®, IFN-alphalfosfamide, IL-11IL-2Imatinib mesylate, Imidazole CarboxamideInterferon alfa, Interferon Alfa-2b (PEG Conjugate), Interleukin-2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Orapred®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a) Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna R, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®.

In another aspect, the subject compounds can be administered in combination with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab TiuxetanIdamycin®, Idarubicin, Ifex®, IFN-alphalfosfamide, IL-11IL-2Imatinib mesylate, Imidazole CarboxamideInterferon alfa, Interferon Alfa-2b (PEG Conjugate), Interleukin-2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™ Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Oraped®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a) Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®.

In another aspect, the subject compound can be used in combination with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab TiuxetanIdamycin®, Idarubicin, Ifex®, IFN-alphalfosfamide, IL-11IL-2Imatinib mesylate, Imidazole CarboxamideInterferon alfa, Interferon Alfa-2b (PEG Conjugate), Interleukin-2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™ Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Orapred®, Orasone®, Oxaliplatin, P, Paclitaxel, Paclitaxel Protein-bound, Pamidronate, Panitumumab, Panretin ®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a) Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®

In the treatment of conditions which require inhibition or negative modulation of β-catenin/Tcf protein-protein interaction, an appropriate dosage level will generally be about 0.01 to 1000 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to methods for inhibiting or negatively modulating β-catenin/Tcf protein-protein interaction in at least one cell, comprising the step of contacting the at least one cell with at least one compound of the invention, in an amount effective to negatively modulate β-catenin/Tcf protein-protein interaction in the at least one cell. In a further aspect, the cell is mammalian, for example human. In a further aspect, the cell has been isolated from a subject prior to the contacting step. In a further aspect, contacting is via administration to a subject.

In various aspects, disclosed are methods for the treatment of a disorder of uncontrolled cellular proliferation associated with a β-catenin/Tcf dysfunction in a mammal comprising the step of administering to the mammal an effective amount of at least one compound having a structure represented by a formula:

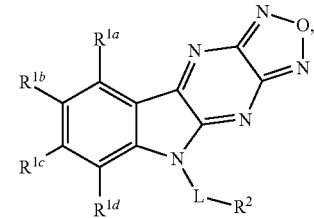

wherein each of $R^{1a}$, $R^{1b}$, $R^{1c}$, and $R^{1d}$ is independently hydrogen, halogen, —CN, C1-C4 alkyl, or C1-C4 haloalkyl; wherein L is $(CH_2)_n$ or a moiety having a structure represented by a formula:

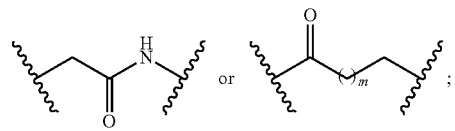

wherein m is an integer with a value of 0 or 1; wherein n is an integer with a value of 0, 1, 2, 3, or 4; and wherein $R^2$ is —CN or a moiety having a structure represented by a formula:

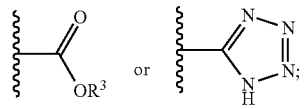

wherein $R^3$ is hydrogen or C1-C4 alkyl; or a pharmaceutically acceptable salt thereof.

Also disclosed are methods for the treatment of a disorder of uncontrolled cellular proliferation associated with a β-catenin/Tcf protein-protein interaction dysfunction in a mammal comprising the step of administering to the mammal an effective amount of at least one compound having a structure represented by a formula:

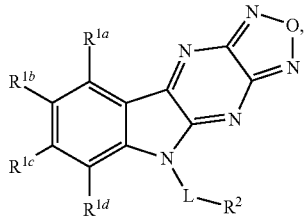

wherein each of $R^{1a}$, $R^{1b}$, $R^{1c}$, and $R^{1d}$ is independently hydrogen, halogen, —CN, C1-C4 alkyl, or C1-C4 haloalkyl; wherein L is $(CH_2)_n$ or a moiety having a structure represented by a formula:

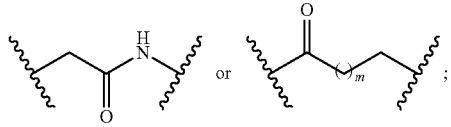

wherein m is an integer with a value of 0 or 1; wherein n is an integer with a value of 0, 1, 2, 3, or 4; and wherein $R^2$ is —CN or a moiety having a structure represented by a formula:

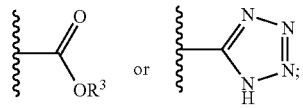

wherein $R^3$ is hydrogen or C1-C4 alkyl; or a pharmaceutically acceptable salt thereof.

Also disclosed are methods for inhibiting β-catenin/Tcf protein-protein interactions in a mammal comprising the step of administering to the mammal an effective amount of at least one compound having a structure represented by a formula:

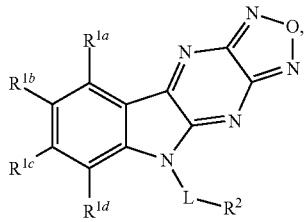

wherein each of $R^{1a}$, $R^{1b}$, $R^{1c}$, and $R^{1d}$ is independently hydrogen, halogen, —CN, C1-C4 alkyl, or C1-C4 haloalkyl; wherein L is $(CH_2)_n$ or a moiety having a structure represented by a formula:

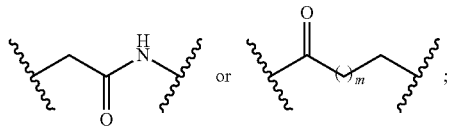

wherein m is an integer with a value of 0 or 1; wherein n is an integer with a value of 0, 1, 2, 3, or 4; and wherein $R^2$ is —CN or a moiety having a structure represented by a formula:

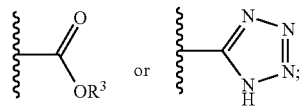

wherein $R^3$ is hydrogen or C1-C4 alkyl; or a pharmaceutically acceptable salt thereof.

Also disclosed are methods for down-regulation of the Wnt pathway in a mammal comprising the step of administering to the mammal an effective amount of at least one compound having a structure represented by a formula:

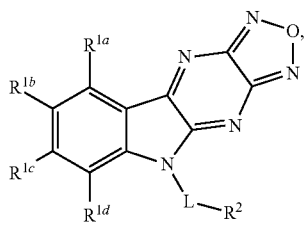

wherein each of $R^{1a}$, $R^{1b}$, $R^{1c}$, and $R^{1d}$ is independently hydrogen, halogen, —CN, C1-C4 alkyl, or C1-C4 haloalkyl; wherein L is $(CH_2)_n$ or a moiety having a structure represented by a formula:

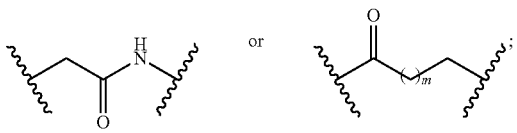

wherein m is an integer with a value of 0 or 1; wherein n is an integer with a value of 0, 1, 2, 3, or 4; and wherein $R^2$ is —CN or a moiety having a structure represented by a formula:

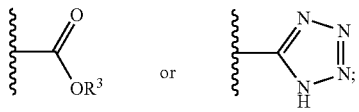

wherein $R^3$ is hydrogen or C1-C4 alkyl; or a pharmaceutically acceptable salt thereof.

In a further aspect, the effective amount is a therapeutically effective amount. In a still further aspect, the effective amount is a prophylactically effective amount.

In a further aspect, the mammal is a human. In a still further aspect, the mammal has been diagnosed with a need for treatment of the disorder prior to the administering step. In yet a further aspect, the mammal has been diagnosed with a need for inhibiting protein-protein interactions of β-catenin and Tcf activity prior to the administering step. In an even further aspect, the method further comprises the step of identifying a mammal in need of treatment of the disorder. In a still further aspect, the method further comprises the step of identifying a mammal in need for inhibiting protein-protein interactions of β-catenin and Tcf. In yet a further aspect, inhibiting protein-protein interactions of β-catenin and Tcf is associated with treating a cancer.

In a further aspect, the mammal is human; and wherein the human has been identified to have a 1q21 chromosomal abnormality.

In a further aspect, the mammal is human; and wherein the step of identifying the human in need of treatment of the disorder comprises the steps of: (a) obtaining a sample from the human; wherein the sample comprises cells suspected of being associated with the disorder of uncontrolled cellular proliferation; (b) determining if the sample comprises cells with a 1q21 chromosomal abnormality; and (c) administering to the human the compound when the sample is positive for a 1q21 chromosomal abnormality.

Also disclosed are methods for inhibiting β-catenin/Tcf protein-protein interactions in at least one cell comprising the step comprising the step of contacting the cell with an effective amount of at least one compound having a structure represented by a formula:

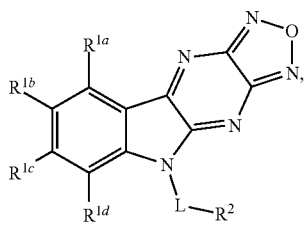

wherein each of $R^{1a}$, $R^{1b}$, $R^{1c}$, and $R^{1d}$ is independently hydrogen, halogen, —CN, C1-C4 alkyl, or C1-C4 haloalkyl; wherein L is $(CH_2)_n$ or a moiety having a structure represented by a formula:

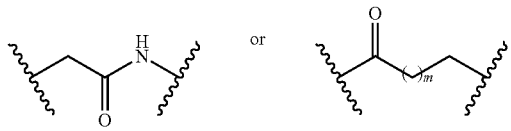

wherein m is an integer with a value of 0 or 1; wherein n is an integer with a value of 0, 1, 2, 3, or 4; and wherein $R^2$ is —CN or a moiety having a structure represented by a formula:

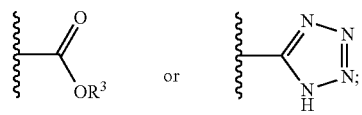

wherein $R^3$ is hydrogen or C1-C4 alkyl; or a pharmaceutically acceptable salt thereof.

In a further aspect, the cell is mammalian. In a still further aspect, the cell is human. In yet a further aspect, the cell has been isolated from a mammal prior to the contacting step. In an even further aspect, contacting is via administration to a mammal. In a still further aspect, the mammal has been diagnosed with a need for inhibiting protein-protein interactions of β-catenin and BCL9 prior to the administering step. In yet a further aspect, the mammal has been diagnosed with a need for treatment of a disorder related to protein-protein interactions of β-catenin and BCL9 prior to the administering step. In an even further aspect, the disorder is a disorder of uncontrolled cellular proliferation. In a still further aspect, the disorder of uncontrolled cellular proliferation is a cancer.

2. Manufacture of a Medicament

In one aspect, the invention relates to a method for the manufacture of a medicament for inhibition of β-catenin/Tcf protein-protein interaction in a mammal comprising combining a therapeutically effective amount of a disclosed compound or product of a disclosed method with a pharmaceutically acceptable carrier or diluent. In a further aspect, the invention relates to a method for the manufacture of a medicament for inhibition of the Wnt signaling pathway in a mammal comprising combining a therapeutically effective amount of a disclosed compound or product of a disclosed method with a pharmaceutically acceptable carrier or diluent.

3. Use of Compounds

In one aspect, the invention relates to the use of a compound having a structure represented by a formula:

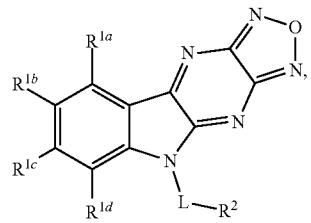

wherein each of $R^{1a}$, $R^{1b}$, $R^{1c}$, and $R^{1d}$ is independently hydrogen, halogen, —CN, C1-C4 alkyl, or C1-C4 haloalkyl; wherein L is $(CH_2)_n$ or a moiety having a structure represented by a formula:

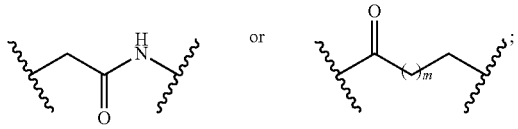

wherein m is an integer with a value of 0 or 1; wherein n is an integer with a value of 0, 1, 2, 3, or 4; and wherein $R^2$ is —CN or a moiety having a structure represented by a formula:

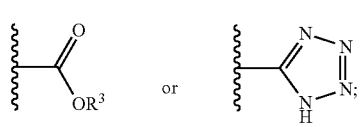

wherein $R^3$ is hydrogen or C1-C4 alkyl; or a pharmaceutically acceptable salt thereof.

In a further aspect, the invention relates to the use of at least one disclosed compound for inhibiting β-catenin/Tcf activity.

In a further aspect, the invention relates to the use of at least one disclosed compound for administration to a subject; wherein the subject has a disorder of uncontrolled cellular proliferation.

In a further aspect, the compound of the use is a disclosed compound or a product of a disclosed method of making a compound.

In a still further aspect, the use is therapeutic treatment of a mammal. In a yet further aspect, the mammal is human.

In a further aspect, the use is inhibition of β-catenin/Tcf protein-protein interactions. In a still further aspect, the use is inhibition of the Wnt signaling pathway. In a still further aspect, the need for inhibition of β-catenin/Tcf protein-protein interactions is associated with treatment of a disorder of uncontrolled cellular proliferation. In a yet further aspect, inhibition of the Wnt signaling pathway treats a disorder of uncontrolled cellular proliferation.

In a further aspect, the disorder of uncontrolled cellular proliferation is a cancer. In an even further aspect, cancer is a leukemia. In a still further aspect, the cancer is a myeloma. In a yet further aspect, cancer is a solid tumor. In an even further aspect, the cancer is a lymphoma.

In a further aspect, the cancer is selected from the cancer is selected from cancers of the blood, brain, prostate, genitourinary tract, gastrointestinal tract, colon, rectum, breast, liver, kidney, lymphatic system, stomach, lung, pancreas, and skin. In an even further aspect, the cancer is selected from a cancer of the colon, rectum, breast, prostate, liver, skin and lung. In a still further aspect, the cancer is selected from a cancer of the breast, ovary, testes and prostate. In a yet further aspect, the cancer is a cancer of the breast. In various aspect, the cancer is a cancer of the liver. In a still further aspect, the cancer is a cancer of the prostate. In a yet further aspect, the cancer is a cancer of the colon or rectum.

In a further aspect, the disorder is characterized by fibrosis. In a yet further aspect, the fibrotic disorder is selected from pulmonary fibrosis, liver fibrosis, and polycystic kidney disease.

4. Kits

In one aspect, the invention relates to a kit comprising at least one compound having a structure represented by a formula:

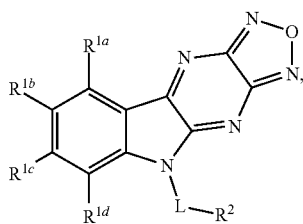

wherein each of $R^{1a}$, $R^{1b}$, $R^{1c}$, and $R^{1d}$ is independently hydrogen, halogen, —CN, C1-C4 alkyl, or C1-C4 haloalkyl; wherein L is $(CH_2)_n$ or a moiety having a structure represented by a formula:

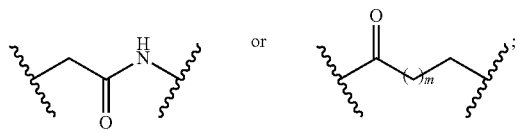

wherein m is an integer with a value of 0 or 1; wherein n is an integer with a value of 0, 1, 2, 3, or 4; and wherein $R^2$ is —CN or a moiety having a structure represented by a formula:

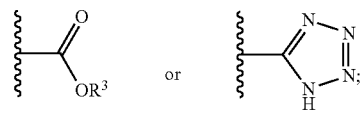

wherein $R^3$ is hydrogen or C1-C4 alkyl; or a pharmaceutically acceptable salt thereof, and one or more of:

(a) at least one agent known to increase Tcf activity;
(b) at least one agent known to increase β-catenin activity;
(c) at least one agent known to decrease Tcf activity;
(d) at least one agent known to decrease β-catenin activity;
(e) at least one agent known to treat a disease of uncontrolled cellular proliferation;
(f) instructions for treating a disorder associated uncontrolled cellular proliferation; or
(g) instructions for treating a disorder associated with a β-catenin/Tcf dysfunction.

In a further aspect, the compound of the kit is a disclosed compound or a product of a disclosed method of making a compound.

In a further aspect, the at least one compound and the at least one agent are co-formulated. In a still further aspect, the at least one compound or the at least one product and the at least one agent are co-packaged.

In a further aspect, the at least one agent is a hormone therapy agent. In a yet further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the at least one agent is a chemotherapeutic agent. In a yet further aspect, the chemotherapeutic agent is selected from one or more of the group consisting of an alkylating agent, an antimetabolite agent, an antineoplastic antibiotic agent, a mitotic inhibitor agent, a mTor inhibitor agent or other chemotherapeutic agent.

In a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

In a further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

In a further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

In a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

In a further aspect, the mTor inhibitor agent is selected from one or more of the group consisting of everolimus, siroliumus, and temsirolimus, or a pharmaceutically acceptable salt, hydrate, solvate, or polymorph thereof.

In a further aspect, the disorder of uncontrolled cellular proliferation is associated with a β-catenin/Tcf protein-protein interaction dysfunction. In a still further aspect, the disorder of uncontrolled cellular proliferation is a cancer. In an even further aspect, cancer is a leukemia. In a still further aspect, the cancer is a sarcoma. In a yet further aspect, cancer is a solid tumor. In an even further aspect, the cancer is a lymphoma. In a still further aspect, the cancer is selected from chronic lymphocytic leukemia, small lymphocytic lymphoma, B-cell non-Hodgkin lymphoma, and large B-cell lymphoma. In a yet further aspect, the cancer is selected from cancers of the blood, brain, genitourinary tract, gastrointestinal tract, colon, rectum, breast, liver, kidney, lymphatic system, stomach, lung, pancreas, and skin. In an even further aspect, the cancer is selected from a cancer of the lung and liver. In a still further aspect, the cancer is selected from a cancer of the breast, ovary, testes and prostate. In a yet further aspect, the cancer is a cancer of the breast. In various aspect, the cancer is a cancer of the ovary. In a still further aspect, the cancer is a cancer of the prostate. In a yet further aspect, the cancer is a cancer of the testes.

In a further aspect, the instructions further comprise providing the compound in connection with a surgical procedure. In a still further aspect, the instructions provide that surgery is performed prior to the administering of at least one compound. In yet a further aspect, the instructions provide that surgery is performed after the administering of at least one compound. In an even further aspect, the instructions provide that the administering of at least one compound is to effect presurgical debulking of a tumor. In a still further aspect, the instructions provide that the administering of at least one compound is to effect presurgical debulking of a tumor.

In a further aspect, the instructions further comprise providing the compound in connection with radiotherapy. In a still further aspect, the instructions provide that radiotherapy is performed prior to the administering of at least one compound. In yet a further aspect, the instructions provide that radiotherapy is performed after the step of the administering of at least one compound. In an even further aspect, the instructions provide that radiotherapy is performed at about the same time as the step of the administering of at least one compound.

In a further aspect, the instructions further comprise providing the compound in connection with at least one agent that is a chemotherapeutic agent.

5. Non-Medical Uses

Also provided are the uses of the disclosed compounds and products as pharmacological tools in the development and standardization of in vitro and in vivo test systems for the evaluation of the effects of inhibitors of β-catenin/Tcf protein-protein interactions in laboratory animals such as cats, dogs, rabbits, monkeys, rats and mice, as part of the search for new therapeutic agents that inhibit β-catenin/Tcf protein-protein interactions.

F. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

All reagents were purchased from Aldrich and Acros Organics and used without further purification unless stated otherwise. $^1$H NMR and $^{13}$C NMR spectra were recorded on a Varian VXR-500 (500 MHz), a Varian Inova-400 (400 MHz), or a Varian Unity-300 (300 MHz) spectrometer (125.7 MHz, 100 MHz, and 75 MHz for $^{13}$C NMR spectra, respectively) in d$^6$-DMSO, d$^6$-acetone, and CDCl$_3$. Chemical shifts were reported as values in parts per million (ppm), and the reference resonance peaks were set at 7.26 ppm (CHCl$_3$), 2.50 ppm [(CD$_2$H)$_2$SO], 2.05 ppm [(CD$_2$H)$_2$CO] for the $^1$H NMR spectra and 77.23 ppm (CDCl$_3$), 39.52 ppm (d$^6$-DMSO), and 29.84 ppm (d$^6$-acetone) for the $^{13}$C NMR spectra. Low-resolution and high-resolution mass spectra were determined on a Micromass Quattro II mass spectrometer with an ESI source. Thin-layer chromatography was carried out on E. Merck pre-coated silica gel 60 F254 plates with visualization accomplished with phosphomolybdic acid or ninhydrin spray reagent or with a UV-visible lamp. Column chromatography was performed with SilicaFlash@ F60 (230-400 mesh).

1. Protein Expression and Purification

β-Catenin V511S, V511S/I569S, and R469A mutants have been made previously (Gail et al. (2005) *J. Biol. Chem.* 280, 7107-7117; Huang et al. (2014) *ACS Chem. Biol.* 9, 193-201). Wild-type β-catenin and its mutants (residues 138-686) were cloned into a pET-28b vector carrying a C-terminal 6× histidine (Novagen) or a pEHISTEV vector carrying an N-terminal 6× histidine (from Dr. Hanting Liu, St. Andrew University, UK) and transformed into *E. coli* BL21 DE3 (Novagen). Cells were cultured in LB medium with 30 μg/mL kanamycin until the OD$_{600}$ was approximately 0.8, and then protein expression was induced with 400 μM of IPTG at 20° C. overnight. Cells were lysed by sonication. The proteins were purified by Ni-NTA affinity chromatography (30210, Qiagen) and dialyzed against a buffer containing 20 mM of Tris (pH 8.8), 100 mM NaCl, 10% glycerol, and 3 mM DTT. The purity of β-catenin was set to >95% as determined by SDS-PAGE gel analysis. Native non-denaturing gel electrophoresis experiment and the thermal-shift assay on an iCycler iQ Real Time Detection System (Bio-Rad) were performed for each purified protein. In the thermal shift assay, protein unfolding was evaluated through measuring the fluorescence changes of fluorescent dye Sypro Orange with purified β-catenin proteins. A temperature increment of 1° C./min was applied to monitor protein stability and detect protein aggregation. CD spectra were measured on a J-815 spectropolarimeter (Jasco). All spectra were recorded using a 1 mm path-length quartz cell. The CD spectra were averaged over three scans, and the wavelength was scanned from 260 to 190 nm in step of 1 nm. All spectra were recorded at room temperature, and the baseline was corrected by subtracting the CD spectra of a blank control containing all of the substances except protein. Samples were prepared at a concentration around 1-5 μM in a buffer of 10 mM potassium phosphate and 100 mM potassium fluoride at pH 7.0 to ensure that the transmission of light through the sample was not restricted. All proteins were stable, and no aggregation was observed under storage or assay conditions. Proteins were aliquoted and stored at −80 OC. C-Terminally biotinylated human Tcf4 (residues 7-51), C-terminally fluorescein-labeled human Tcf4 (residues 7-51), C-terminally fluorescein-labeled human E-cadherin (residues 819-873), and C-terminally fluorescein-labeled human APC-R3 (residues 1477-1519) were synthesized by InnoPep, Inc. (http://www.innopep.com/) and HPLC purified with purity >95%. The structures were validated by LC/MS (liquid chromatography/mass spectrometry). The peptide sequences are shown in Table 1.

an assay buffer of 137 mM NaCl, 2.7 mM KCl, 10 mM $Na_2HPO_4$, 2 mM $KH_2PO_4$, 100 μg/mL of bovine γ-globulin, and 0.01% Triton-X100 for 15 min at 4° C. Bovine γ-globulin and Triton-X100 were included in the assay buffer to decrease the likelihood of compound acting by aggregate formation. Different concentrations of the tested compounds in the assay buffer were added to each test plate to make a final volume of 100 μL. Each assay plate was covered black and gently mixed on an orbital shaker at 4° C. for 1.5 h to reach equilibrium before the polarization values were read. The $IC_{50}$ value was determined by nonlinear least-square analysis of GraphPad Prism 5.0. The $K_i$ values were derived (Nikolovska-Coleska et al. (2004) *Anal. Biochem.* 332, 261-273). Experiments were performed in triplicate and carried out in the presence of 1% DMSO. For the β-catenin/E-cadherin inhibition assay, 150 nM human β-catenin was incubated with 5 nM of C-terminally fluorescein-labeled human E-cadherin in the assay buffer for 30 min at 4° C. Different concentrations of the tested compounds in the assay buffer were added to each test plates to make a final volume of 100 μL. For the β-catenin/APC-R3 inhibition assay, 1440 nM human β-catenin was incubated with 5 nM of C-terminally fluorescein-labeled human APC-R3 in the assay buffer for 30 min at 4° C. Different concentrations of the tested compounds in the assay buffer were added to each test plates to make a final volume of 100 μL. In the AlphaScreen competitive inhibition assay for the β-catenin/Tcf4 PPI, 5 nM of C-terminally biotinylated human Tcf4 and 20 nM of N-terminally $His_6$-tagged human β-catenin were incubated in an assay buffer of 20 mM HEPES (pH 7.4), 100 mM NaCl, 0.1% BSA, and 0.001% Triton X-100 at 4° C. for 15 min. Different concentrations of the tested compounds

TABLE 1

| Peptide | Sequence |
|---|---|
| Biotinylated Human Tcf4 Peptide (residues 7-51) | H-$^7$GGGDDLGANDELISFKDEGEQEEKSSENSSAERDLA DVKSSLVNE$^{51}$K(Biotin)-NH$_2$ (SEQ. ID NO.: 1) |
| Fluorescein-Labeled Human Tcf4 Peptide (residues 7-51) | H-$^7$GGGDDLGANDELISFKDEGEQEEKSSENSSAERDLA DVKSSLVNE$^{51}$K(FITC)-NH$_2$ (SEQ. ID NO.: 2) |
| Fluorescein-labeled human E-cadherin (residues 819-873) | H-$^{819}$DTDPTAPPYDSLLVFDYEGSGSEAASLSSLNSSESD KDQDYDYLNEWGNRFKKLA$^{873}$K(FITC)-NH$_2$ (SEQ. ID NO.: 3) |
| Fluorescein-labeled human APC-R3 (residues 1477-1519) | H-$^{1477}$QRVQVLPDADTLLHFATESTPDGFSCSSSLSALSL DEPFIQKD$^{1519}$K(FITC)-NH$_2$ (SEQ. ID NO.: 4) |

2. FP and Alphascreen Assays

The procedures for the FP and AlphaScreen competitive inhibition assays have been described previously (Zhang et al. (2012) *Anal. Biochem.* 424, 57-63; Zhang et al. (2013) *ACS Med. Chem. Lett.* 4, 306-311). Briefly, all of the tested compounds were prepared as 10 mM DMSO stocks. In the primary screen, the concentrations of the compounds and DMSO were set to 50 μM and 1% (v/v). Only the compounds which AlphaScreen or FP signal decreases were greater than 50% in the single-point β-catenin/Tcf assay were evaluated by counter screen. Compounds that were confirmed active in the competitive inhibition assay and inactive in the counter screen were further evaluated with the dose-response relationship. In the FP competitive inhibition assay, 10 nM human β-catenin and 2.5 nM of C-terminally fluorescein-labeled human Tcf4 were incubated in (10-12 compound concentrations typically for each compound) were added in 20 μL assay buffer. The assay plates were covered black and gently mixed on an orbital shaker at 4° C. for 45 min. The streptavidin-coated donor beads and the nickel chelate acceptor beads were added to a final concentration of 10 μg/mL in 25 μL assay buffer. The mixture was incubated for 2 h at 4° C. before detection. The $IC_{50}$ value was then determined by nonlinear least-square analysis of GraphPad Prism 5.0, and the $K_i$ values were derived (Nikolovska-Coleska et al. (2004) *Anal. Biochem.* 332, 261-273).

3. Compounds

Compound numbers and structures are detailed in Table 2 below. Compounds 1 and 2 were purchased from Santa Cruz Biotechnology (Santa Cruz, Calif., USA) with the catalogue numbers of SC-3545 and SC-255013. Compound 3 was purchased from Calbiochem (Billerica, Mass., USA) with the catalogue number of 219331. Compounds 15-17 and 22-25 were purchased from Sigma Aldrich. Compounds 18 and 21 were purchased from Zelinsky Institute, Inc (Newark, Del., USA) with the catalogue numbers of UZI/7116003 and UZI/2587998. Compound 19A was purchased from InterBioScreen (Moscow, Russia) with the catalogue number of STOCK1S-52622. Compounds 8, 9, 19B, 20, and 26-38 were synthesized.

TABLE 2

| Cmpd. No. | Structure |
|---|---|
| 1 | 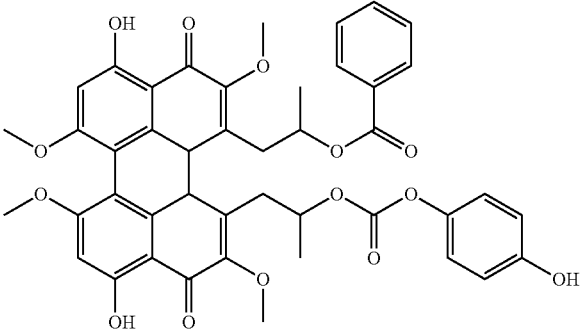<br>PFK115-584 |
| 2 | 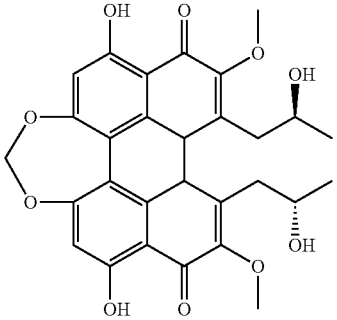<br>CGP049090 |
| 3 | 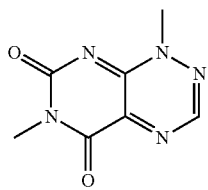<br>PFK118-310 |
| 4 | 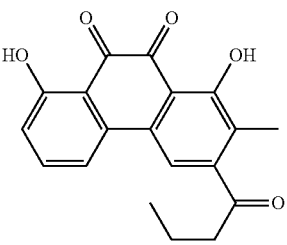<br>PFK118-744 |

TABLE 2-continued
| Cmpd. No. | Structure |
|---|---|
| 5 | 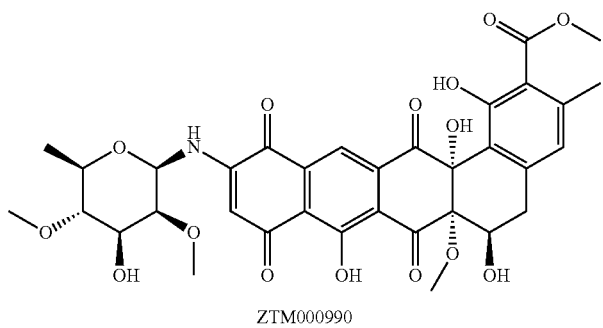<br>ZTM000990 |
| 6 | 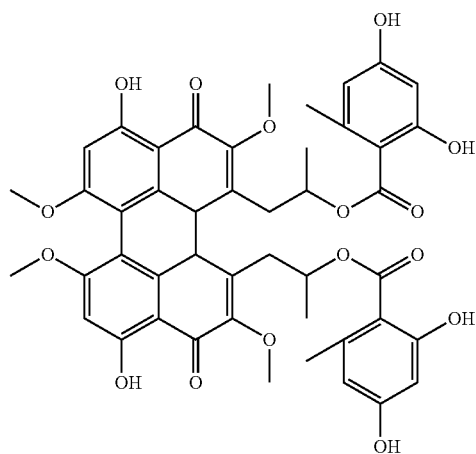<br>PFK222-815 |
| 7 | 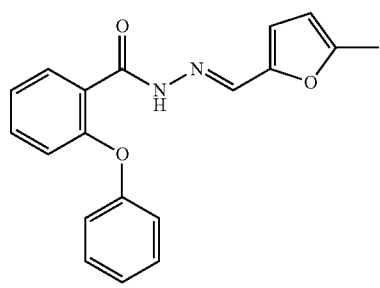<br>PNU74654 |

TABLE 2-continued
| Cmpd. No. | Structure |
|---|---|
| 8 | 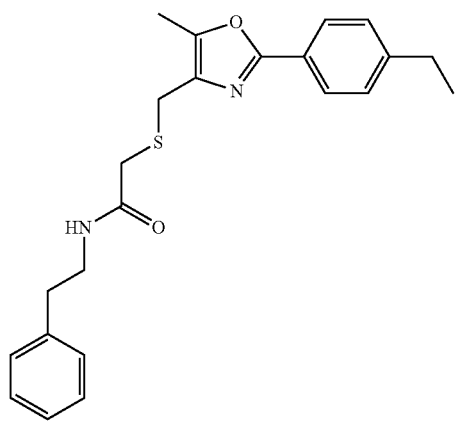<br>iCRT3 |
| 9 | 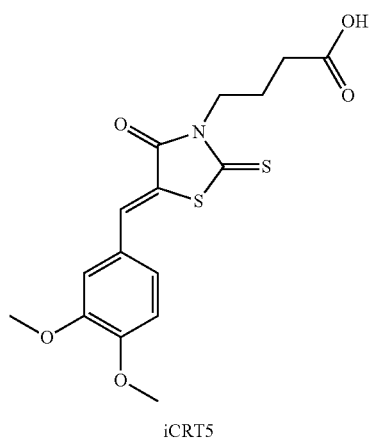 [SMILES: COc1ccc(/C=C2\SC(=S)N(CCCC(=O)O)C2=O)cc1OC]<br>iCRT5 |
| 10 | 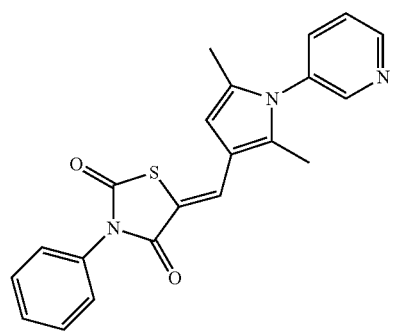<br>iCRT14 |

TABLE 2-continued

| Cmpd. No. | Structure |
|---|---|
| 11 | BC21 |
| 12 | aStAx-35: AcRRWPQS5ILDS5HVRRVWR—NH2 |
| 13 | UU-T01 |
| 14 | UU-T02 |

TABLE 2-continued
| Cmpd. No. | Structure |
|---|---|
| 15 | 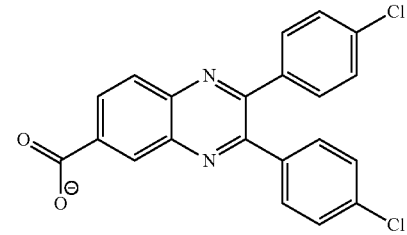\nR999636[60] |
| 16 | 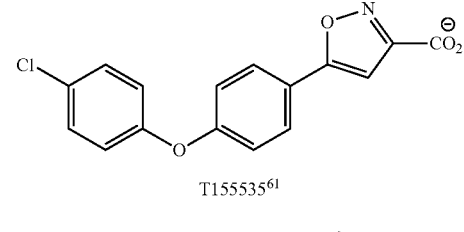\nT155535[61] |
| 17 | 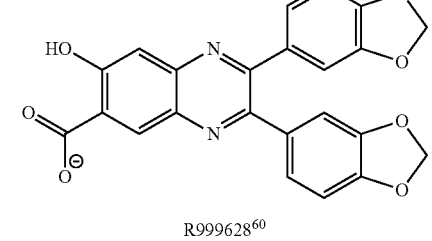\nR999628[60] |
| 18 | 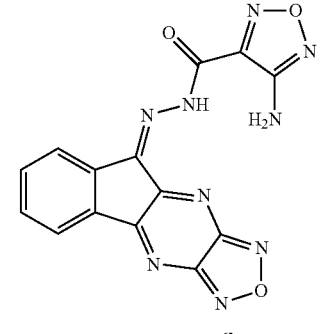\nZINC02092166[62] |
| 19A | 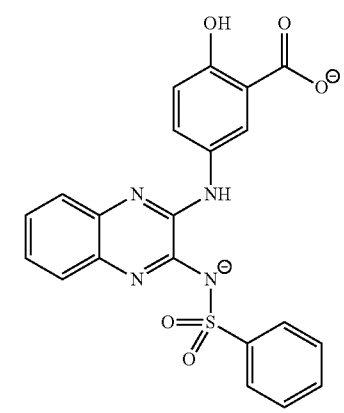\nZINC20828864[63] |

TABLE 2-continued

| Cmpd. No. | Structure |
|---|---|
| 19B | 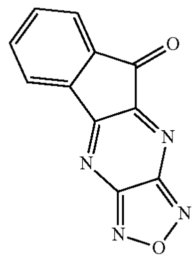 [SMILES: O=C1c2ccccc2-c2nc3nonc3nc21] |
| 20 | 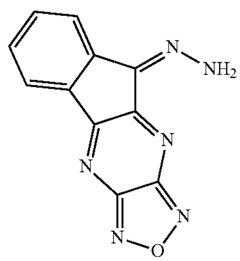 [SMILES: N/N=C1/c2ccccc2-c2nc3nonc3nc21] |
| 21 | UZI2587998[62] |
| 22 | R396133[78] |
| 23 | CDS018522[78] |

TABLE 2-continued
| Cmpd. No. | Structure |
|---|---|
| 24 | 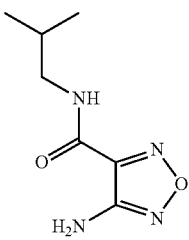CDS006174[78] |
| 25 | 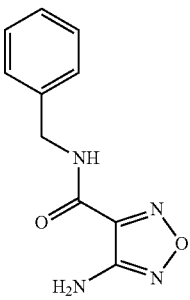CDS018901[78] |
| 26 | 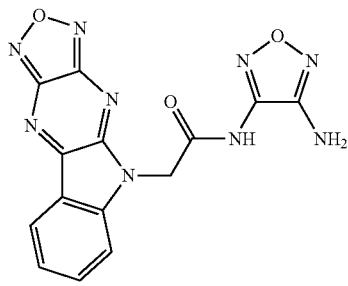 |
| 27 | 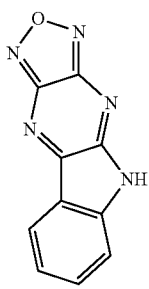 |
| 28 | 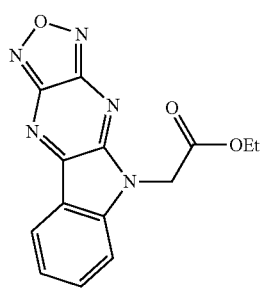 |

TABLE 2-continued
| Cmpd. No. | Structure |
|---|---|
| 29 | 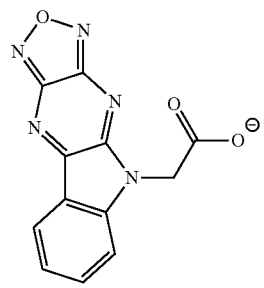 [SMILES: O=C([O-])Cn1c2ccccc2c2nc3nonc3nc21] |
| 30 | 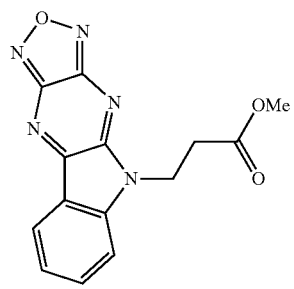 [SMILES: COC(=O)CCn1c2ccccc2c2nc3nonc3nc21] |
| 31 | 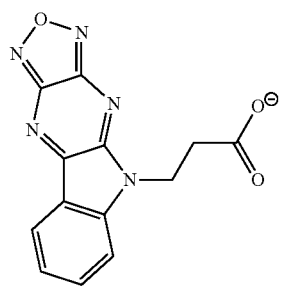 [SMILES: O=C([O-])CCn1c2ccccc2c2nc3nonc3nc21] |
| 32 | 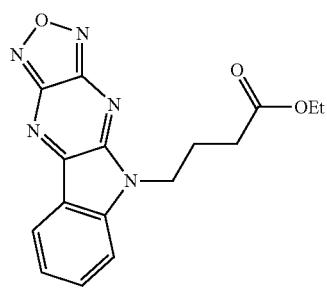 [SMILES: CCOC(=O)CCCn1c2ccccc2c2nc3nonc3nc21] |
| 33 | 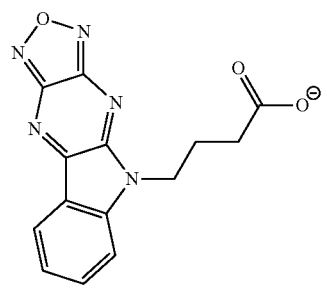 [SMILES: O=C([O-])CCCn1c2ccccc2c2nc3nonc3nc21] |

TABLE 2-continued
| Cmpd. No. | Structure |
|---|---|
| 34 | 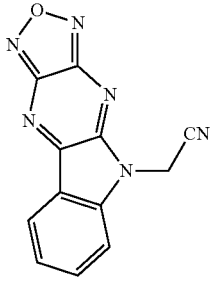 [SMILES: N#CCn1c2ccccc2c2nc3nonc3nc21] |
| 35 | 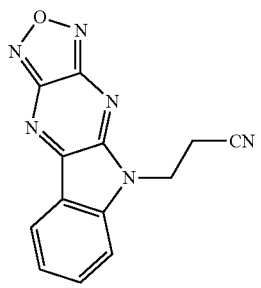 [SMILES: N#CCCn1c2ccccc2c2nc3nonc3nc21] |
| 36 | 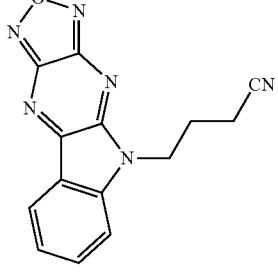 |
| 37 | 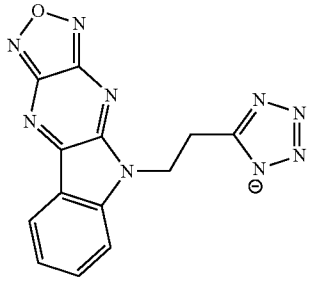 [SMILES: c1ccc2c(c1)c1nc3nonc3nc1n2CCc1nnn[n-]1] |
| 38 | 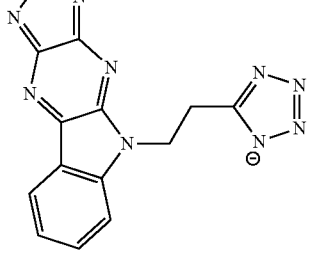 |

TABLE 2-continued

| Cmpd. No. | Structure |
|---|---|
| 39 | 9-methyl-substituted furazano-pyrazino-indole with N-CH₂CH₂CN |
| 40 | 9-bromo-substituted furazano-pyrazino-indole with N-CH₂CH₂CN |
| 41 | 8-bromo-substituted furazano-pyrazino-indole with N-CH₂CH₂CN |

4. MTs Cell Viability Assay

Colorectal cancer cell lines, SW480, HT29, an HCT116, and human normal cell line HEK293 were seeded in 96-well plates at $4 \times 10^3$ cells/well, maintained overnight at 37° C., and incubated with the tested compounds at various concentrations. Cell viability was monitored after 72 h using a freshly prepared mixture of 1 part phenazine methosulfate (PMS, Sigma) solution (0.92 mg/mL) and 19 parts 3-(4,5-dimethylthiazol-2-yl)-5-(3-carboxymethoxyphenyl)-2-(4-sulfophenyl)-2H-tetrazolium (MTs, Promega) solution (2 mg/mL). Cells were incubated in 10 μL of this solution at 37° C. for 3 h, and $A_{490}$ was measured. The effect of each compound is expressed as the concentration required to reduce $A_{490}$ by 50% ($IC_{50}$) relative to DMSO-treated cells. Experiments were performed in triplicate.

5. Cell Transfection and Luciferase Assay

FuGENE 6 (E2962, Promega) in a 96-well plate format was used for the transfection of HEK293 and SW480 cells according to the manufacturer's instructions. HEK293 cells were co-transfected with 45 ng of the TOPFlash or FOP-Flash reporter gene, 135 ng pcDNA3.1-β-catenin and 20 ng pCMV-RL normalization reporter gene. SW480 cells were co-transfected with 60 ng of the TOPFlash or FOPFlash reporter gene and 40 ng pCMV-RL normalization reporter. Cells were cultured in DMEM and 10% fatal bovine serum at 37° C. for 24 h, and different concentrations of inhibitors were then added. After 24 h, the luciferase reporter activity was measured using the Dual-Glo system (E2940, Promega). Normalized luciferase activity in response to the treatment with the inhibitors was compared with that obtained from the cells treated with DMSO. Experiments were performed in triplicate.

6. Quantitative Real Time PCR Analysis

SW480 cells at $1 \times 10^6$/mL were treated with different concentrations of the tested compounds for 24 h. Total RNAs were extracted with TRIzol (Ser. No. 15/596,026, Life Technologies), and the cDNA was synthesized with the superscript III first-strand kit (18080-051, Invitrogen). Quantitative real time PCR was performed using the iQ™ SYBR green supermix kit (170-8880, BIO-RAD) on an iQ⁵ multicolor real-time PCR reaction system (BIO-RAD). The threshold cycle ($C_T$) values were normalized to that of internal reference GAPDH. The primer pairs for human GAPDH were forward: 5'-GAAGGTGAAGGTCG-GAGTC-3' and reverse: 5'-GAAGATGGT-GATGGGATTTC-3'; for human HPRT forward: 5'-GC-TATAAATTCTTTGCTGACCTGCTG-3' and reverse: 5'-AATTACTTTTATGTCCCCTGTTGACTGG-3'; for human AXIN2 forward: 5'-AGTGTGAGGTCCACG-GAAAC-3' and reverse: 5'-CTTCACACTGCGATG-CATTT-3'; for human c-myc forward: 5'-CTTCTCTC-CGTCCTCGGATTCT-3' and reverse: 5'-GAAGGTGATCCAGACTCTGACCTT-3'; and for human cyclin D1 forward: 5'-ACAAACAGATCATCCG- CAAACAC-3' and reverse: 5'-TGTTGGGGCTCCTCAG-GTTC-3'. Experiments were performed in triplicate.

7. Western Blotting

SW480 cells at 1×10⁶ cells/mL were treated with different concentrations of 18 for 24 h. Cell were lysed in a buffer containing 50 mM Tris (pH 7.4), 150 mM NaCl, 1% Nonidet P-40, 0.5% sodium deoxycholate, 0.1% SDS, and protease inhibitors. After centrifugation at 12,000 rpm for 20 min at 4° C., the supernatant was loaded onto an 8% SDS polyacrylamide gel for electrophoretic analysis. Separated proteins were transferred onto nitrocellulose membranes for immunoblot analysis. The antibodies against c-myc (D84C12, Cell Signaling), cyclin D1 (sc-853, Santa Cruz Biotechnology, Inc.), and β-tubulin (sc-55529, Santa Cruz Biotechnology, Inc) were used. IRDye 680LT goat anti-mouse IgG (827-11080, LiCOR) or IRDye 800CW goat anti-rabbit IgG (827-08365, LiCOR) was used as the secondary antibody. The images were detected by the Odyssey Infrared Imaging System (LiCOR). The Western blot bands were quantified by LI-COR Image Studio Lite 4.0. Experiments were performed in duplicate.

8. Coimmunoprecipitation Assay

SW480 cells at 1×10⁶/mL were treated with different concentrations of 18 for 24 h. Cells were lysed in buffer containing 50 mM Tris, pH 7.4, 150 mM NaCl, 1% Nonidet P-40, 2 mM EDTA, and protease inhibitors. The lysates were preabsorbed to A/G plus agarose (sc-2003, Santa Cruz Biotechnology, Inc.) at 4° C. for 1 h. Preadsorbed lysates were incubated with a specific primary antibody overnight at 4° C. A/G plus agarose was then added to the lysates mixture and incubated for 3 h. The beads were washed 5 times with the lysis buffer at 4° C. The bound protein was eluted by boiling in the SDS sample buffer and loaded onto 8% SDS polyacrylamide gel for electrophoretic analysis. Separated proteins were transferred onto nitrocellulose membranes for immunoblot analysis. The primary antibodies were against fl-catenin (610153, BD Biosciences) and Tcf4 (05-511, Millipore). IRDye 680LT goat anti-mouse IgG (827-11080, LiCOR) was used as the secondary antibody. The images were detected by the Odyssey Infrared Imaging System (LiCOR). Experiments were performed in duplicate.

9. Ligand Docking Using Autodock Vina

Autodock Vina was used for the initial blind docking of 18. Exhaustiveness was increased to 12 (exhaustiveness=12), and 18 ligand conformations (num_modes=18) were generated for each binding region. All other parameters were left as default values.

10. Ligand Docking Using Glide 5.8

The 3-D coordinates of all ligands were generated by Schrodinger LigPrep with Epik to expand the protonation and tautomeric states at pH=7.0. The energy minimization was then applied to all ligands with the OPLS_2005 force field and the GB/SA water solvation condition. The partial charges of the ligands were calculated with the OPLS_2005 force field. The grid box was defined to include all the residues in the Tcf4 G[13]ANDE[17] binding site (Huang et al. (2014) ACS Chem. Biol. 9, 193-201). The default parameters were used in receptor grid generation. The standard precision mode was used in ligand docking. The ligand scaling factor was set to 0.5 for the atoms with the partial charges lower than 0.15. The number of poses per ligand for the initial phase of docking was increased to 10,000. The 1,000 best poses per ligand were kept for energy minimization with a maximum number of the minimization steps of 5,000. A maximum of 100,000 ligand poses per docking run and 50 poses per ligand were collected. Up to 100 poses per ligand were kept for the post-docking minimization. The default settings were used for the remaining parameters.

11. Ligand Docking Using Autodock 4.2

The partial atomic charges were calculated using the Gasteiger-Marsili method. The rotatable bonds in the ligands were defined using AutoTors, which also united the nonpolar hydrogens and partial atomic charges to the bonded carbon atoms. The grid maps were calculated using AutoGrid. The AutoDock area was defined to include all the residues of the Tcf4 G[13]ANDE[17] binding site, and the grid spacing was set to 0.375 Å. Docking was performed using the Lamarckian genetic algorithm, and the pseudo-Solis and Wets method was applied for the local search. Each docking experiment was performed 100 times, yielding 100 docked conformations. The other settings were the default parameters. All of the ligands followed the same docking protocol. The results of the docking experiments were evaluated by the auxiliary clustering analysis and the visual inspection.

12. Synthesis of (Z)-9-Hydrazono-9H-Indeno[1,2-B][1,2,5]Oxadiazolo[3,4-E]Pyrazine (Compound 20)

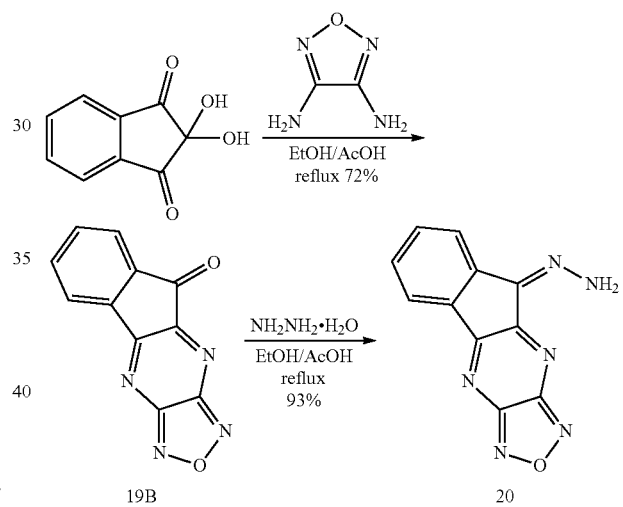

A. Preparation of 9H-Indeno[1,2-B][1,2,5]Oxadiazolo[3,4-E]Pyrazin-9-One (Compound 19B)

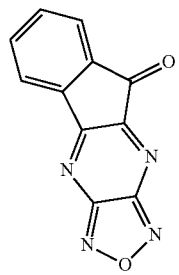 [SMILES: O=C1c2ccccc2-c2nc3nonc3nc21]

To a solution of ninhydrin (0.32 g, 1.80 mmol) in a solvent mixture (ethanol:glacial acid=1:1, 10 mL) was added 1,2,5-oxadiazole-3,4-diamine (0.18 g, 1.80 mmol). After stirring for 18 h at room temperature, the mixture was heated to gentle reflux for another 6 h. It was then cooled to room temperature, and the resulting precipitate was filtered and washed with water to yield 19B as pale yellow solid (0.29 g, 72% yield). $^1$H NMR (300 MHz, d$^6$-DMSO) δ ppm 8.31 (d, J=7.2 Hz, 1H), 8.18-8.02 (m, 2H), 7.97 (d, J=7.2 Hz, 1H); $^{13}$C NMR (125 MHz, dc-DMSO) δ ppm 189.55, 161.70, 140.01, 139.95, 138.69, 136.52, 126.06; HRMS (ESI) Calcd for C$_{11}$H$_4$N$_4$O$_2$(M+Na)$^+$ 247.0232, found 247.0230.

b. Preparation of (Z)-9-Hydrazono-9H-Indeno[1,2-B][1,2,5]Oxadiazolo[3,4-E]Pyrazine (Compound 20)

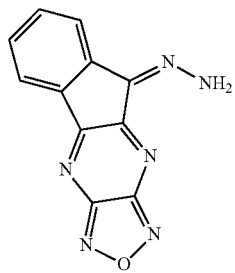 [SMILES: N/N=C1/c2ccccc2-c2nc3nonc3nc21]

To a solution of 19B (0.15 g, 0.67 mmol) in a mixture of ethanol and glacial acid (10 mL, 1:1) was added hydrazine hydrate (0.33 g, 6.70 mmol). The mixture was heated to gentle reflux for 2 h, and then cooled to room temperature. The resulting precipitate was filtered and washed with water to afford 20 as red solid (0.14 g, 93% yield). $^1$H NMR (300 MHz, d$^6$-DMSO) δ ppm 10.48 (d, J=13.8 Hz, 1H), 10.40 (d, J=13.8 Hz, 1H), 8.07 (d, J=7.5 Hz, 1H), 7.73-7.66 (m, 2H), 7.46 (t, J=7.5 Hz, 1H); $^{13}$C NMR (75 MHz, d$^6$-DMSO) δ ppm 161.75, 155.02, 152.69, 152.51, 144.75, 135.86, 129.81, 128.86, 128.48, 124.66, 119.65; HRMS (ESI) Calcd for C$_{11}$H$_6$N$_6$O (M–H)$^-$ 237.0525, found 237.0531.

13. Synthesis of (Z)-4-Amino-N'-(9H-Indeno[1,2-B][1,2,5]Oxadiazolo[3,4-E]Pyrazin-9-ylidene)-1,2,5-Oxadiazole-3-Carbohydrazide (Compound 18)

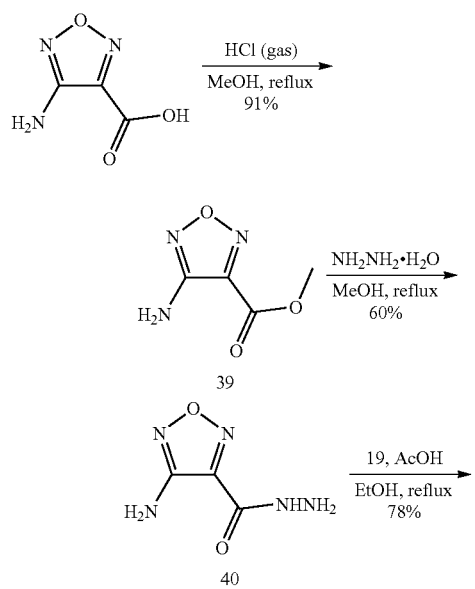

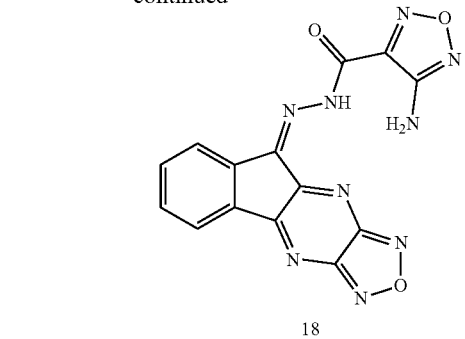

A. Preparation of 4-Amino-1,2,5-Oxadiazole-3-Carbohydrazide (Compound 40)

To a solution of 4-amino-1,2,5-oxadiazole-3-carboxylic acid (0.50 g, 3.87 mmol) in methanol (30 mL) was bubbled with HCl (gas). The mixture was heated to gentle reflux for 8 h. Methanol was then removed under vacuum to give the crude product as pale yellow oil. To this residue was added diethyl ether (30 mL) and stirred for 30 min. The resulting precipitate was filtered to give desired product 39 (0.50 g, 91% yield) as white solid. It was used directly in next step without further purification. To a solution of 39 (0.15 g, 1.05 mmol) in methanol (10 mL), was added hydrazine hydrate (0.08 g, 1.57 mmol), the mixture was heated to gentle reflux. After 15 h, the solvent was removed completely under vacuum to give 40 (0.09 g, 60% yield) as white solid. $^1$H NMR (500 MHz, d$^6$-acetone) δ ppm 9.50 (brs, 1H), 5.76 (s, 2H), 4.50 (brs, 2H); $^{13}$C NMR (125 MHz, d$^6$-acetone) δ ppm 157.02, 156.06, 140.00; HRMS (ESI) Calcd for C$_3$H$_5$N$_5$O$_2$ (M+H)$^+$ 144.0516, found 144.0519.

b. Preparation of (Z)-4-Amino-N'-(9H-Indeno[1,2-B][1,2,5]Oxadiazolo[3,4-E]Pyrazin-9-ylidene)-1,2,5-Oxadiazole-3-Carbohydrazide (Compound 18)

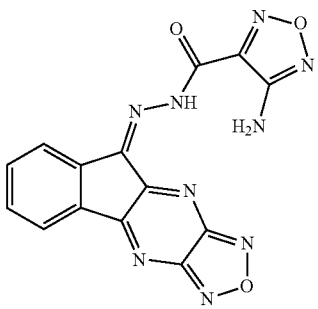 [SMILES: Nc1nonc1C(=O)N/N=C1/c2ccccc2-c2nc3nonc3nc21]

To a solution of 19 (0.05 g, 0.22 mmol) in ethanol (10 mL) was added 40 (0.03 g, 0.22 mmol) and glacial acid (1 mL). The reaction mixture was heated to gentle reflux overnight and then poured into ice water. The resulting precipitate was filtered and washed with water to give 18 as yellow solid (0.06 g, 78% yield). $^1$H NMR (500 MHz, d$^6$-DMSO) δ ppm 13.55 (brs, 1H), 8.26 (d, J=7.5 Hz, 1H), 8.06 (d, J=7.0 Hz, 1H), 7.92 (t, J=7.5 Hz, 1H), 7.82 (t, J=7.0 Hz, 1H), 6.01 (s, 2H); $^{13}$C NMR (125 MHz, d$^6$-DMSO) δ ppm 162.75, 158.62, 157.14, 155.38, 153.17, 152.29, 152.04, 144.32, 140.35, 136.76, 134.59, 133.67, 125.23, 122.82; HRMS (ESI) Calcd for $C_{14}H_7N_9O_3$(M−H)$^-$ 348.0594, found 348.0604.

14. Synthesis of 2-(5H-[1,2,5]Oxadiazolo[3',4':5,6]Pyrazino[2,3-B]Indol-5-yl)-N-(4-Amino-1,2,5-Oxadiazol-3-yl)Acetamide (Compound 26)

A. Preparation of 5H-[1,2,5]Oxadiazolo[3',4':5,6]Pyrazino[2,3-B]Indole (Compound 27)

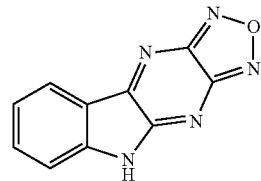 [SMILES: c1ccc2c(c1)[nH]c1nc3nonc3nc12]

To a solution of isatin (0.20 g, 1.36 mmol) in glacial acid (5 mL) was added 1,2,5-oxadiazole-3,4-diamine (0.14 g, 1.36 mmol). The resulting mixture was heated to gentle reflux for 15 h and then poured into ice water. The resulting precipitate was filtered and washed with water to afford 27 as red solid (0.05 g, 17% yield). $^1$H NMR (300 MHz, d$^6$-DMSO) δ ppm 12.35 (brs, 1H), 8.19 (d, J=7.8 Hz, 1H), 7.73 (t, J=7.5 Hz, 1H), 7.39 (d, J=8.1 Hz, 1H), 7.32 (t, J=7.2 Hz, 1H); $^{13}$C NMR (75 MHz, d$^6$-DMSO) δ ppm 153.96, 152.62, 152.50, 151.93, 148.81, 136.37, 125.33, 123.11, 118.86, 113.38; HRMS (ESI) Calcd for $C_{10}H_5N_5O$ (M−H)$^-$ 210.0416, found 210.0427.

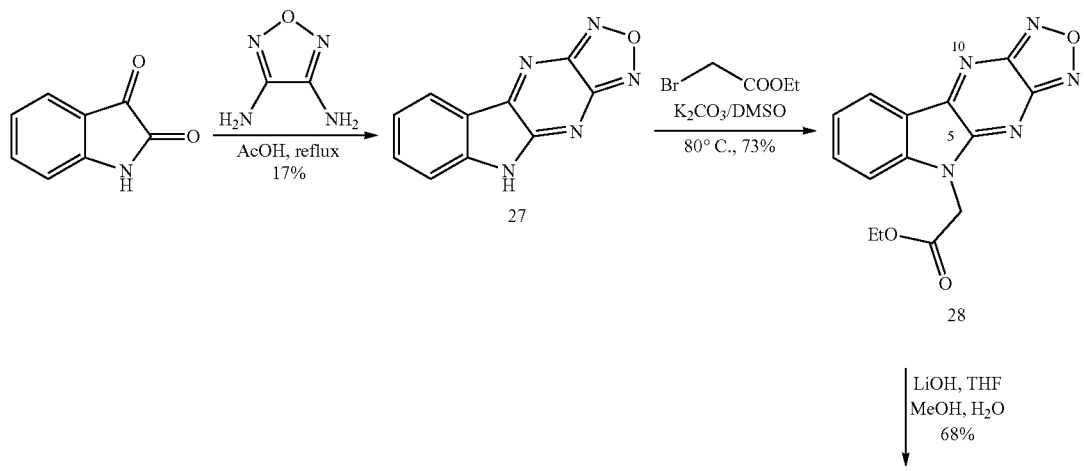

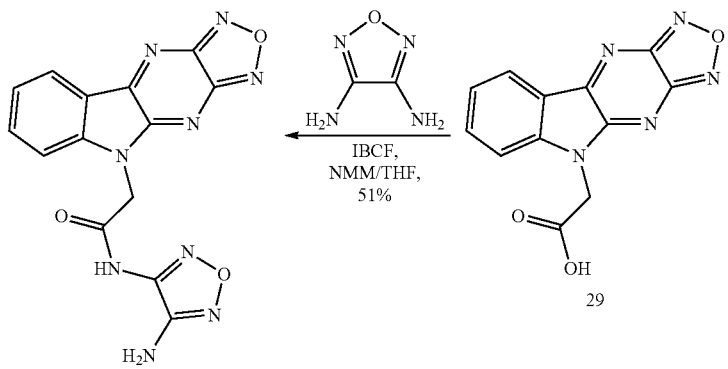

b. Preparation of Ethyl-2-(5H-[1,2,5]Oxadiazolo[3',4':5,6]Pyrazino[2,3-B]Indol-5-yl)Acetate (Compound 28)

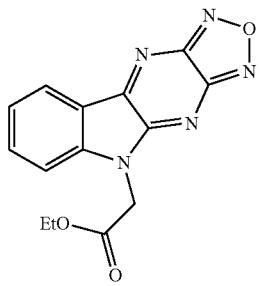 [SMILES: CCOC(=O)Cn1c2ccccc2c2nc3nonc3nc21]

To a solution of 27 (0.08 g, 0.38 mmol) and ethyl 2-bromoacetate (0.09 g, 0.57 mmol) in DMSO (10 mL) was added $K_2CO_3$ (0.08 g, 0.57 mmol). The resulting mixture was heated to 80° C. overnight. After 15 h, the reaction mixture was cooled to room temperature and diluted with ethyl acetate (80 mL), washed with brine (20 mL×3), dried over $Na_2SO_4$, filtered, and concentrated. The residue was purified by column chromatography (silica gel, hexanes:acetone=5:1) to afford 28 (0.08 g, 73% yield) as red solid. $^1$H NMR (500 MHz, d$^6$-DMSO) δ ppm 8.28 (d, J=7.5 Hz, 1H), 7.85 (t, J=7.0 Hz, 1H), 7.69 (d, J=8.5 Hz, 1H), 7.42 (t, J=7.5 Hz, 1H), 5.22 (s 2H), 4.18 (q, J=7.0 Hz, 2H), 1.21 (t, J=7.0 Hz, 3H); $^{13}$C NMR (125 MHz, d$^6$-DMSO) δ ppm 167.98, 153.15, 152.32, 152.07, 151.64, 148.92, 136.50, 125.30, 124.05, 118.50, 112.39, 62.25, 43.35, 14.70; HRMS (ESI) Calcd for $C_{14}H_{11}N_5O_3$ (M+Na)$^+$ 320.0760, found 320.0759.

c. Preparation of 2-(5H-[1,2,5]Oxadiazolo[3',4':5,6]Pyrazino[2,3-B]Indol-5-yl)Acetic Acid (Compound 29)

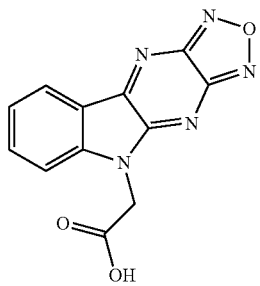 [SMILES: O=C(O)Cn1c2ccccc2c2nc3nonc3nc21]

To a solution of 28 (0.08 g, 0.27 mmol) in a solvent mixture (14 mL, THF:MeOH:$H_2O$=4:2:1) was added LiOH (0.05 g, 2.15 mmol). The mixture was stirred for 8 h at room temperature. Then, the pH value was adjusted to 4-5 with HCl (1 M), diluted with water (50 mL), and extracted with ethyl acetate (20 mL×3). The combined organic phase was dried over $Na_2SO_4$ and concentrated to give 29 (0.05 g, 68%) as orange solid. $^1$H NMR (500 MHz, d$^6$-DMSO) δ ppm 13.36 (brs, 1H), 8.28 (d, J=8.0 Hz, 1H), 7.84 (t, J=8.0 Hz, 1H), 7.69 (d, J=8.0 Hz, 1H), 7.41 (t, J=8.0 Hz, 1H), 5.10 (s, 2H); $^{13}$C NMR (125 MHz, d$^6$-DMSO) δ ppm 169.34, 153.20, 153.00, 152.11, 151.63, 149.10, 136.51, 125.27, 123.95, 118.44, 112.38, 43.38; HRMS (ESI) Calcd for $C_{12}H_7N_5O_3$(M−H)$^-$ 268.0471, found 268.0485.

d. Preparation of 2-(5H-[1,2,5]Oxadiazolo[3',4':5,6]Pyrazino[2,3-B]Indol-5-yl)-N-(4-Amino-1,2,5-Oxadiazol-3-yl)Acetamide (Compound 26)

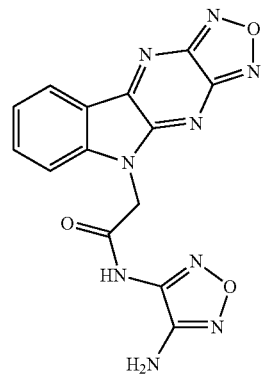 [SMILES: Nc1nonc1NC(=O)Cn1c2ccccc2c2nc3nonc3nc21]

To a solution of 29 (0.18 g, 0.67 mmol) and 4-methylmorpholine (0.14 g, 0.34 mmol) in THF (15 mL) was added isobutyl chloroformate (0.09 g, 0.67 mmol) at −15° C. The resulting mixture was stirred for 1 h at the same temperature. Then, 1,2,5-oxadiazole-3,4-diamine (0.10 g, 1.00 mmol) was added slowly. The temperature was allowed to rise to room temperature gradually and stirred for another 1 h. The mixture was diluted with ethyl acetate (80 mL), washed with brine (20 mL×3), dried over $Na_2SO_4$, filtrated, and concentrated. The residue was purified by column chromatography (silica gel, hexanes:acetone=2:1 to 1:1) to afford 26 (0.12 g, 51% yield) as orange solid. $^1$H NMR (500 MHz, d$^6$-DMSO) δ ppm 11.13 (brs, 1H), 8.32 (d, J=7.5 Hz, 1H), 7.87 (t, J=8.0 Hz, 1H), 7.73 (d, J=8.0 Hz, 1H), 7.45 (t, J=7.5 Hz, 1H), 6.04 (s, 2H), 5.29 (s, 2H); $^{13}$C NMR (125 MHz, d$^6$-DMSO) δ ppm 166.66, 153.50, 152.88, 152.36, 152.13, 151.96, 149.26, 144.25, 136.50, 125.26, 124.04, 118.69, 112.57, 44.85; HRMS (ESI) Calcd for $C_{14}H_9N_9O_3$(M−H)$^-$ 350.0750, found 350.0755.

15. Synthesis of 4-(5H-[1,2,5]Oxadiazolo[3',4':5,6]Pyrazino[2,3-B]Indol-5-yl)Butanoic Acid (Compound 33)

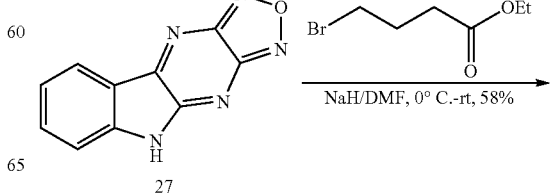

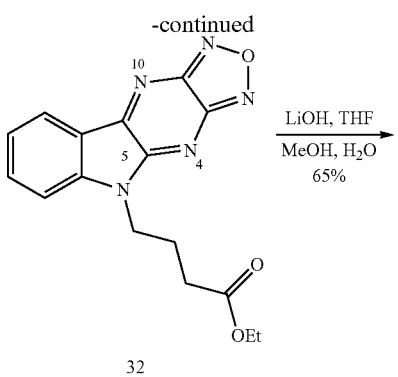

32

A. Preparation of Ethyl 4-(5H-[1,2,5]Oxadiazolo[3',4':5,6]Pyrazino[2,3-B]Indol-5-yl)Butanoate (Compound 32)

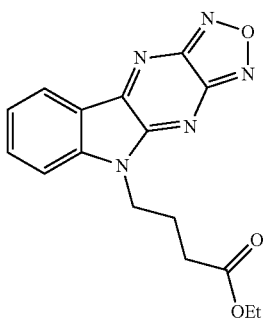 [SMILES: CCOC(=O)CCCn1c2ccccc2c2nc3nonc3nc21]

To a solution of 27 (0.017 g, 0.08 mmol) in DMF (5 mL) was added NaH (0.0030 g, 0.12 mmol) at 0° C. The resulting mixture was stirred for 0.5 h at 0° C. before adding ethyl 4-bromobutanoate (0.023 g, 0.12 mmol). The reaction solution was allowed to warm to room temperature gradually then stirred overnight. The mixture was diluted with ethyl acetate (50 mL), washed with brine (20 mL×3), dried over $Na_2SO_4$, filtrated, and concentrated. The residue was purified through column chromatography (silica gel, hexanes: acetone=3:1 to 1:1) to afford 32 as orange solid (0.010 g, yield 58%). $^1$H NMR (400 MHz, $CDCl_3$) δ ppm 8.20 (d, J=7.2 Hz, 1H), 7.71 (t, J=7.2 Hz, 1H), 7.42 (d, J=8.0 Hz, 1H), 7.31 (t, J=7.2 Hz, 1H), 4.32 (t, J=6.8 Hz, 2H), 4.07 (q, J=6.0 Hz, 2H), 2.43 (t, J=6.4 Hz, 2H), 2.20-2.12 (m, 2H) 1.19 (t, J=6.0 Hz, 3H); $^{13}$C NMR (100 MHz, $CDCl_3$) δ ppm 172.54, 151.80, 151.27, 151.19, 150.41, 147.98, 135.56, 125.06, 123.11, 118.23, 110.64, 60.71, 40.93, 30.94, 22.68, 14.12; HRMS (ESI) Calcd for $C_{16}H_{15}N_5O_3$ $(M+Na)^+$ 348.1073, found 348.1081.

A. Preparation of 4-(5H-[1,2,5]Oxadiazolo[3',4':5,6]Pyrazino[2,3-B]Indol-5-yl)Butanoic Acid (Compound 33)

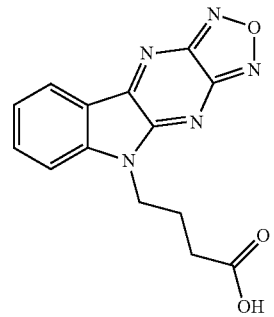 [SMILES: O=C(O)CCCn1c2ccccc2c2nc3nonc3nc21]

Compound 33 was prepared as described herein above for Compound 29 to afford an orange solid (yield 65%). $^1$H NMR (400 MHz, $d^6$-DMSO) δ ppm 12.08 (brs, 1H), 8.27 (d, J=7.6 Hz, 1H), 7.86 (t, J=8.0 Hz, 1H), 7.70 (d, J=8.0 Hz, 1H), 7.41 (t, J=7.2 Hz, 1H), 4.30 (t, J=6.8 Hz, 2H), 2.38 (t, J=7.2 Hz, 2H), 2.07-2.00 (m, 2H); $^{13}$C NMR (100 MHz, $d^6$-DMSO) δ ppm 174.38, 153.67, 152.21, 151.97, 148.78, 136.10, 125.11, 123.29, 118.60, 111.76, 109.99, 41.07, 31.23, 23.06; HRMS (ESI) Calcd for $C_{14}H_{11}N_5O_3$ $(M+Na)^+$ 320.0760, found 320.0761.

16. Synthesis of 3-(5H-[1,2,5]Oxadiazolo[3',4':5,6]Pyrazino[2,3-B]Indol-5-yl)Propanoic Acid (Compound 31)

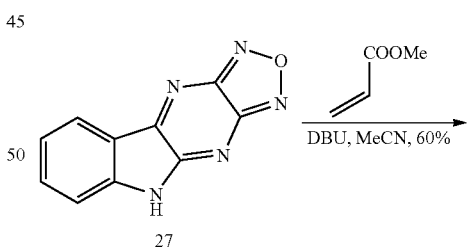

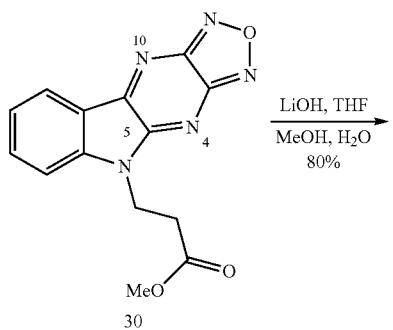

-continued

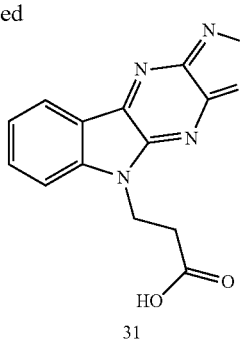

31

A. Preparation of Methyl 3-(5H-[1,2,5]Oxadiazolo[3',4':5,6]Pyrazino[2,3-B]Indol-5-yl)Propanoate (Compound 30)

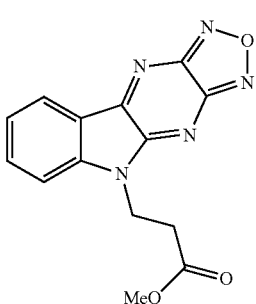 [SMILES: COC(=O)CCn1c2ccccc2c2nc3nonc3nc21]

To a solution of 27 (0.10 g, 0.47 mmol) in acetonitrile (15 mL) was added 1,8-diazabicyclo[5.4.0]undec-7-ene (DBU) (0.24 g, 1.57 mmol). The resulting mixture was stirred for 0.5 h before adding methyl acrylate (0.14 g, 1.57 mmol). The reaction solution was heated to 50° C. and stirred for another 24 h. It was then diluted with ethyl acetate (50 mL), washed with brine (20 mL×3), and dried over $Na_2SO_4$, filtrated, and concentrated. The residue was purified by column chromatography (silica gel, hexanes:acetone=3:1 to 1:1) to afford 30 as an orange solid (0.084 g, yield 60%). $^1$H NMR (400 MHz, $CDCl_3$) δ ppm 8.33 (d, J=7.6 Hz, 1H), 7.79 (t, J=8.4 Hz, 1H), 7.51 (d, J=8.4 Hz, 1H), 7.40 (t, J=7.6 Hz, 1H), 4.60 (t, J=6.8 Hz, 2H), 3.66 (s, 3H), 3.02 (t, J=6.8 Hz, 2H); $^{13}$C NMR (100 MHz, $CDCl_3$) δ ppm 171.27, 151.81, 151.39, 151.16, 150.42, 147.90, 135.48, 125.20, 123.25, 118.42, 110.81, 52.11, 37.90, 21.11; HRMS (ESI) Calcd for $C_{14}H_{11}N_5O_3$ (M+Na)$^+$ 320.0760, found 320.0760.

b. Preparation of 3-(5H-[1,2,5]Oxadiazolo[3',4':5,6]Pyrazino[2,3-B]Indol-5-yl)Propanoic Acid (Compound 31)

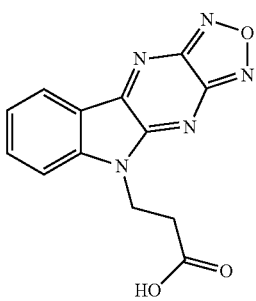 [SMILES: O=C(O)CCn1c2ccccc2c2nc3nonc3nc21]

Compound 31 was prepared as described herein above for Compound 29 to afford an orange solid (yield 80%). $^1$H NMR (400 MHz, d-DMSO) δ ppm 12.46 (brs, 1H), 8.26 (d, J=7.6 Hz, 1H), 7.85 (t, J=8.0 Hz, 1H), 7.76 (d, J=8.0 Hz, 1H), 7.40 (t, J=7.6 Hz, 1H), 4.48 (t, J=6.8 Hz, 2H), 2.83 (t, J=7.2 Hz, 2H); $^{13}$C NMR (100 MHz, d$^6$-DMSO) δ ppm 172.65, 153.56, 152.09, 151.96, 151.49, 148.66, 136.88, 124.99, 123.33, 118.52, 112.25, 32.10, 31.14; HRMS (ESI) Calcd for $C_{13}H_9N_5O_3$ (M+Na)$^+$ 306.0603, found 306.0612.

17. Synthesis of 2-(5H-[1,2,5]Oxadiazolo[3',4':5,6]Pyrazino[2,3-B]Indol-5-yl)Acetonitrile (Compound 34)

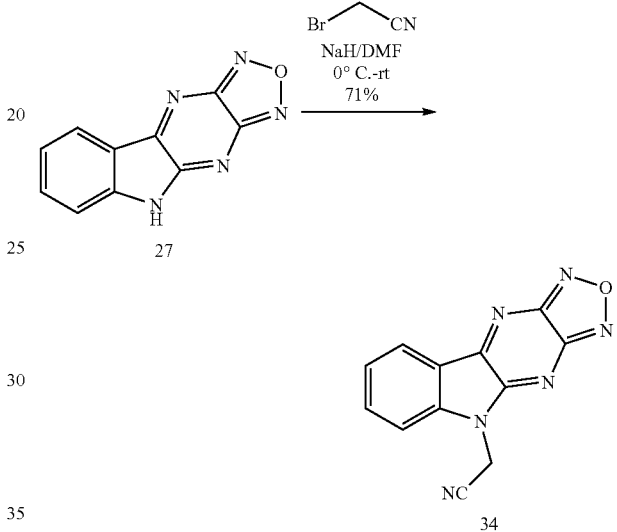

A. Preparation of 2-(5H-[1,2,5]Oxadiazolo[3',4':5,6]Pyrazino[2,3-B]Indol-5-yl)Acetonitrile (Compound 34)

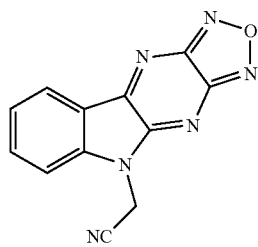 [SMILES: N#CCn1c2ccccc2c2nc3nonc3nc21]

To a solution of 27 (0.03 g, 0.14 mmol) in DMF (10 mL) was added NaH (60%) (0.007 g, 0.17 mmol) at 0° C. The resulting mixture was stirred for 0.5 h at the same temperature before 2-bromoacetonitrile (0.02 g, 0.17 mmol) was added into. It was then allowed to warm to room temperature gradually and stirred for another 1 h. The reaction mixture was then quenched with water (30 mL) and diluted with ethyl acetate (60 mL). The organic phase was washed with brine (20 mL×2), dried over $Na_2SO_4$, and concentrated. The residue was purified by column chromatography (silica gel, hexanes:acetone=5:1) to afford 34 (0.025 g, 71% yield) as a yellow solid. $^1$H NMR (500 MHz, d$^6$-acetone) δ ppm 8.37 (d, J=8.0 Hz, 1H), 7.97 (t, J=8.5 Hz, 1H), 7.85 (d, J=8.5 Hz, 1H), 7.56 (t, J=8.0 Hz, 1H), 5.51 (s 2H); $^{13}$C NMR (125

MHz, d⁶-acetone) δ ppm 152.75, 152.33, 151.73, 151.12, 147.17, 135.97, 125.04, 124.21, 119.23, 114.31, 111.31, 29.44; HRMS (ESI) Calcd for $C_{12}H_6N_6O$ $(M+Na)^+$ 273.0501, found 273.0508.

18. Synthesis of 5-(2-(2H-Tetrazol-5-yl)Ethyl)-5H-[1,2,5]Oxadiazolo[3',4':5,6]Pyrazino[2,3-B]Indole (Compound 37)

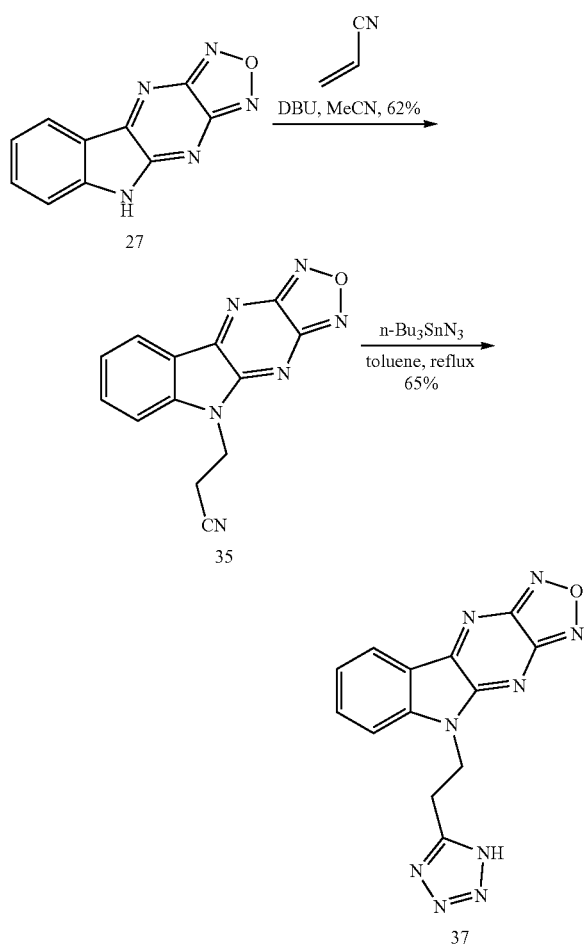

A. Preparation of 3-(5H-[1,2,5]Oxadiazolo[3',4':5,6]Pyrazino[2,3-B]Indol-5-yl)Propanenitrile (Compound 35)

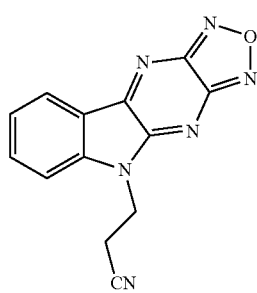 [SMILES: N#CCCn1c2ccccc2c2nc3nonc3nc21]

To a solution of 27 (0.20 g, 0.95 mmol) in acetonitrile (10 mL), DBU (0.072 g, 0.47 mmol) was added. The solution was stirred for 0.5 h. Then, acrylonitrile (0.075 g, 1.4 mmol) was added. The reaction solution was heated to 50° C. and stirred for 24 h. It was then diluted with ethyl acetate (50 mL), washed with brine (20 mL×3), and dried over $Na_2SO_4$, filtrated, and concentrated. The residue was purified by column chromatography (silica gel, hexanes:acetone=5:1 to 1:1) to afford 35 as orange solid (yield 62%). ¹H NMR (400 MHz, d⁶-DMSO) δ ppm 8.28 (d, J=7.6 Hz, 1H), 7.89-7.84 (m, 2H), 7.42 (t, J=7.2 Hz, 1H), 4.61 (t, J=6.8 Hz, 2H), 3.10 (t, J=6.4 Hz, 2H); ¹³C NMR (100 MHz, d⁶-DMSO) δ ppm 153.39, 152.02, 151.94, 151.51, 148.27, 136.17, 125.11, 123.69, 119.10, 118.51, 112.17, 37.66, 16.43; HRMS (ESI) Calcd for $C_{13}H_8N_6O$ $(M+Na)^+$ 287.0657, found 287.0661.

b. Preparation of 5-(2-(2H-Tetrazol-5-yl)Ethyl)-5H-[1,2,5]Oxadiazolo[3',4':5,6]Pyrazino[2,3-B]Indole (Compound 37)

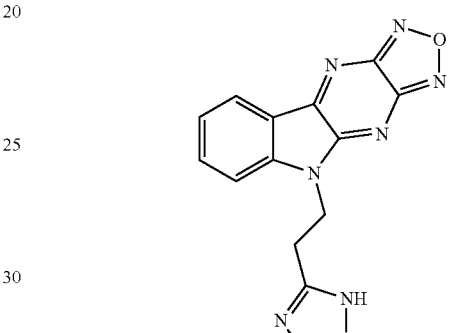

To a solution of 35 (0.02 g, 0.076 mmol) in toluene (10 mL) was added nBu₃SnN₃ (0.13 g, 0.38 mmol). The resulting mixture was heated to reflux for 48 h. It was then cooled to room temperature, and the pH value was adjusted to 4-5 with HCl (1 M) and diluted with ethyl acetate (60 mL). The organic phase was washed with brine (20 mL×2), dried over $Na_2SO_4$, and concentrated. The residue was purified by column chromatography (silica gel, $CH_2Cl_2$:MeOH=10:1 to 5:1) to afford 37 (15.00 mg, 65% yield) as a red solid. ¹H NMR (500 MHz, d⁶-DMSO) δ ppm 8.28 (d, J=7.8 Hz, 1H), 7.81 (t, J=8.1 Hz, 1H), 7.58 (d, J=8.0 Hz, 1H), 7.39 (t, J=7.8 Hz, 1H), 4.66 (t, J=6.6 Hz, 2H), 3.46 (t, J=6.6 Hz, 2H); ¹³C NMR (125 MHz, d⁶-DMSO) δ ppm 154.29, 153.81, 152.22, 152.17, 151.79, 148.66, 136.36, 125.33, 123.69, 118.74, 111.92, 40.36, 22.30; HRMS (ESI) Calcd for $C_{13}H_9N_9O$ $(M-H)^-$ 306.0852, found 306.0871.

19. Synthesis of 5-(3-(2H-Tetrazol-5-yl)Propyl)-5H-[1,2,5]Oxadiazolo[3',4':5,6]Pyrazino[2,3-B]Indole (Compound 38)

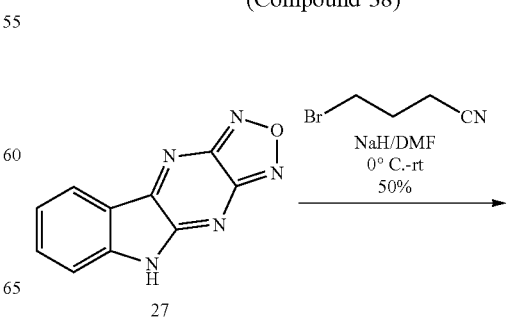

-continued

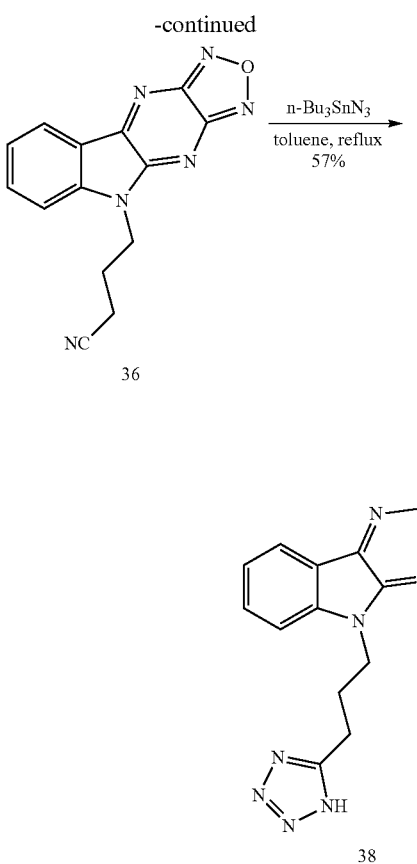

36

38

A. Preparation of 4-(5H-[1,2,5]Oxadiazolo[3',4':5,6]Pyrazino[2,3-B]Indol-5-yl)Butanenitrile (Compound 36)

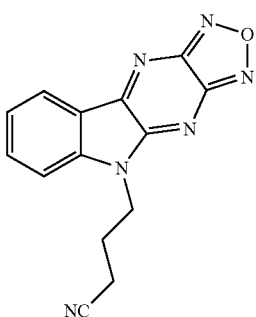 [SMILES: N#CCCCn1c2ccccc2c2nc3nonc3nc21]

Compound 36 was prepared as described herein above for Compound 34 to afford an orange solid (yield 50%). $^1$H NMR (400 MHz, d$^6$-DMSO) δ ppm 7.61-7.64 (m, 2H), 7.16 (t, J=7.6 Hz, 1H), 6.97 (d, J=8.0 Hz, 1H), 3.87 (t, J=7.2 Hz, 2H), 2.48 (t, J=7.2 Hz, 2H), 2.11-2.07 (m, 2H); $^{13}$C NMR (100 MHz, d$^6$-DMSO) δ ppm 158.41, 150.19, 138.62, 125.81, 124.16, 118.61, 117.73, 109.77, 38.85, 23.49, 15.02; HRMS (ESI) Calcd for $C_{14}H_{10}N_6O$ (M+Na)$^+$ 301.0814, found 301.0808.

b. Preparation of 5-(3-(2H-Tetrazol-5-yl)Propyl)-5H-[1,2,5]Oxadiazolo[3',4':5,6]Pyrazino[2,3-B]Indole (Compound 38)

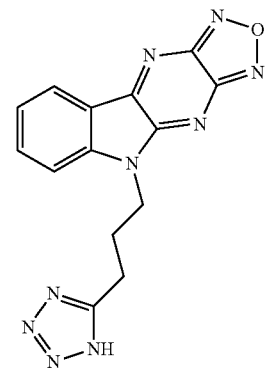 [SMILES: c1ccc2c(c1)c1nc3nonc3nc1n2CCCc1nnn[nH]1]

Red solid, yield 57%. $^1$H NMR (500 MHz, d$^6$-DMSO) δ ppm 8.26 (d, J=8.0 Hz, 1H), 7.85 (t, J=8.0 Hz, 1H), 7.72 (d, J=8.5 Hz, 1H), 7.40 (t, J=7.5 Hz, 1H), 4.40 (t, J=6.5 Hz, 2H), 3.02 (t, J=7.5 Hz, 2H), 2.32-2.26 (m, 2H); $^{13}$C NMR (125 MHz, d$^6$-DMSO) (ppm 153.81, 152.35, 152.18, 151.91, 148.92, 136.35, 125.32, 123.58, 118.82, 112.06, 41.32, 25.55, 21.10; HRMS (ESI) Calcd for $C_{14}H_{11}N_9O$ (M+Na)$^+$ 344.0984, found 344.0990.

20. Synthesis of Compounds 39-41

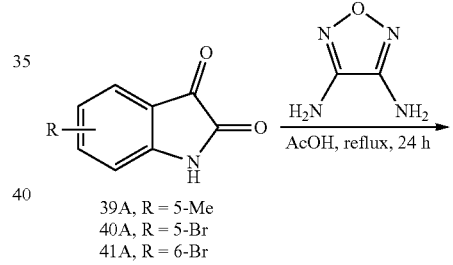

39A, R = 5-Me
40A, R = 5-Br
41A, R = 6-Br

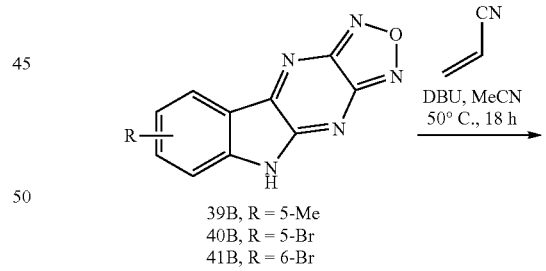

39B, R = 5-Me
40B, R = 5-Br
41B, R = 6-Br

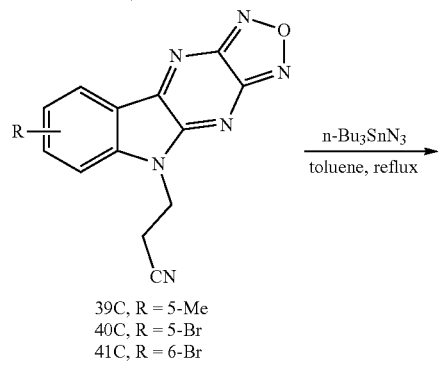

39C, R = 5-Me
40C, R = 5-Br
41C, R = 6-Br

-continued

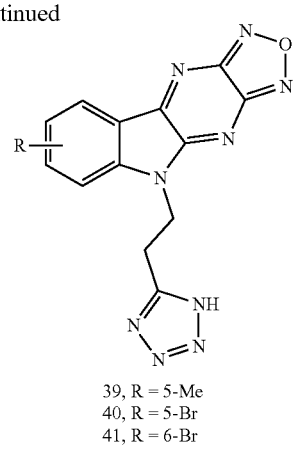

39, R = 5-Me
40, R = 5-Br
41, R = 6-Br

A. Preparation of 5-(2-(2H-Tetrazol-5-yl)Ethyl)-8-Methyl-5H-[1,2,5]Oxadiazolo[3',4':5,6]Pyrazino[2,3-B]Indole (Compound 39)

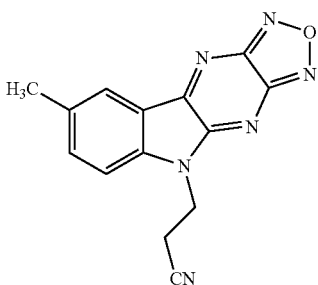 [SMILES: Cc1ccc2c(c1)c1nc3nonc3nc1n2CCC#N]

To a solution of 39C (0.020 g, 0.072 mmol) in toluene (10 mL) was added "Bu₃SnN₃ (0.12 g, 0.36 mmol). The resulting mixture was heated to reflux for 48 h. Then, it was cooled to room temperature, and the pH value was adjusted to 4-5 with HCl (1M), diluted with ethyl acetate (60 mL), and the organic phase was washed with brine (20 mL×2), then dried over Na₂SO₄ and concentrated. The residue was purified by column chromatography (silica gel, CH₂Cl₂:MeOH=10:1-5:1) to afford 39 (13.00 mg, 57% yield) as orange solid.

b. Preparation of 5-(2-(1H-Tetrazol-5-yl)Ethyl)-8-Bromo-5H-[1,2,5]Oxadiazolo[3',4':5,6]Pyrazino[2,3-B]Indole (Compound 40)

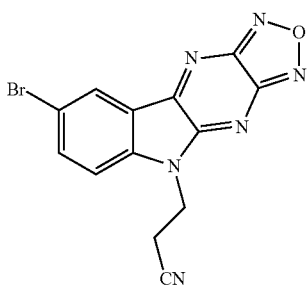 [SMILES: N#CCCn1c2ccc(Br)cc2c2nc3nonc3nc21]

Compound 40 was prepared as described above for compound 39. Overall yield 8% (3 steps).

c. Preparation of 5-(2-(2H-Tetrazol-5-yl)Ethyl)-7-Bromo-5H-[1,2,5]Oxadiazolo[3',4':5,6]Pyrazino[2,3-B]Indole (Compound 41)

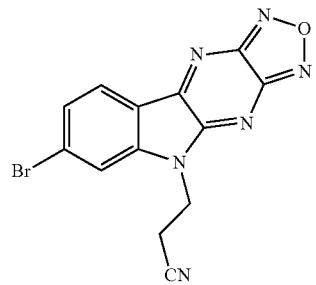 [SMILES: N#CCCn1c2cc(Br)ccc2c2nc3nonc3nc21]

Compound 41 was prepared as described above for compound 39. Overall yield 6% (3 steps).

21. HPLC Conditions

The purity of final compounds 18, 19B, 20, and 26-38 was determined by HPLC analysis. The instrument was an Agilent 1260 Infinity Quaternary LC with an Agilent 1260 Infinity ELSD detector. All of the tested compounds were dissolved in 20% DMSO for loading. The purity for all tested compounds was ≥90%.

Figure 2:
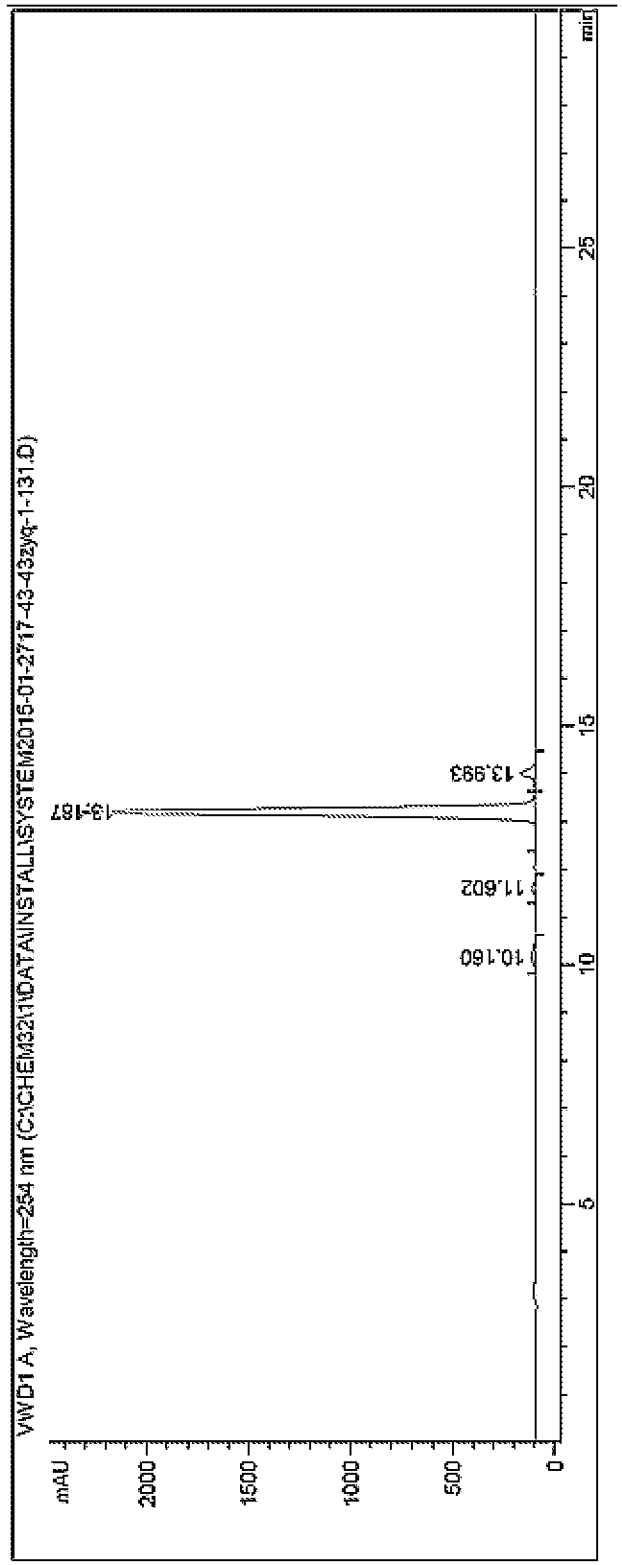
FIG. 2 shows a representative HPLC trace of compound 18.

HPLC conditions for compound 18: Column, Kromasil 300-5-C18, Column size; 4.6×250 nm; injection concentration, 1 mg mL$^{-1}$; flow rate, 1 mL min$^{-1}$; detection, 254 nm; mobile phase, H₂O (0.1% TFA):CH₃OH=80:20 to 50:50 at 5 min to 80:20 at 10 min; retention time, 13 min (FIG. 2).

Figure 3:
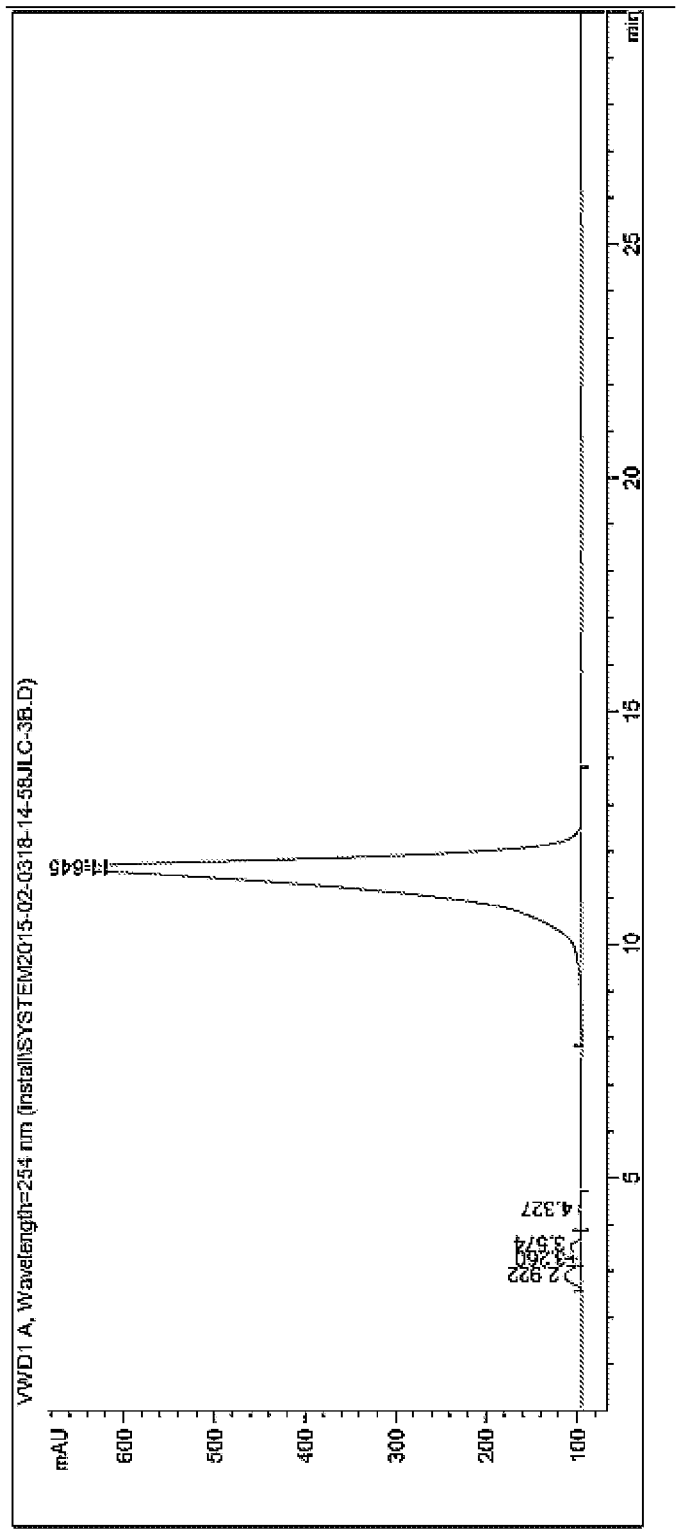
FIG. 3 shows a representative HPLC trace of compound 33.

HPLC conditions for compound 33: Column, Kromasil 300-5-C18, Column size; 4.6×250 nm; injection concentration, 1 mg mL$^{-1}$; flow rate, 1 mL min$^{-1}$; detection, 254 nm; mobile phase, H₂O (0.1% TFA):CH₃CN (0.1% TFA)=65:35; retention time, 12 min (FIG. 3).

Figure 4:
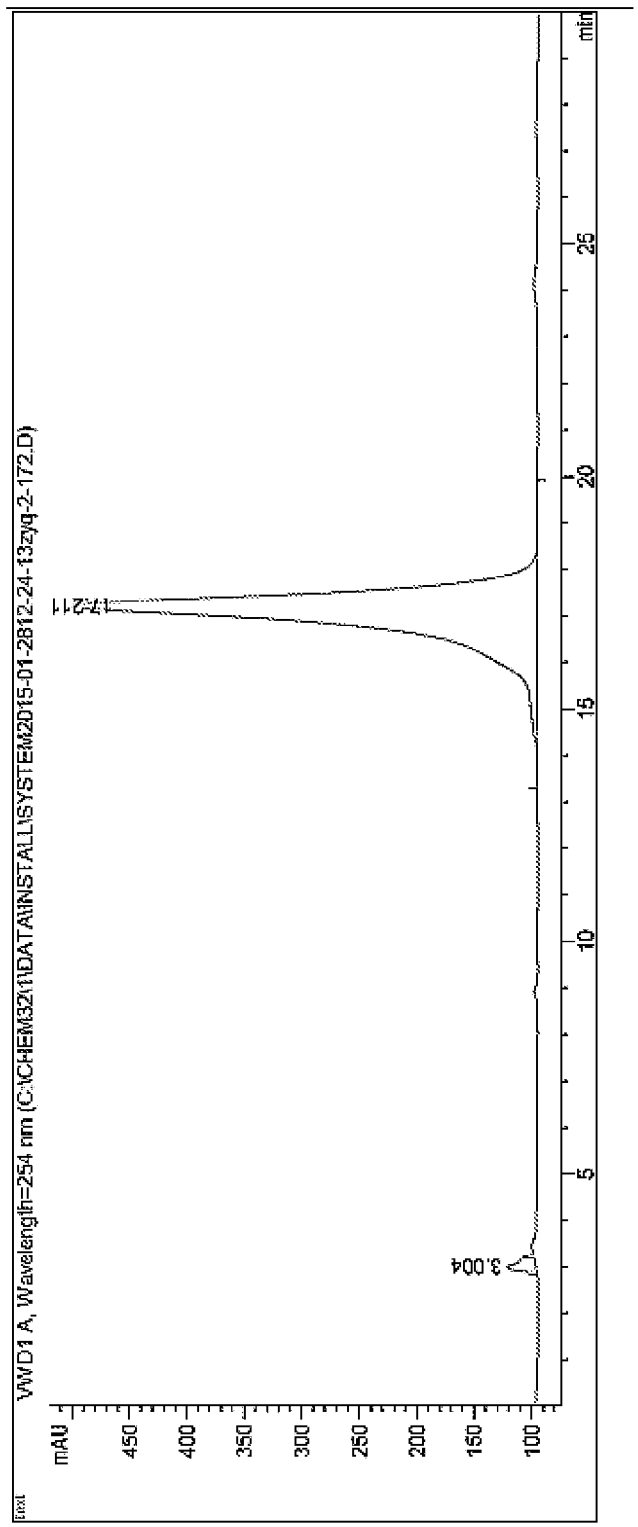
FIG. 4 shows a representative HPLC trace of compound 37.

HPLC conditions for compound 37: Column, Kromasil 300-5-C18, Column size; 4.6×250 nm; injection concentration, 1 mg mL$^{-1}$; flow rate, 1 mL min$^{-1}$; detection, 254 nm; mobile phase, H₂O (0.1% TFA):CH₃CN (0.1% TFA)=75:25; retention time, 17 min (FIG. 4).

G. EXAMPLES

1. Compound Screening to Discover Small-Molecule Inhibitors for the β-Catenin/Tcf Interaction The homogenous fluorescence polarization (FP) and AlphaScreen assays have been established to evaluate β-catenin/Tcf inhibitors (Zhang et al. (2012) *Anal. Biochem.* 424, 57-63). In the FP assay, C-terminally fluorescein-labeled human Tcf4 (residues 7-51) and human β-catenin (residues 138-686) were used. After β-catenin and fluorescein-Tcf4 form a protein-protein complex, the fluorophore is attached to a high-molecular-weight protein complex (≥60 kDa) and has a low rotational speed when it is excited by plane-polarized light. The resulting emitted light is significantly polarized. When an inhibitor completely disrupts the β-catenin/fluorescein-Tcf4 PPI, the fluorophore is only attached to Tcf4 (≤6 kDa), and the emitted light after excitation will be largely depolarized due to a high rotational speed of the fluorophore. AlphaScreen is a bead-based assay.

Figure 5A:
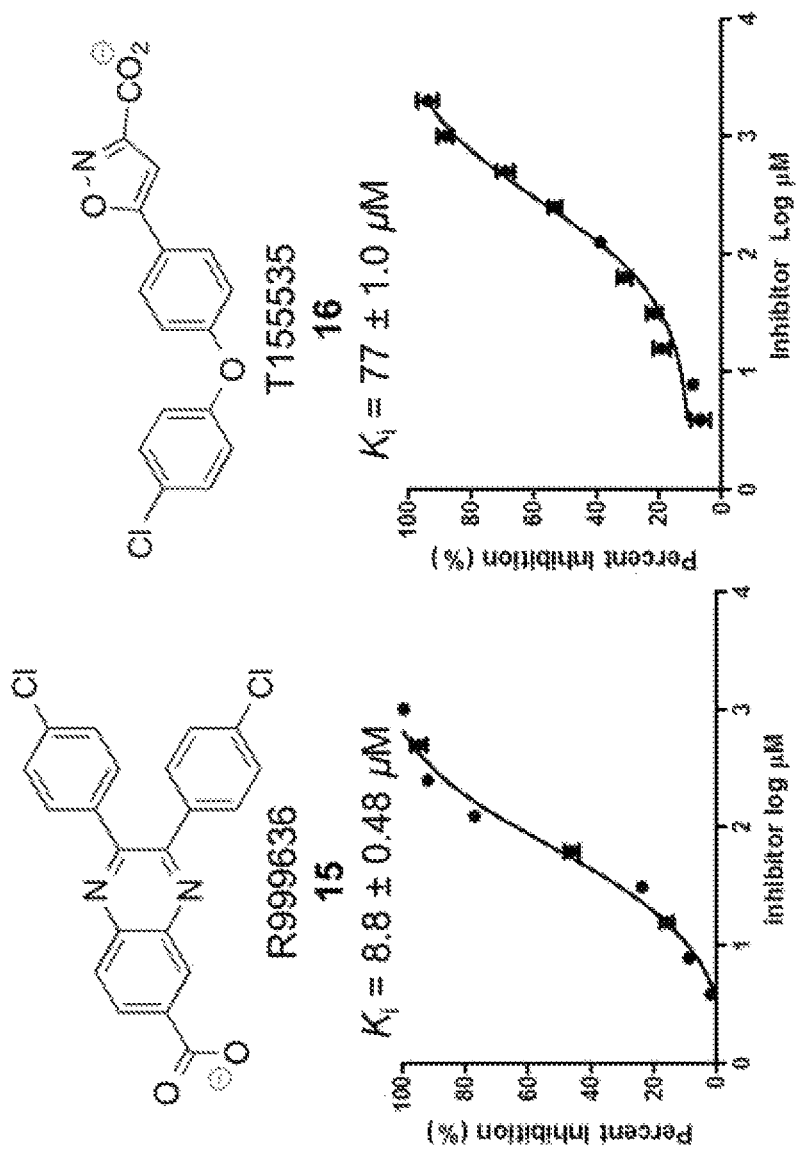
FIG. 5 shows representative data illustrating the inhibitory activities of compounds 15 (R999636), 16 (T155535), 17 (R999628), 18 (ZINC02092166), and 19A (ZINC20828864) in a FP competitive inhibition assay (FIG. 5A) and an AlphaScreen competitive inhibition assay (FIG. 5B).
Figure 5A:
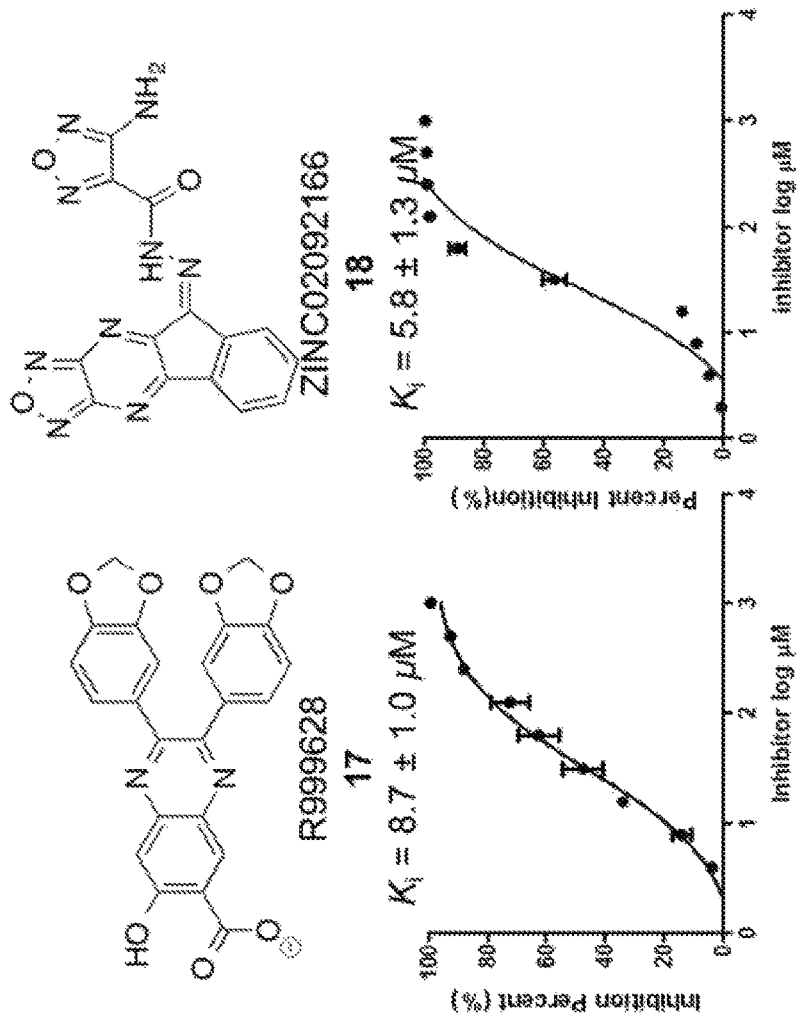
Figure 5A:
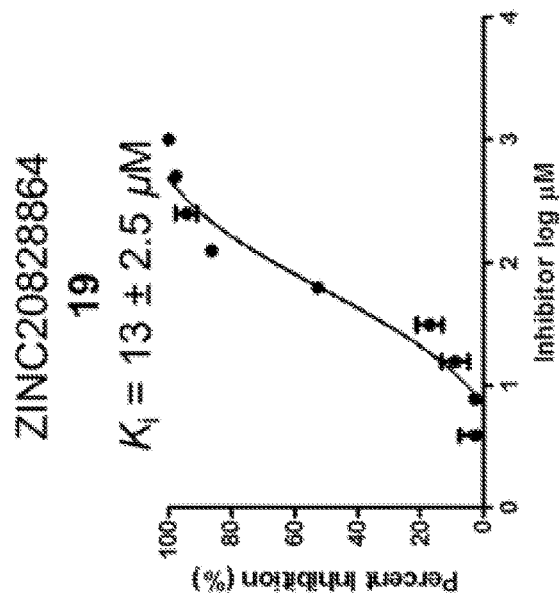
Figure 5A:
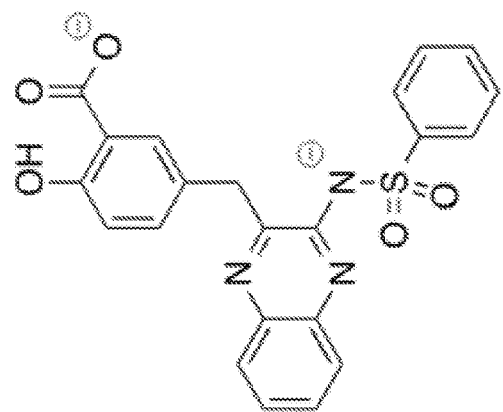
Figure 5B:
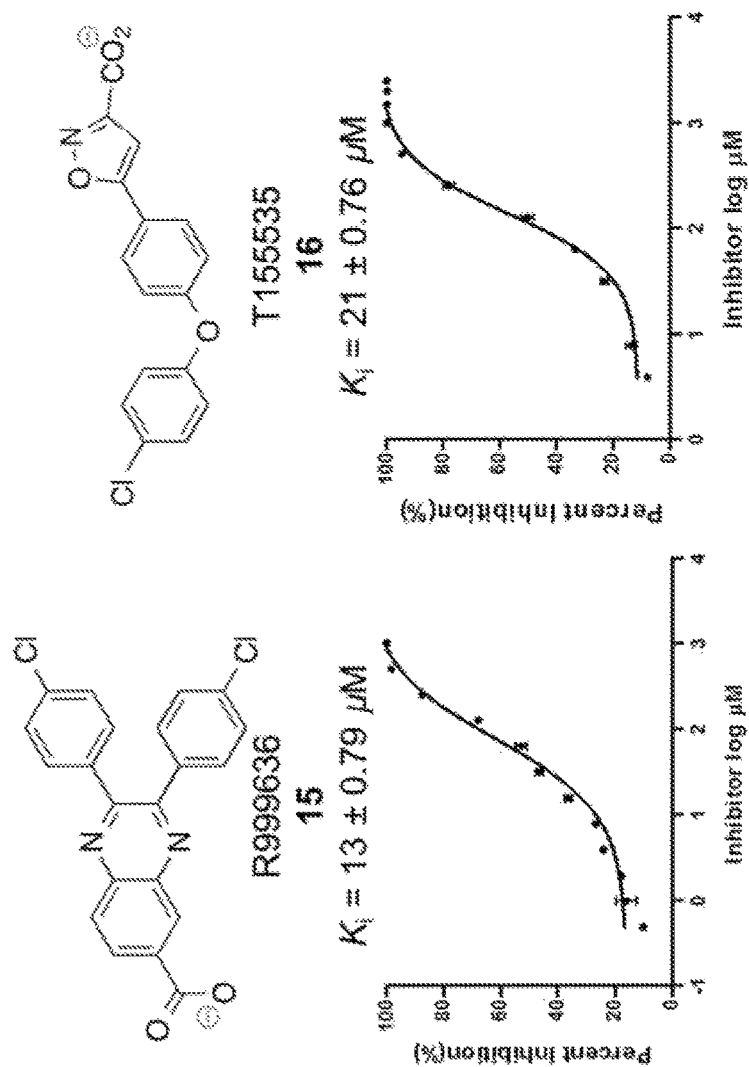
Figure 5B:
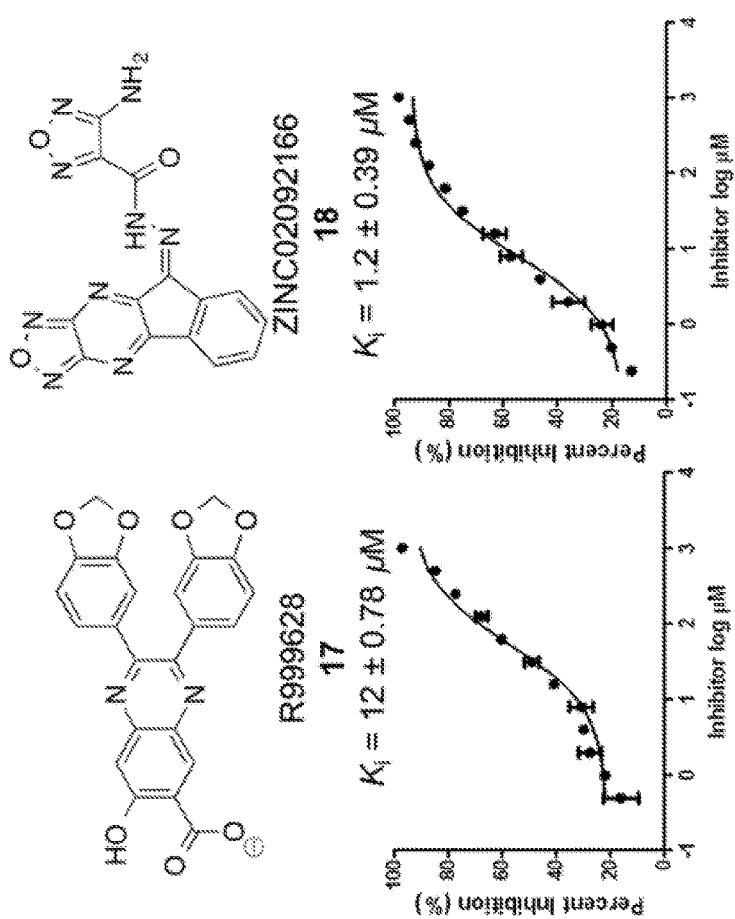

The streptavidin-coated donor beads and the nickel-chelate acceptor beads are brought together through the interaction between C-terminally biotinylated human Tcf4 (residues 7-51) and N-terminally $His_6$-tagged human β-catenin (residues 138-686). On laser excitation at 680 nm, the photo sensitizers inside the donor beads convert ambient oxygen to a singlet oxygen state. Only when the donor and acceptor beads are brought within 200 nm can the singlet oxygen molecules diffuse to the acceptor beads, resulting in extensive emission at 570 nm. If the inhibitor completely disrupts the β-catenin/Tcf PPI, no luminescence signal will be observed. In this study, 269 Sigma-Aldrich carboxylic acids and sulfonamides, 90 LOPAC[Pfizer] synthetic compounds, 24 compounds from the ZINC library, and 117 natural products, and 1593 Diversity Set V compounds from the Developmental Therapeutics Program of NCI/NIH were screened. In the screening, carboxylic acids and acidic sulfonamides were prioritized because the acid-rich Tcf4 $D^{16}ELISFKDE^{24}$ segment has been recognized as a key binding motif for the β-catenin/Tcf PPI. The compounds that displayed a $K_i$ value ≤25 μM in either assay were kept for further evaluation. Four compounds, 15-18 and 19A (see Table 2), exhibited reproducible and dose-dependent inhibitory activities in both assays. None of them were false positives in the AlphaScreen counter screen or aggregated as examined by the spin-down counter screen (Mysinger et al. (2012) *Proc. Natl. Acad. Sci. U.S.A.* 109, 5517-5522) and the dynamic light scattering experiments. None of these compounds had fluorescence interference in both assays. Table 3, FIG. 5A and FIG. 5B shows the results of the FP and AlphaScreen assays.

TABLE 3

| Cmpd. No. | $K_i$ + SD (μM) | |
| --- | --- | --- |
| | FP | AlphaScreen |
| 15 | 8.8 ± 0.48 | 13 ± 0.79 |
| 16 | 77 ± 1.0 | 21 ± 0.76 |
| 17 | 8.7 ± 1.0 | 12 ± 0.78 |
| 18 | 5.8 ± 1.3 | 1.2 ± 0.39 |
| 19A | 13 ± 2.5 | n.d. |
| 1[a,b] | 18 ± 2.1 | n.a. |
| 2[a,b] | 36 ± 4.4 | 5.9 ± 0.96 |
| 3[a,b] | 5.8 ± 0.24 | 3.8 ± 0.45 |
| 7[a,b] | 1.80 ± 0.72 | n.d. |
| 8[a,b] | 370 ± 6.3 | n.d. |
| 9[a,b] | 80 ± 4.2 | n.d. |
| 10[a,b] | 54 ± 5.2 | n.d. |
| 13[a] | 3.1 ± 0.48 | 3.8 ± 0.45 |
| 14[b] | 1.4 ± 0.12 | 1.3 ± 0.56 |

[a]Yu et al. (2013) *ACS Chem. Bio.* 8, 524-529;
[b]Zhang et al. (2012) *Anal. Biochem.* 424, 57-63.

Figure 6A:
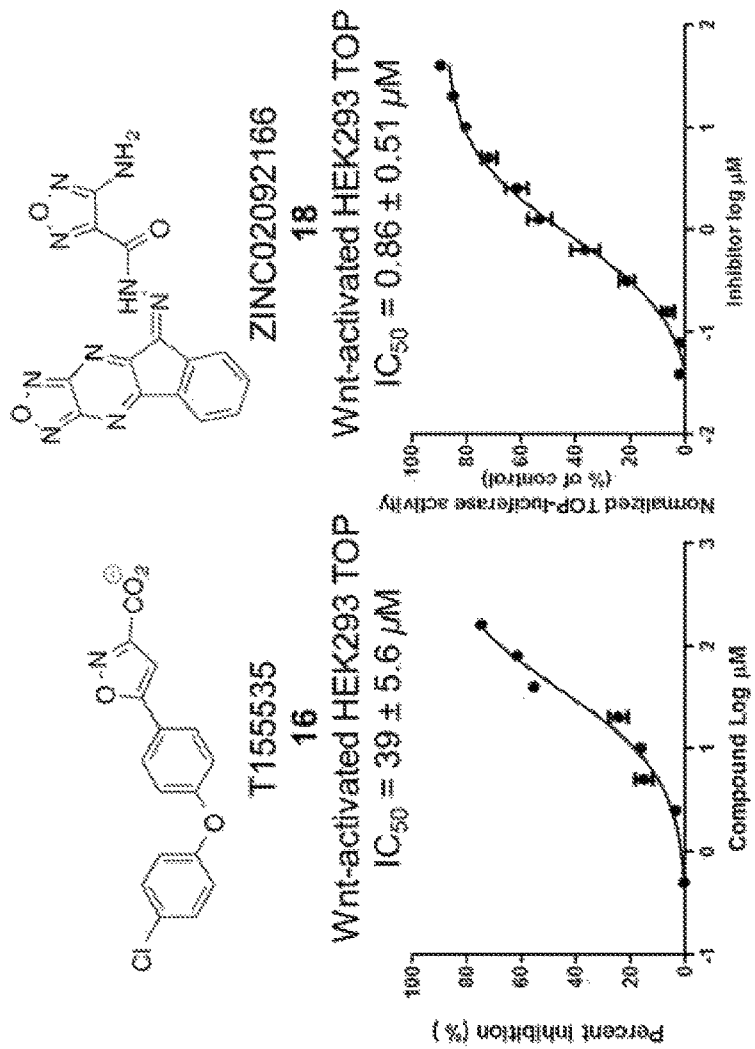
FIG. 6 shows representative data illustrating the inhibitory effects of compounds 16 (T155535), 18 (ZINC02092166), 8 (iCRT3), and 9 (iCRT5) on the transactivation of the canonical Wnt signaling pathway in a TOPFlash assay using pcDNA3.1-β-catenin transfected HEK293 cells (FIG. 6A), colorectal cancer SW480 cells (FIG. 6B), and FOPFlash assay using psDNA3.1-β-catenin transfected HEK293 cells (FIG. 6C).
Figure 6A:
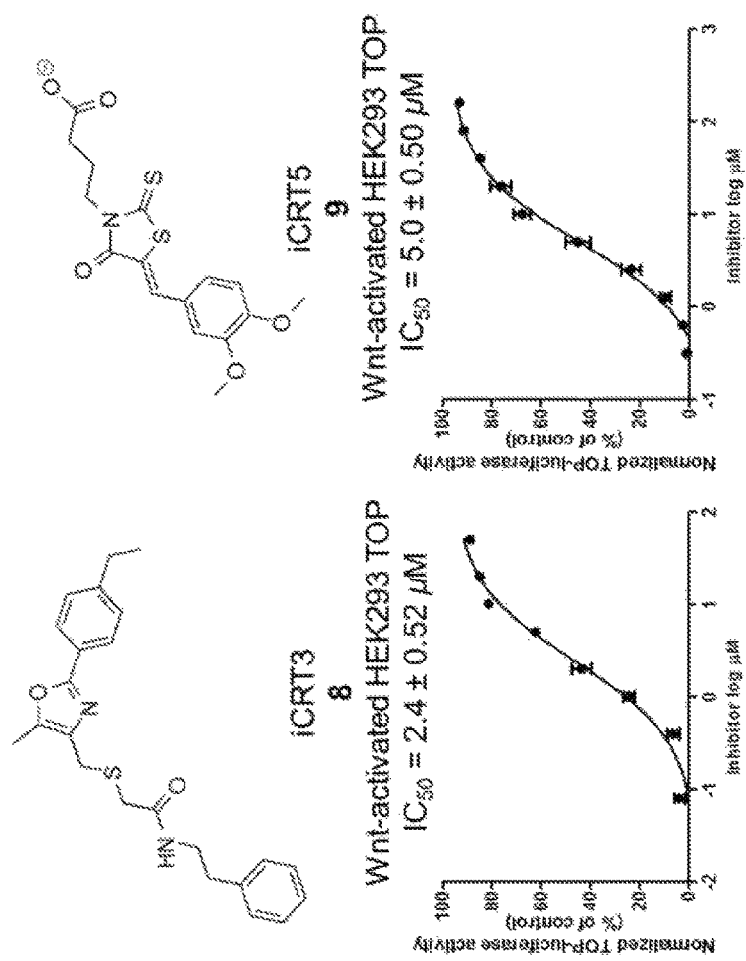
Figure 6B:
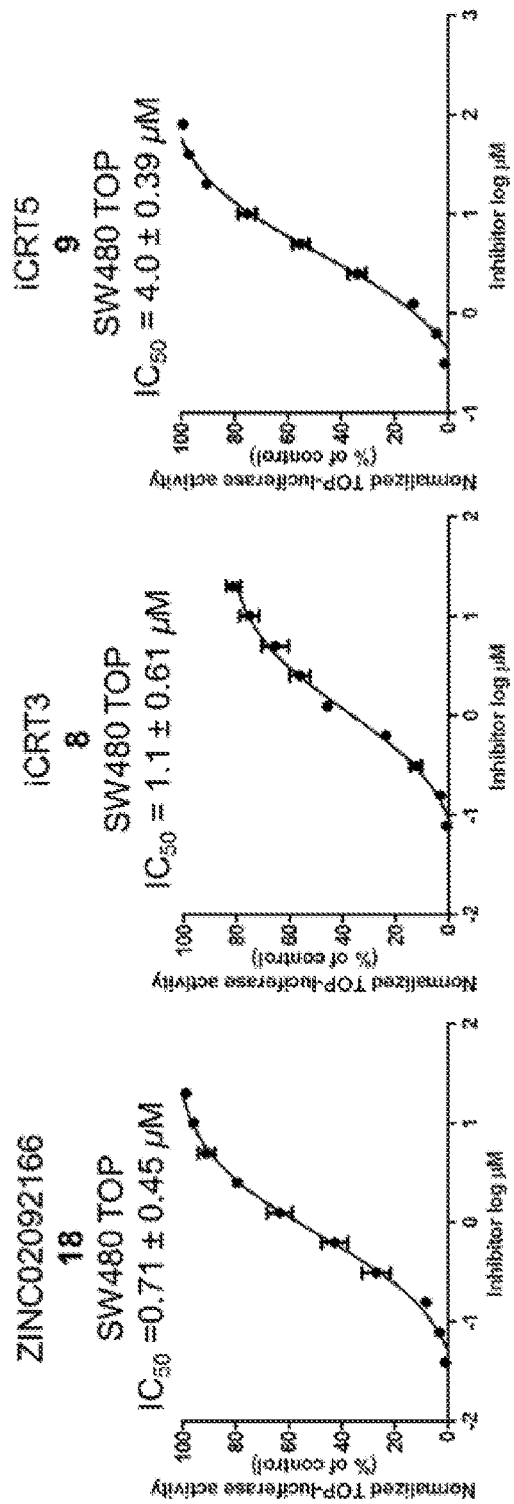
Figure 6C:
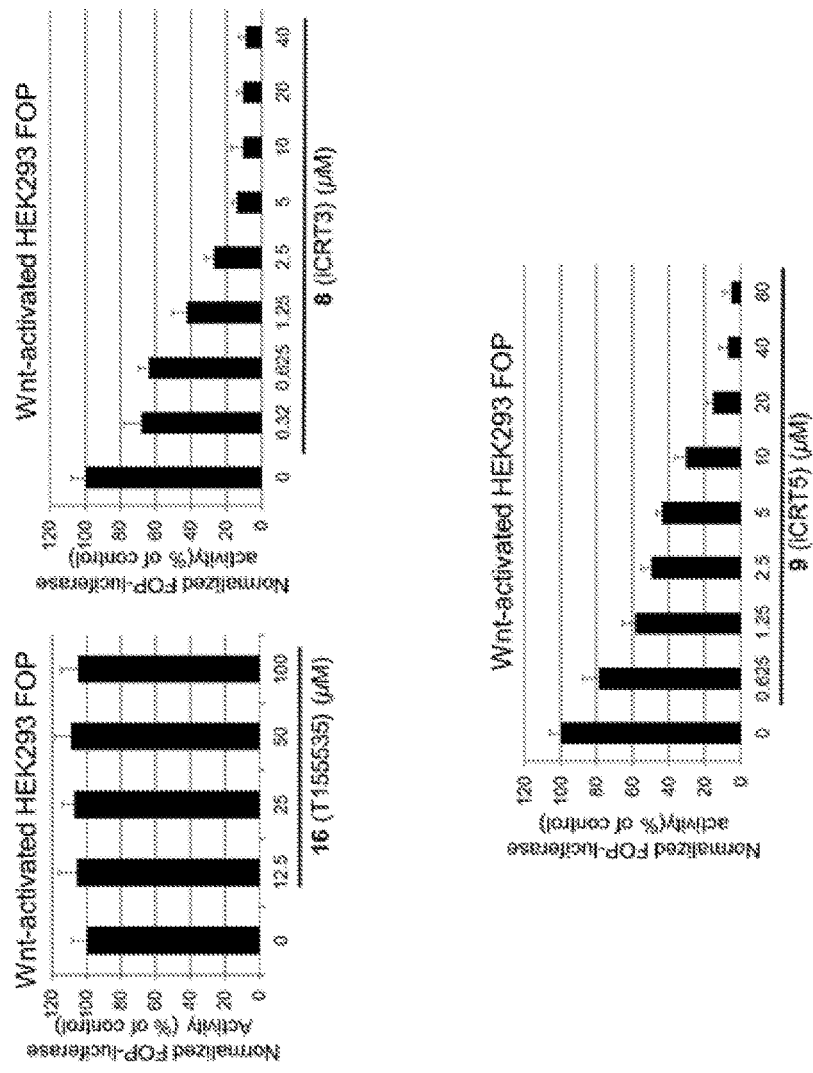
Figure 7:
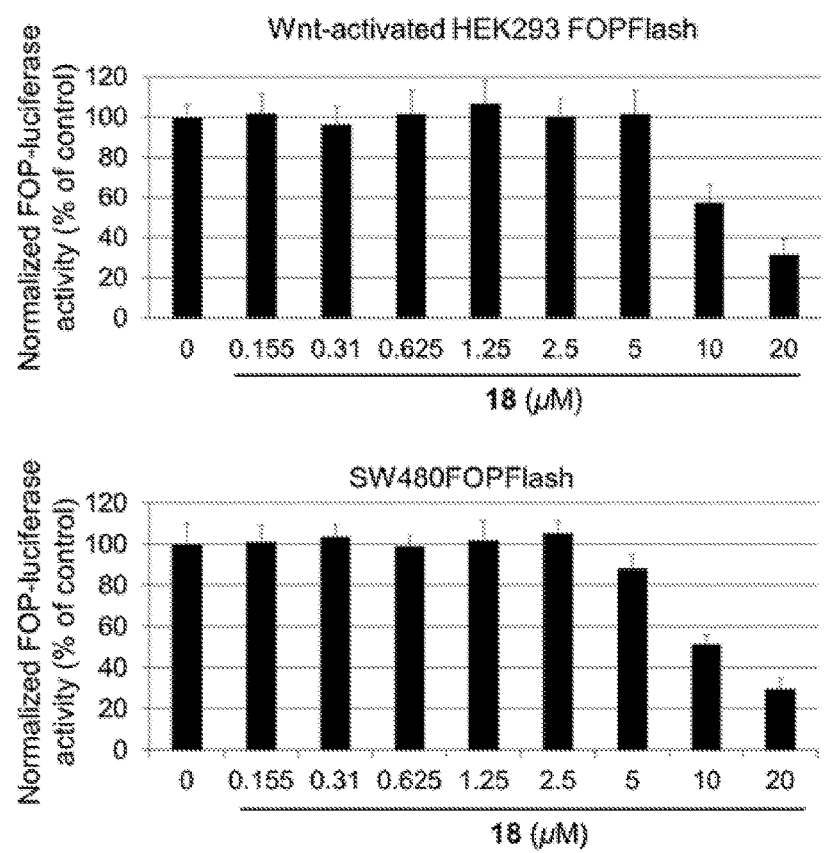
FIG. 7 shows representative data illustrating the inhibitory effects of compound 18 (ZINC02092166) in a FOP-Flash luciferase reporter assay using pcDNA3.1-β-catenin transfected HEK293 cells and colorectal cancer SW480 cells.
Figure 8:
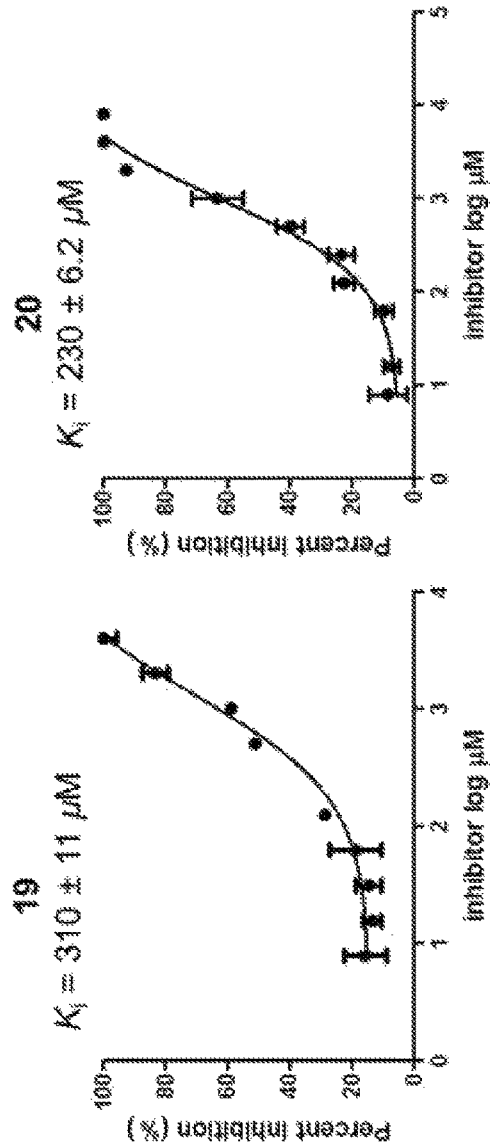
FIG. 8 shows representative data illustrating the FP competitive inhibition assay results of compounds 19B, 20, 21 (UZI2987998), 23 (CDS018522), and 25 (CDS18901) for the inhibition of the β-catenin/Tcf4 PPI.
Figure 8:
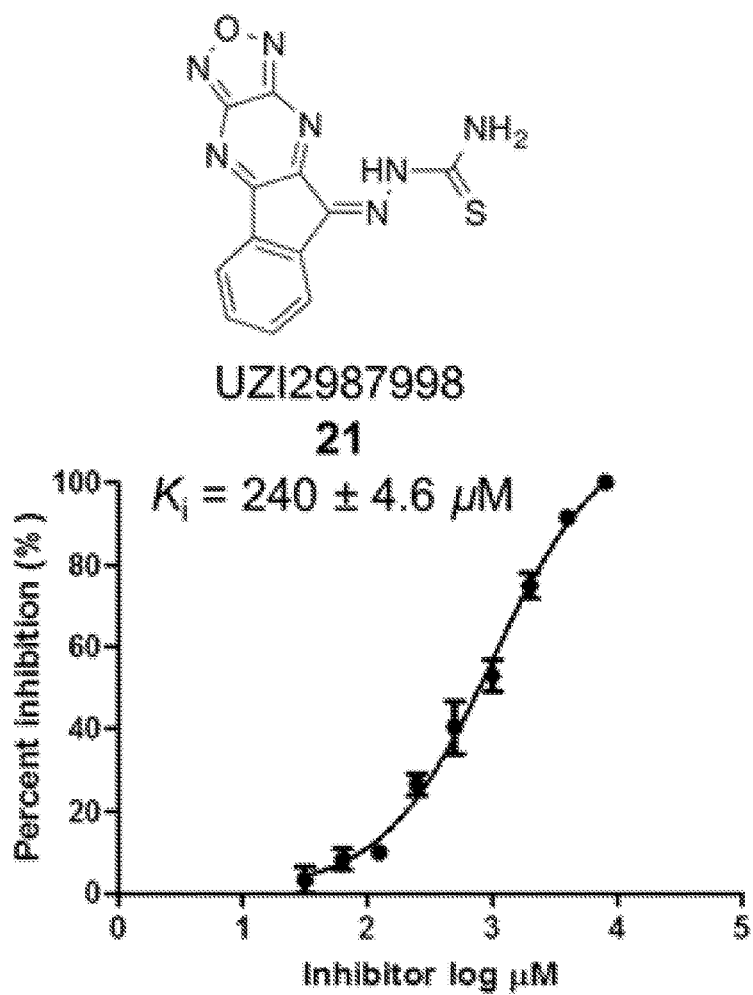
Figure 8:
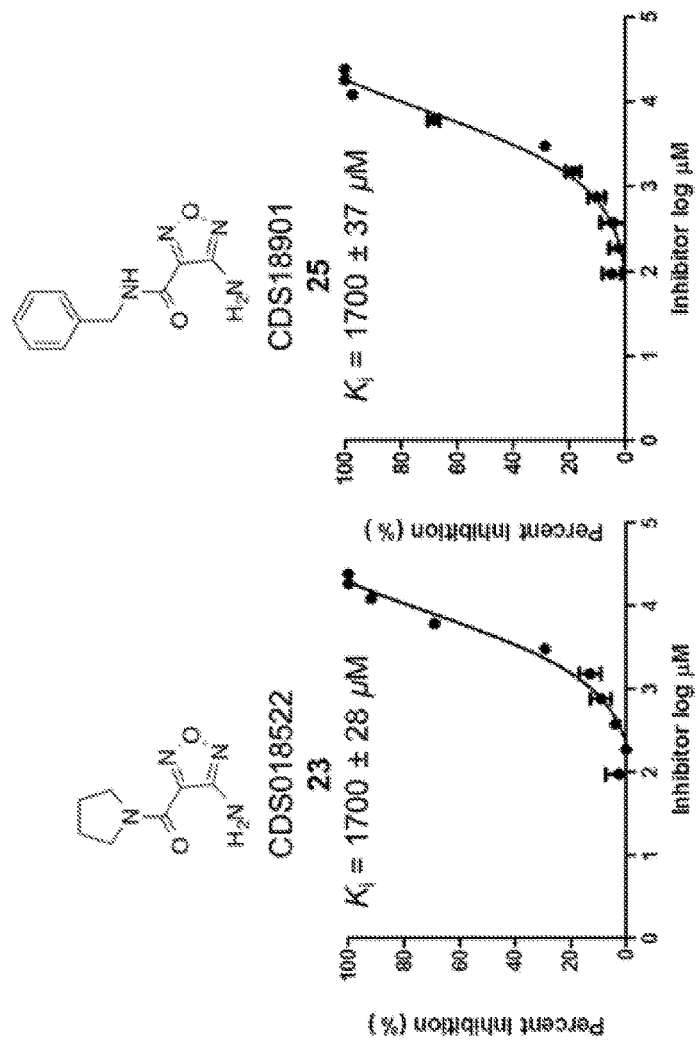

To determine whether the above compounds inhibit the transactivation of canonical Wnt signaling, Wnt-responsive luciferase reporter assays were performed (Korinek et al. (1997) *Science* 275, 1784-1787). The results are illustrated in Table 4, FIG. 6A, FIG. 6B, and FIG. 6C. Compound 16 inhibited the TOPFlash luciferase (a luciferase reporter with eight wild-type Tcf binding sites) activity in Wnt-activated HEK293 cells. Compound 18 inhibited the TOPFlash luciferase activity in both tested cell lines, pcDNA3.1-β-catenin transfected HEK293 and colorectal cancer SW480, by dose-dependent manners with the $IC_{50}$ values of 0.86±0.51 and 0.71±0.45 μM. Compounds 8 and 9, which were identified by the highly sensitive luciferase reporter (Super 16×TOPFlash) assay (Gonsalves et al. (2011) *Proc. Natl. Acad. Sci. U.S.A.* 108, 5954-5963), were used as the reference inhibitors for comparison. Compound 18 also inhibited the FOPFlash luciferase (a luciferase reporter with eight mutant Tcf binding sites) activity at the concentrations ≥5 μM (FIG. 7), indicating off-target effects at high concentrations. Compounds 8 and 9 also inhibited the FOPFlash luciferase reporter activity, as shown in FIG. 8.

TABLE 4

| | TOPFlash $IC_{50}$ ± SD (μM) | |
| --- | --- | --- |
| Cmpd. No. | Wnt-activated HEK293 | SW480 |
| 15 | >1.0E2 | n.d. |
| 16 | 39 ± 5.6 | n.d. |
| 17 | >1.0E2 | n.d. |
| 18 | 0.86 ± 0.51 | 0.71 ± 0.45 |
| 8 | 2.4 ± 0.52 | 1.1 ± 0.61 |
| 9 | 5.0 ± 0.50 | 4.0 ± 0.39 |

The MTs cell viability assay was performed to assess the effects of these compounds on the growth of colorectal cancer cell lines, SW480, HCT116, and HT29. These cancer cell lines were chosen based on their known dependence on the β-catenin/Tcf PPI for growth and survival. SW480 and HT29 cells harbor the deletions of APC, whereas HCT116 cells harbor a mutation on β-catenin that blocks β-catenin phosphorylation and ubiquitination (Ilyas et al. (1997) *Proc. Natl. Acad. Sci. U.S.A.* 94, 10330-10334; Sparks et al. (1998) *Cancer Res.* 58, 1130-1134). The MTs assay results indicated that 15 inhibited the growth of SW480, HCT116, and HT29 cells with the $IC_{50}$ values of 38±1.1, 22±5.9, and 41±1.0 μM. Compound 18 inhibited the growth of SW480, HCT116, and HT29 cells with the $IC_{50}$ values of 0.85±0.10, 0.99±0.13, and 1.1±0.093 μM, respectively (see Table 5).

TABLE 5

| Cmpd. | $IC_{50}$ ± SD (μM) | | |
| --- | --- | --- | --- |
| No. | SW480 | HCT116 | HT29 |
| 15 | 38 ± 1.1 | 22 ± 5.9 | 41 ± 1.0 |
| 16 | >4.0E2 | >4.0E2 | 430 ± 25 |
| 17 | 110 ± 21 | 250 ± 21 | 3.0E2 ± 18 |
| 18 | 0.85 ± 0.10 | 0.99 ± 0.13 | 1.1 ± 0.093 |
| 2 | 5.5 ± 1.3 | 1.2 ± 0.48 | 1.8 ± 0.13 |
| 9 | 240 ± 2.5 | 180 ± 2.9 | 290 ± 2.4 |

Figure 9A:
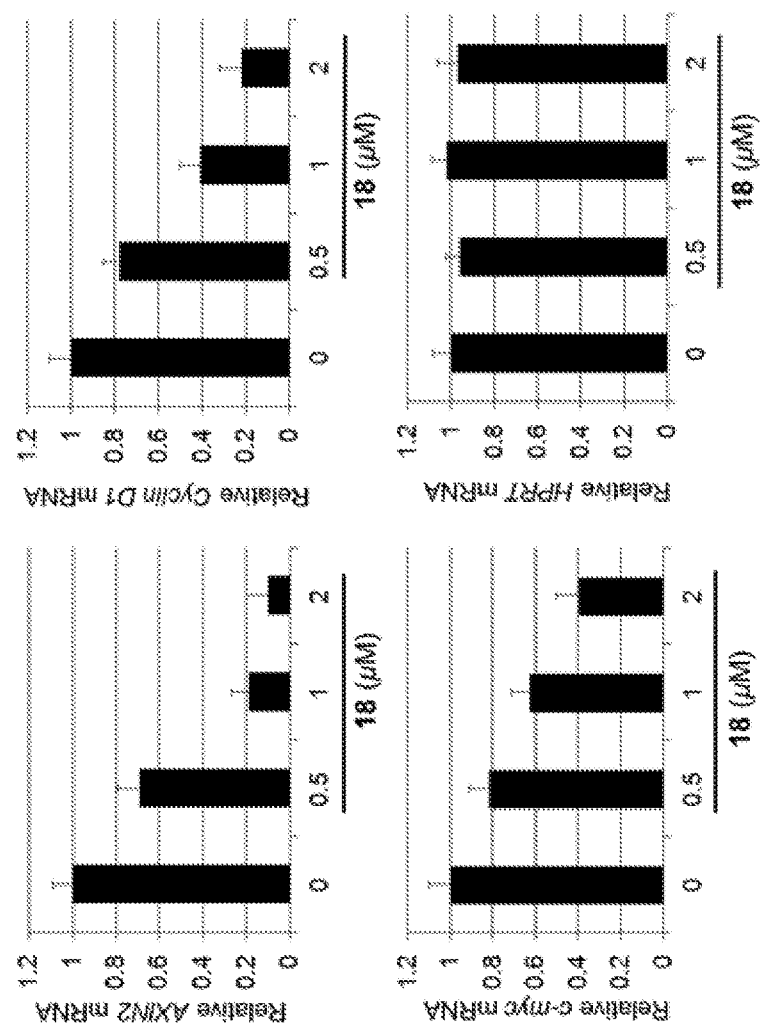
FIGS. 9A-C show representative data pertaining to the cell-based characterization of compound 18.
Figure 9B:
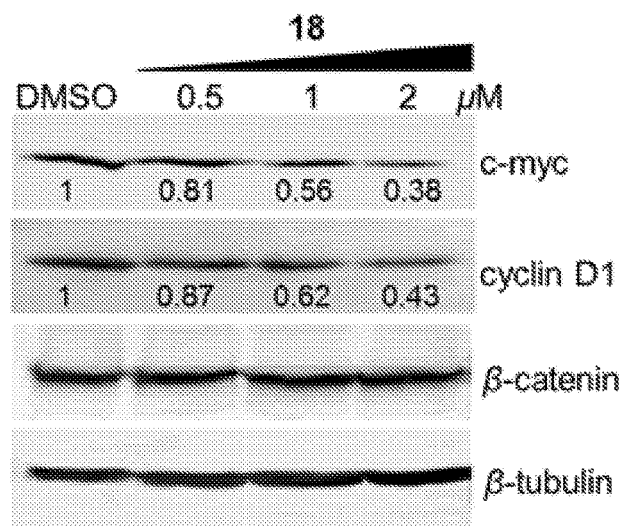
Figure 9C:
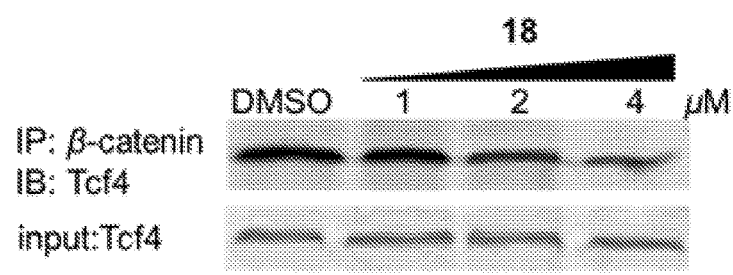

2. Effects of 18 on the Expression of Wnt/β-Catenin Target Genes and the Co-Immunoprecipitation Study AXIN2 is a specific target gene for the canonical Wnt signaling pathway (Leung et al. (2002) *J Biol. Chem.* 277, 21657-21665). Cyclin D1 and c-myc are two Wnt target genes that drive cancer progression including in SW480 cells (Tetsu and McCormick (1999) *Nature* 398, 422-426). The quantitative real time PCR study indicated that 18 down-regulated the expression of AXIN2, cyclin D1, and c-myc in dose-dependent manners in SW480 cells, as shown in FIG. 9A. More than 50% of mRNA expression was inhibited at a dose of 2 μM. Compound 18 did not affect the expression of house-keeping gene HPRT. The protein expression levels of cyclin D1, c-myc and β-catenin in SW480 cells were examined by the Western blot analysis (FIG. 9B). The expression of proteins cyclin D1 and c-myc were significantly reduced after the treatment with 18. Compound 18 did not reduce the expression level of β-catenin, indicating that it does not inhibit the β-catenin degradation pathways. A coimmunoprecipitation experiment was performed to evaluate the inhibitory potency of 18 in a cellular context. As shown in FIG. 9C, compound 18 inhibits the β-catenin/Tcf PPI in a dose-dependent manner in SW480 cells.

Referring to FIG. 9A, a quantitative real time PCR study was performed to determine the changes of mRNA expression of AXIN2, cyclin D1, c-myc, and HPRT in response to different concentrations of compound 18. Each set of data is expressed as a mean±standard deviation (n=3).

Referring to FIG. 9B, Western blot analysis was used to monitor the changes of protein expression of c-myc, cyclin D1, and β-catenin in response to different concentrations of compound 18. B-Tubulin was used as an internal reference.

Referring to FIG. 9C, a coimmunoprecipitation experiment was used to evaluate the inhibitory effect of compound 18 on the β-catenin/Tcf association. IP: immunoprecipitation; IB: immunoblotting.

3. Fragmentation of Compound 18

Figure 10:
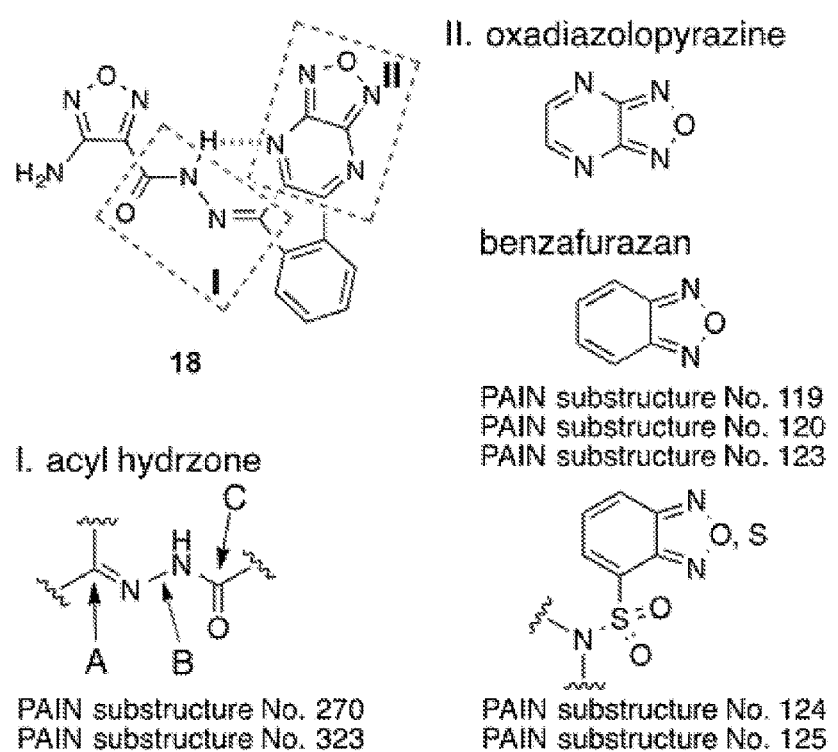
FIG. 10 shows a representative image illustrating the potential reactive sites of compound 18.

Compound 18 exhibited a higher inhibitory potency in cell-based studies than in the FP and AlphaScreen assays and inhibited the FOPFlash luciferase activity. This brought the concern that 18 had off-target effects. An analysis of the structure of 18 indicated two functional groups that might be problematic (FIG. 10). One is the acyl hydrazone moiety, which has been identified as a PAINS substructure. Out of three vulnerable sites in acyl hydrazone, site A, the nucleophilic imine carbon atom, is most reactive and susceptible to nucleophilic attack. A similar site in hydrazones has been reported causing frequent hits in biochemical assays (Jadhav et al. (2010) *J. Med. Chem.* 53, 37-51; Che et al. (2012) *J. Chem. Inf. Model* 52, 913-926). The N—N single bond is an "undesirable" substructure due to the reactivity to nucleophiles (Yu et al. (2011) *Eur. J. Med. Chem.* 46, 5833-5837). In any case, site B of 18 is located in an electron-deficient environment and unlikely to be reactive. Site C, the amide carbon atom, is more stable than sites A and B. The second is the oxadiazolopyrazine ring. No false positive reactivity is associated with this functional group. A related substructure, benzofurazan, has been reported as a PAINS substructure (Baell and Holloway (2010) *J. Med. Chem.* 53, 2719-2740; Metz et al. (2007) *J. Comput.-Aided Mol. Des.* 21, 139-144; Huth et al. (2007) *Chem. Res. Toxicol.* 20, 1752-1759; Dahlin et al. (2015) *J. Med. Chem.* 58, 2091-2113). However, the reactivity of benzofurazan with singlet oxygen (Takabatake et al. (2001) *Tet. Lett.* 42, 987-989) and nucleophiles (Okabe et al. (2002) J. *Chromatogr. A.* 982, 111-118) is caused by the fused benzene ring, which is absent in 18. The hydrophilic nature of the oxadiazolopyrazine moiety and the low polarizability of the tetracyclic ring make 18 unlikely to be a DNA intercalator (Reha et al. (2002) *J. Am. Chem. Soc.* 124, 3366-3376; Reynisson et al. (2003) 125, 2072-2083). An intramolecular H-bond between the nitrogen atom of the oxadiazolopyrazine moiety and the NH group of acyl hydrazone may stabilize the structure of 18, as shown in FIG. 10.

Since the nucleophilic imine carbon atom of 18 was recognized problematic, a fragmentation of 18 was conducted. As shown in Table 6, compounds 19B, 21, 23, and 25 exhibited some inhibitory activities for the disruption of the β-catenin/Tcf PPI but were much lower than 18.

TABLE 6

| Cmpd. No. | FP $K_i$ ± SD (μM) |
|---|---|
| 19B | 310 ± 11 |
| 20 | 230 ± 6.2 |
| 21 | 240 ± 4.6 |
| 22 | >2.0E3 |

TABLE 6-continued

| Cmpd. No. | FP $K_i$ ± SD (μM) |
|---|---|
| 23 | 1700 ± 28 |
| 24 | >2.0E3 |
| 25 | 1700 ± 37 |

4. Structure-Activity Relationship of the Derivatives of 18

Figure 11A:
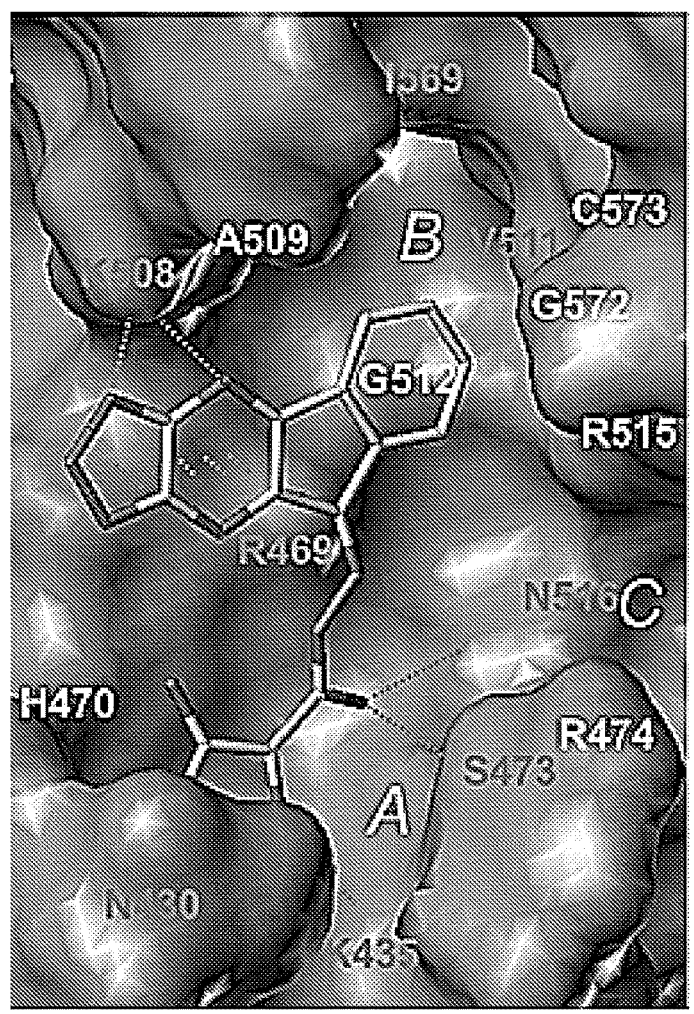
FIG. 11A and FIG. 11B show a representative Glide docking model (FIG. 11A) and a stick model (FIG. 11B) of compound 18 with β-catenin.
Figure 11B:
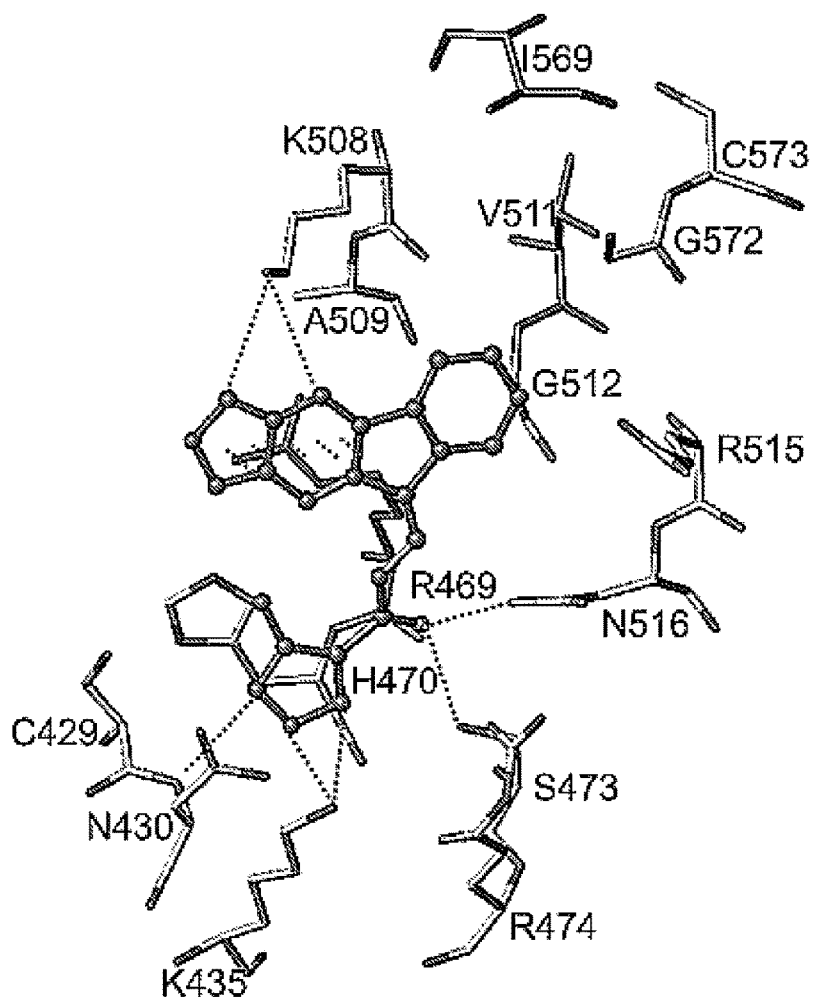
Figure 12:
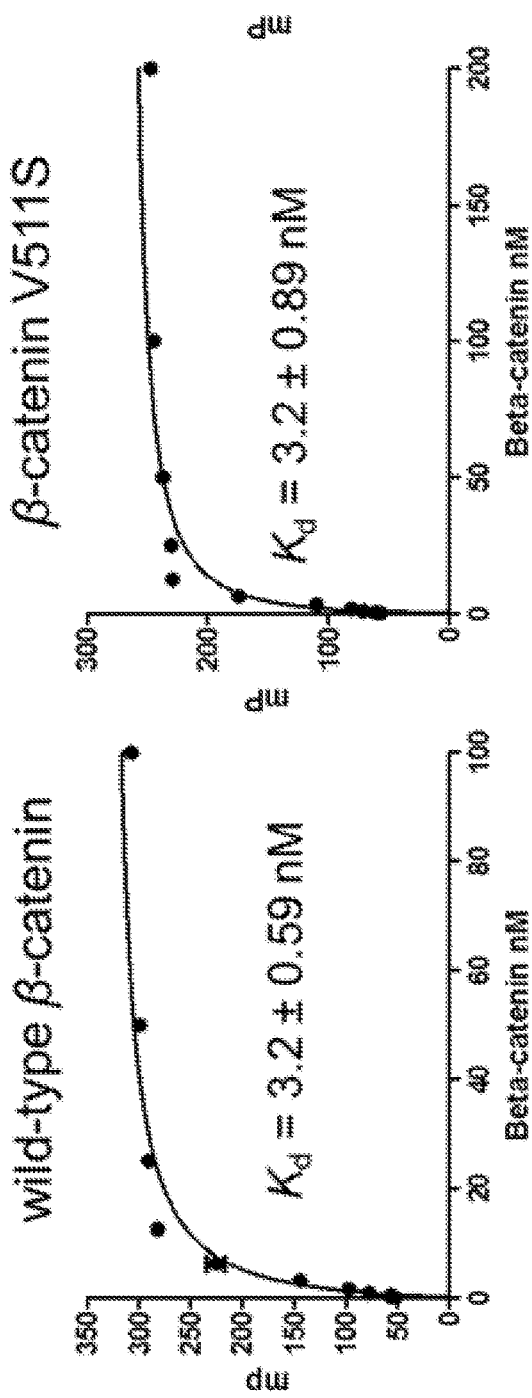
FIG. 12 shows representative data determining that V511S, V511S/I516S, and R469A of β-catenin have the same apparent $K_d$ values as wild-type β-caatenin when binding with wild-type Tcf4.
Figure 12:
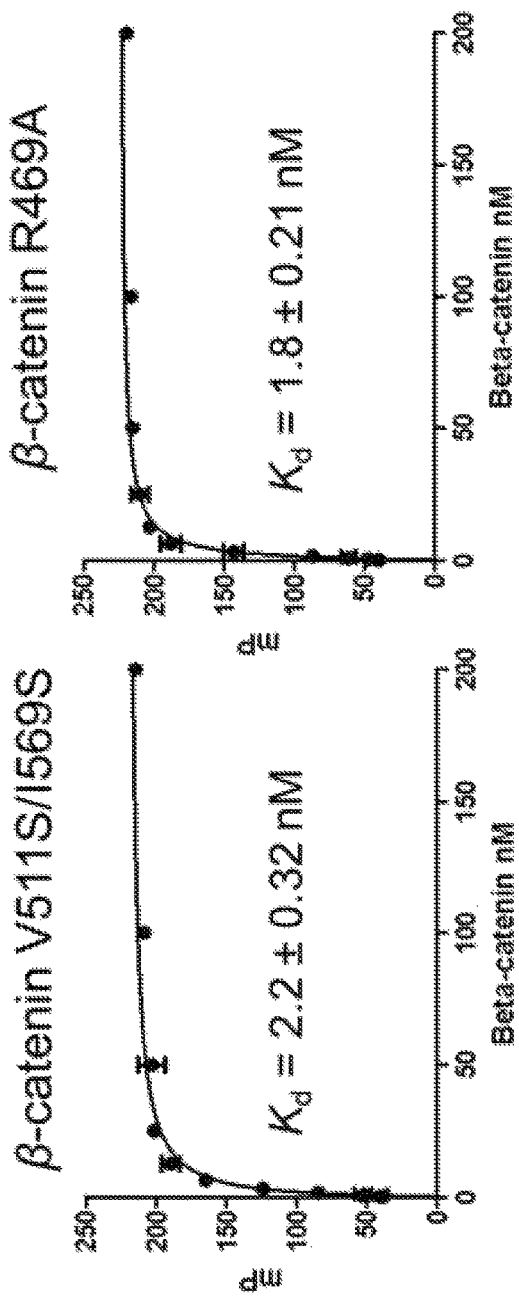
Figure 12:
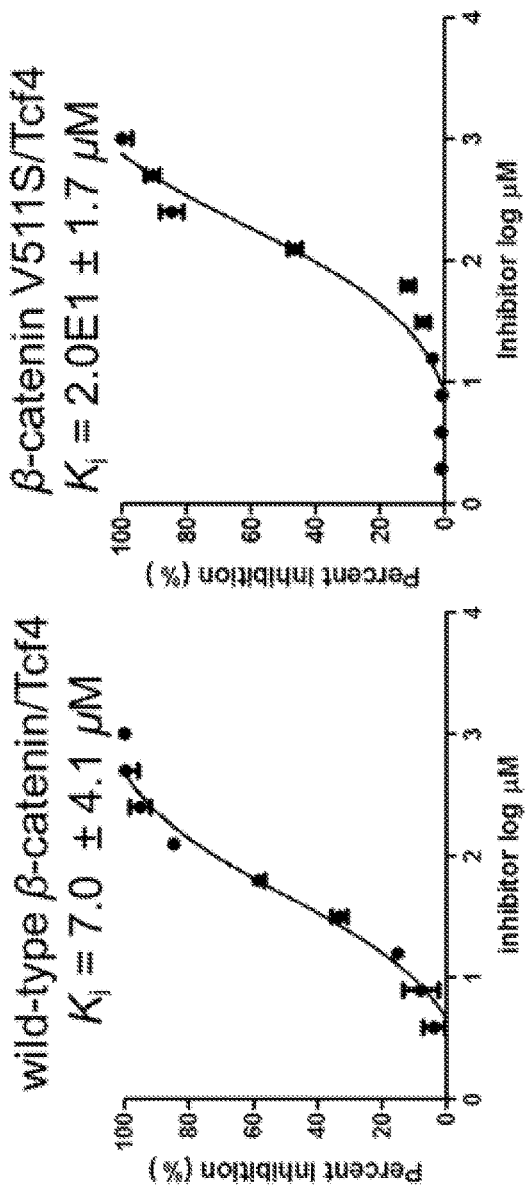
Figure 12:
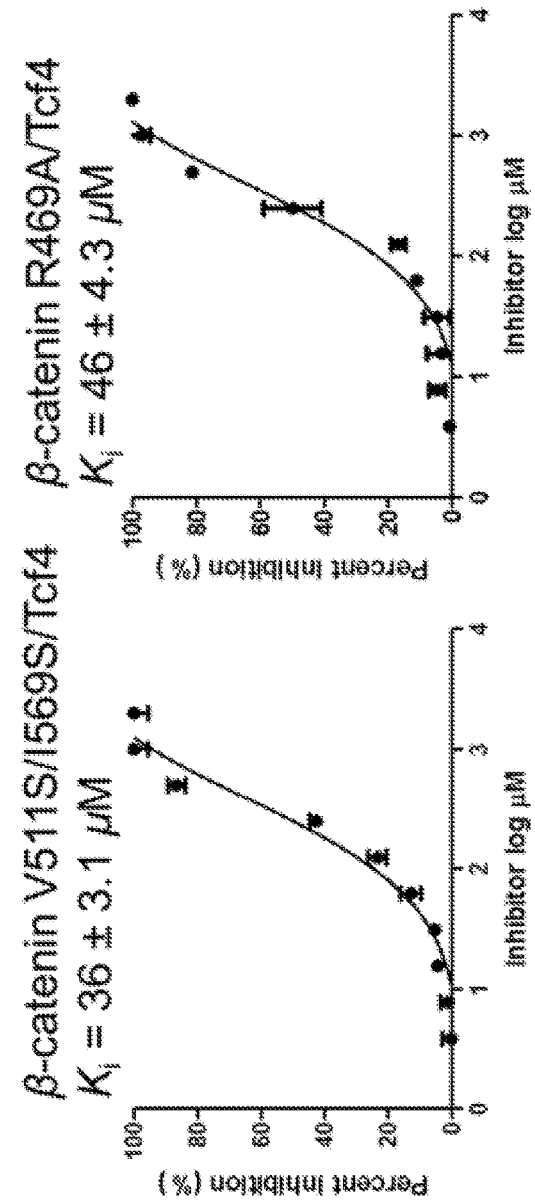

Further optimization started with the resynthesis of 18 to examine the chemical structure. The FP and AlphaScreen assays indicated that the resynthesized 18 had a similar biological activity as that observed in commercially available 18 (see Table 8). The AutoDock Vina (Trott and Olson (201) *J. Comput. Chem.* 31, 455-461) blind docking study was performed to explore the possible binding pockets in β-catenin for 18. The result predicted that 18 preferentially bound to hot region 1 (AutoDock Vina scores were −8.4 kcal/mol, −4.6 kcal/mol, and −3.7 kcal/mol for hot regions 1, 2, and 3, respectively). The Glide (Friesner et al. (2004) *J Med. Chem.* 47, 1739-1749), AutoDock (Morris et al. (2009) *J. Comput. Chem.* 30, 2785-2791), and AutoDock vina docking studies predicted one recurring binding conformation of 18 in β-catenin, as shown in FIG. 11A and FIG. 11B: the 4-amino-1,2,5-oxadiazole ring was predicted to form H-bonds with the side chain amino group of K435 and the backbone NH group of N430; the amide carbonyl group of 18 was predicted to form H-bonds with the side chain amide group of N516 and the hydroxyl group of S473; the tetracyclic ring was predicted to form a cation-π interaction with the positively charged gaunidino group of R469; two nitrogen atoms of the oxadiazolopyrazine ring formed H-bonds with K508; and the benzene ring was predicted to locate in hydrophobic pocket B. Crystallographic analyses indicated that R469, V511, and I569 did not interfere with the β-catenin/Tcf PPI. Three mutants, R469A, V511S, and V511S/I569S, were made (Yu et al. (2013) *ACS Chem. Biol.* 8, 524-529; Huang et al. (2014) *ACS Chem. Biol.* 9, 193-201). Native gel electrophoresis, thermal shift, and CD experiments confirmed the homogeneity, the thermal stability, and the secondary structure integrity of all purified proteins. The FP saturation binding assays demonstrated that V511S, V511S/I516S, and R469A of β-catenin had the same apparent $K_d$ values as wild-type β-catenin when binding with wild-type Tcf4, as shown in FIG. 12. The FP competitive inhibition assay was performed to evaluate the roles of these three residues in inhibitor binding. The $K_i$ value of the resynthesized 18 for wild-type β-catenin/Tcf4 interactions was 7.0±4.1 μM. The $K_i$ values of the resynthesized 18 for β-catenin V511S/Tcf4 and β-catenin V511S/I569S double mutant/Tcf4 interactions were 2.0E1±1.7 and 36±3.1 μM, respectively. Without wishing to be bound by theory, this may suggest that a change of pocket B from hydrophobic to hydrophilic reduces the potency of 18. The $K_i$ value of the resynthesized 18 for β-catenin R469A/Tcf4 interactions was 46±4.3 μM, indicating the role of R469 in inhibitor binding.

Figure 13:
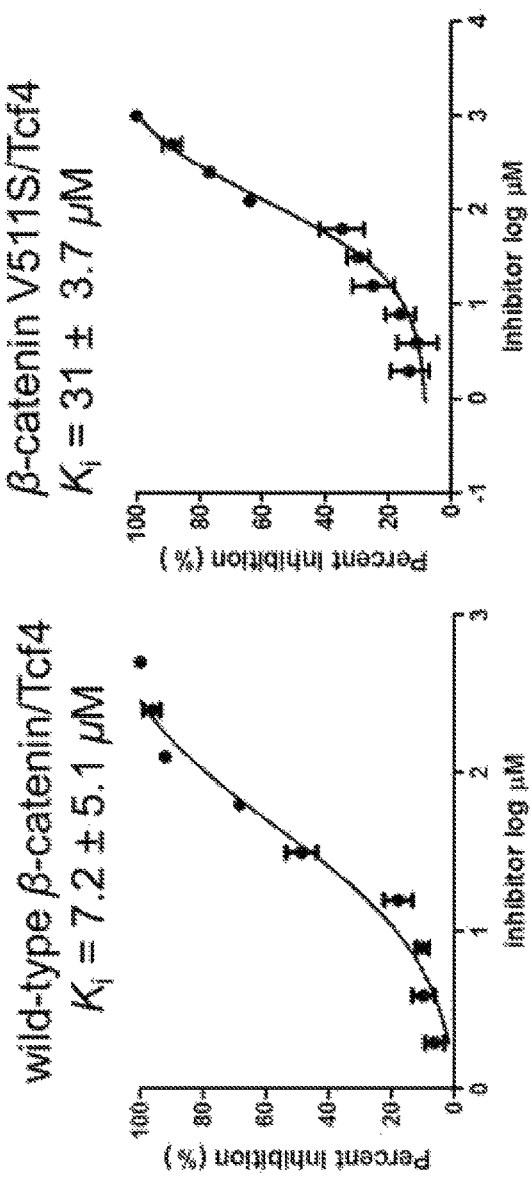
FIG. 13 shows representative data pertaining to site-directed mutagenesis to evaluate the binding mode of compound 26 with β-catenin via FP competitive inhibition assays.
Figure 13:
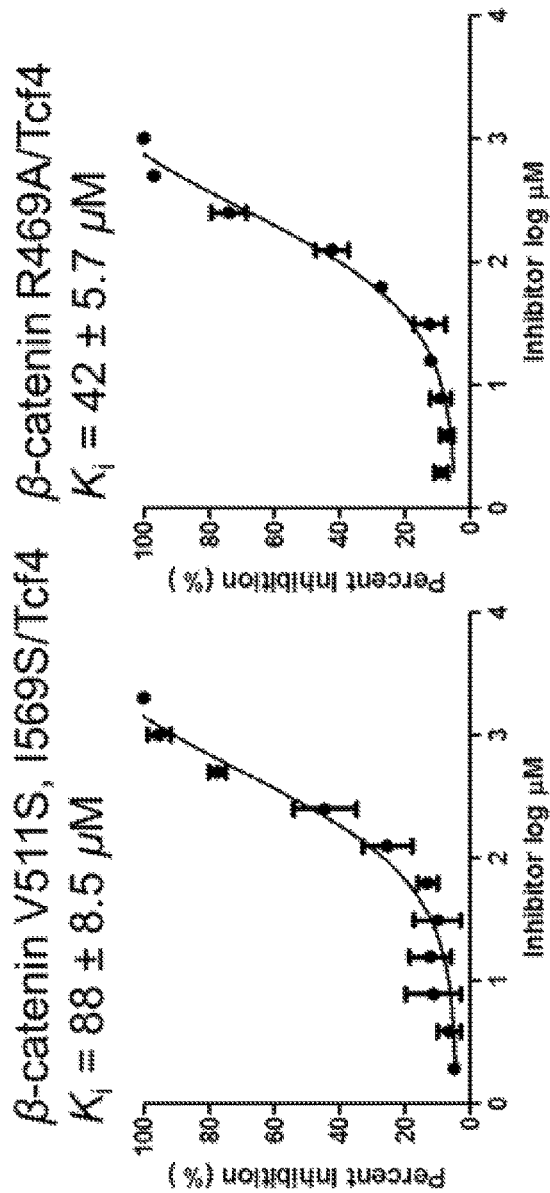

The tetracyclic ring of 18 is not aromatic. Instead, it contains two aromatic substructures, oxadiazolopyrazine and benzene. The imine carbon atom is located at the dibenzylic position and potentially reactive. A nitrogen atom was used to replace this carbon atom. This modification converts the tetracyclic ring into an aromatic system, increases its chemical stability, and maintains the cation-π interaction with $R^{469}$. The hydrazide substructure of 18 was changed to an amide, and 26 was designed. The FP and AlphaScreen assays indicated that the inhibitory activity of 26 was similar to that of 18 (see Table 8). The site-directed mutagenesis study indicated that V511, I569, and R469 are important for the inhibitory activity of 26 (see Table 7, FIG. 12, and FIG. 13).

TABLE 7

| | $K_i \pm SD\ (\mu M)$ | |
|---|---|---|
| | Cmpd. 18 | Cmpd. 26 |
| Wild type | 7.0 ± 4.1 | 7.2 ± 5.1 |
| V511S | 2.0E1 ± 1.7 | 31 ± 3.7 |
| V511S/I569S | 36 ± 3.1 | 88 ± 8.5 |
| R469A | 46 ± 4.3 | 42 ± 5.7 |

Figure 14:
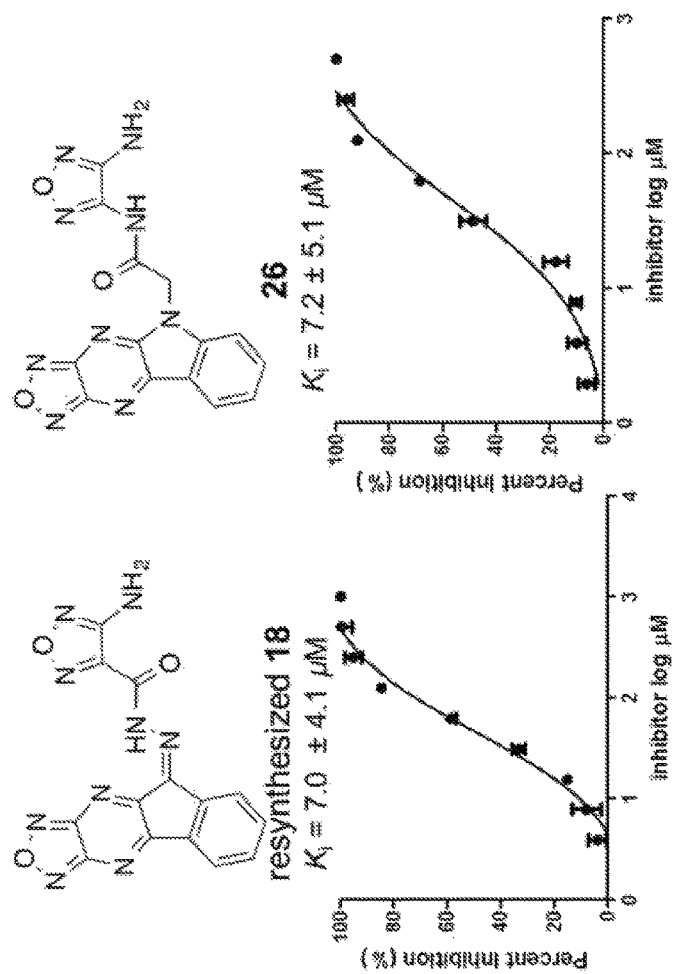
FIG. 14 shows representative data pertaining to the FP competitive inhibition assay results of the resynthesized 18 and 26-38 for the inhibition of the β-catenin/Tcf4 PPI.
Figure 14:
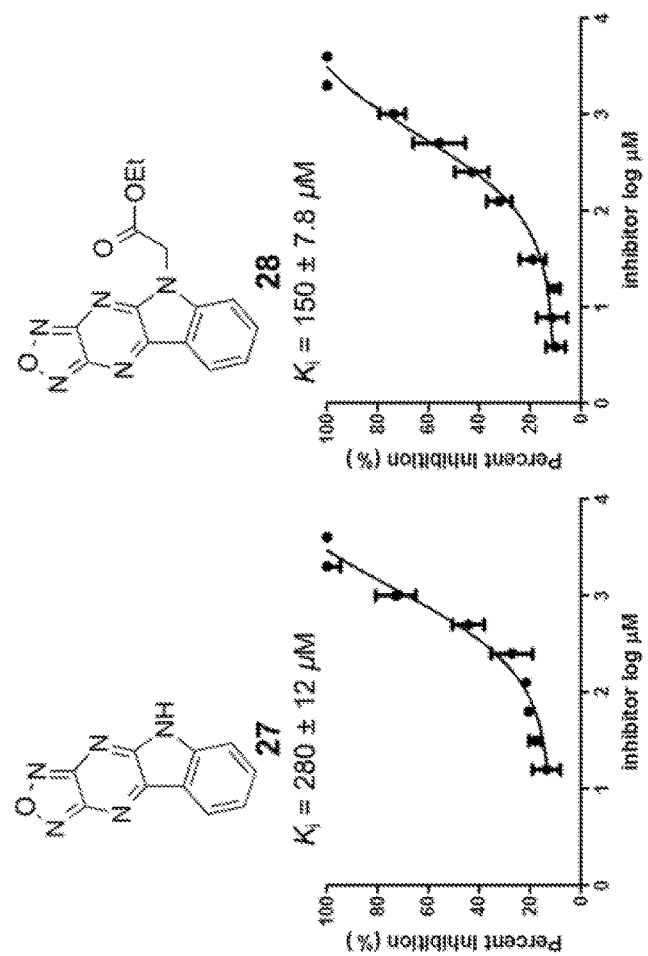
Figure 14:
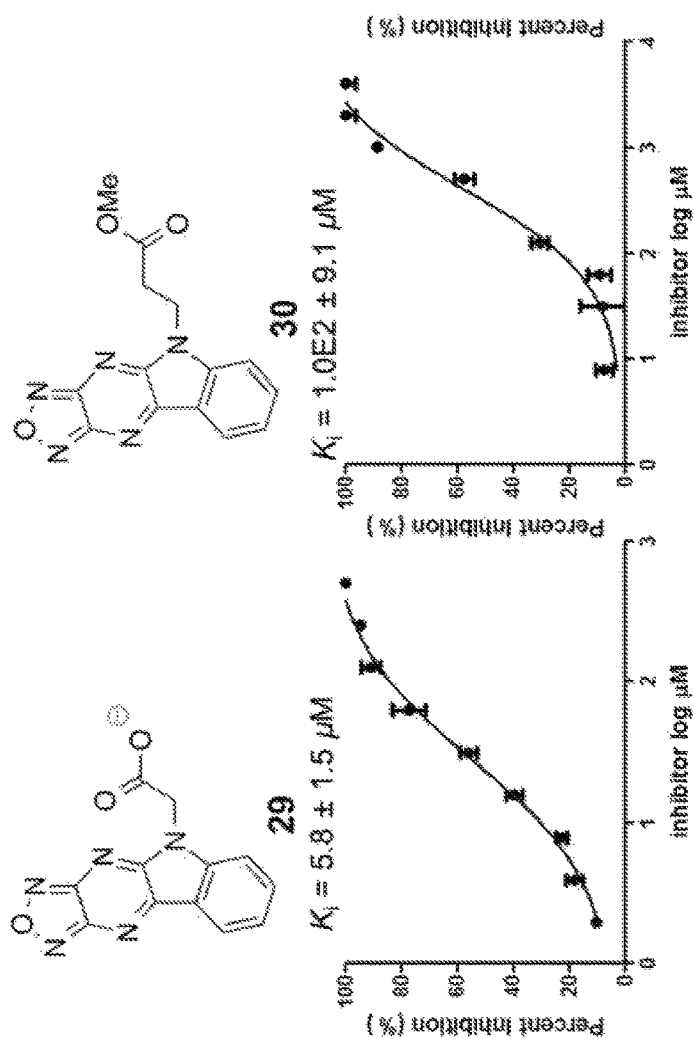
Figure 14:
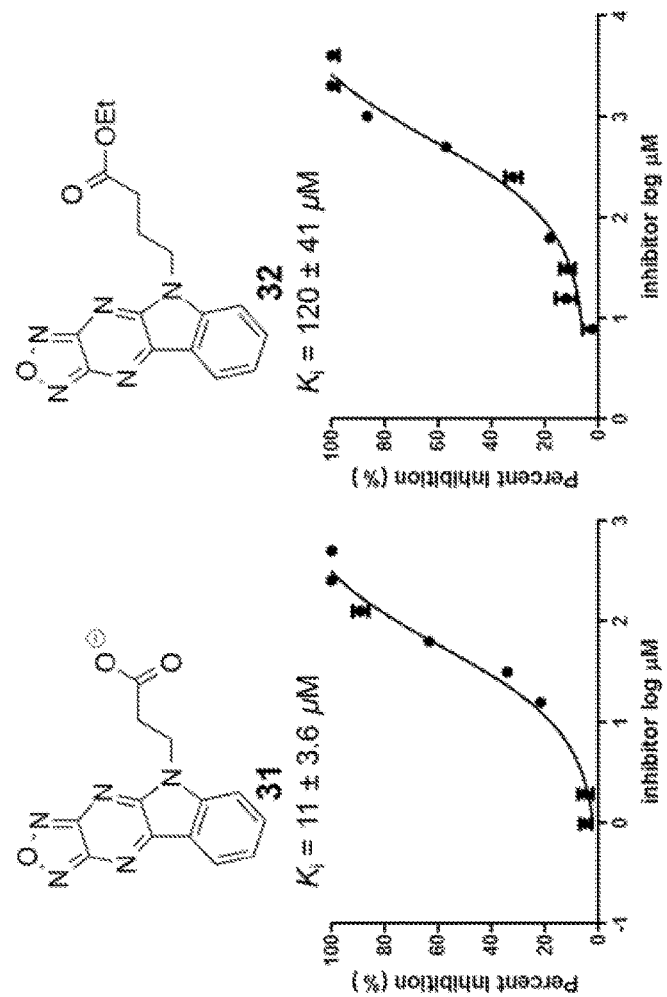
Figure 14:
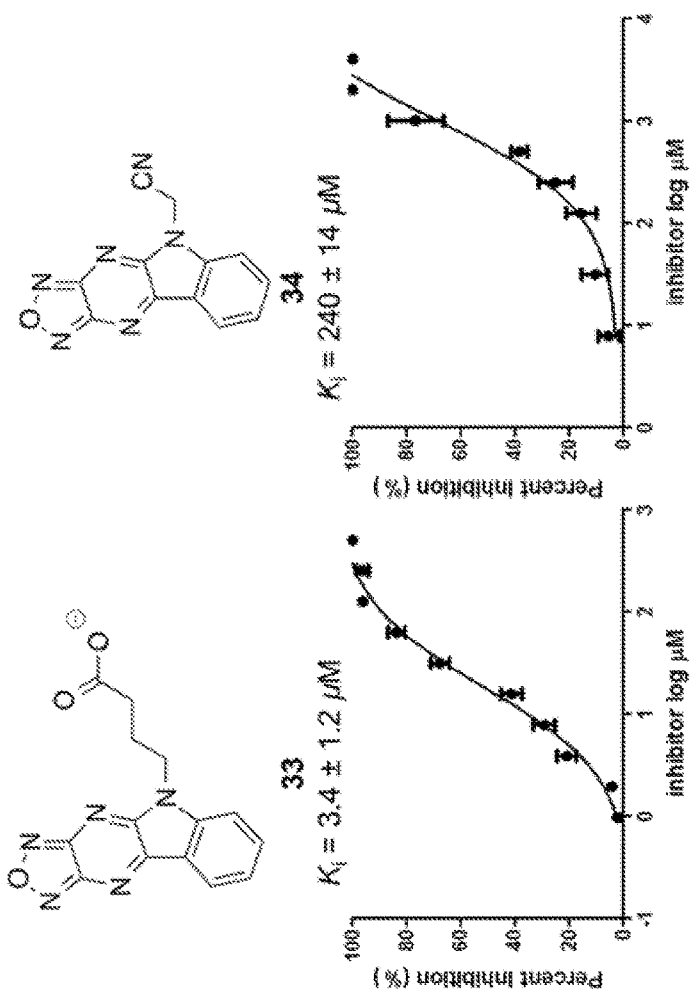
Figure 14:
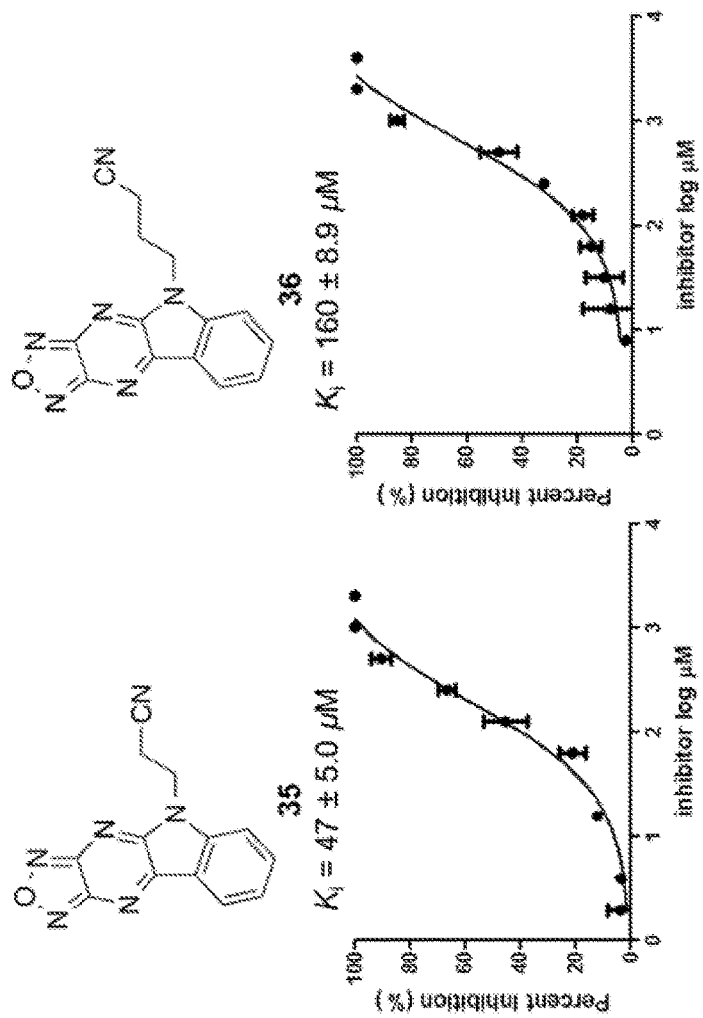
Figure 14:
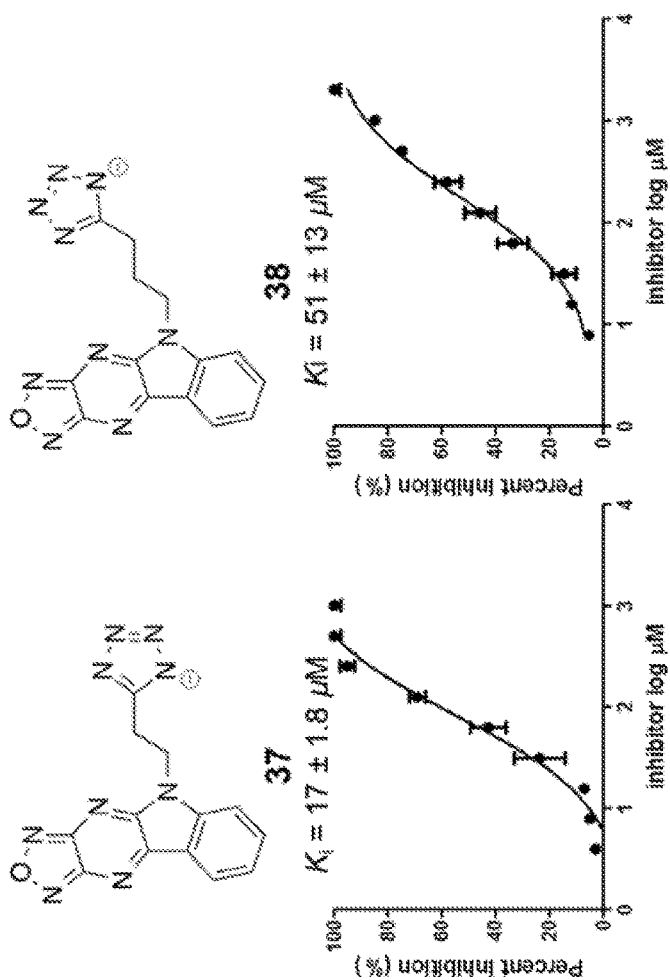
Figure 15:
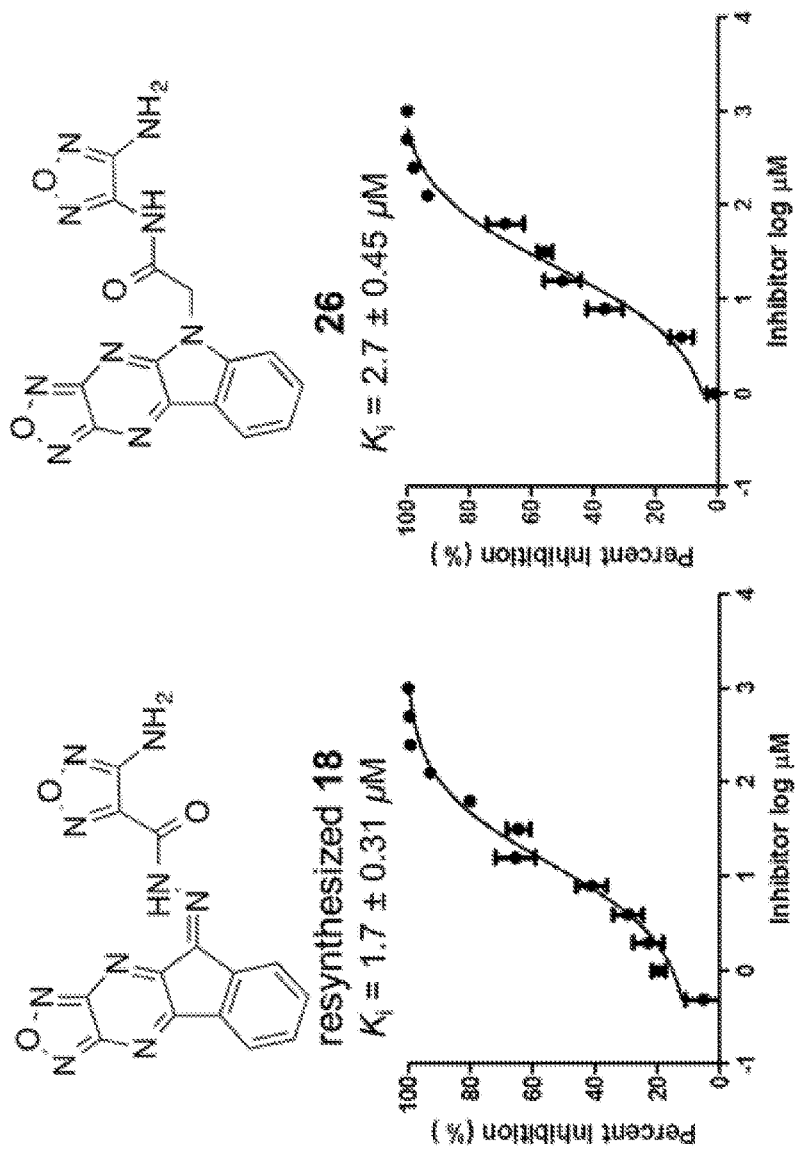
FIG. 15 shows representative data pertaining to the AlphaScreen competitive inhibition assay results of the resynthesized 18, 26-33, and 35-38 for the inhibition of the β-catenin/Tcf4 PPI.
Figure 15:
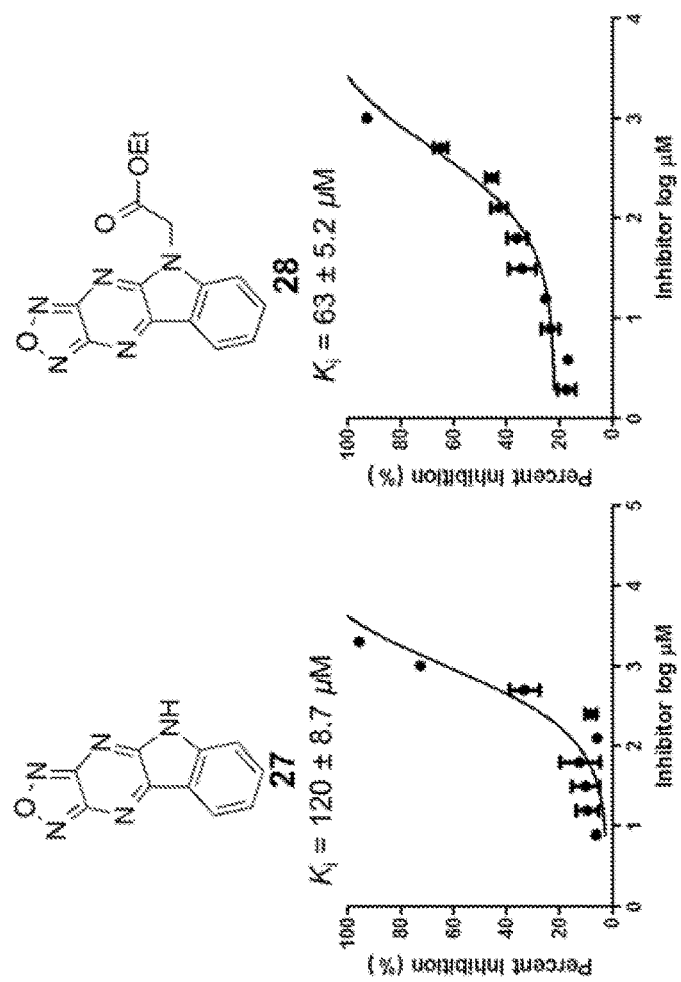
Figure 15:
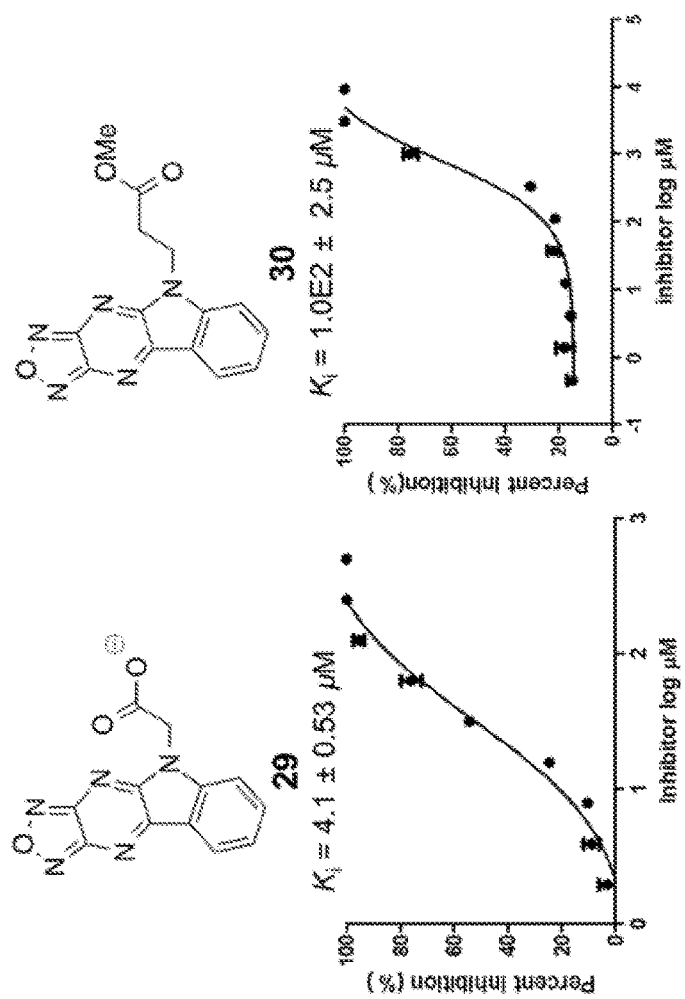
Figure 15:
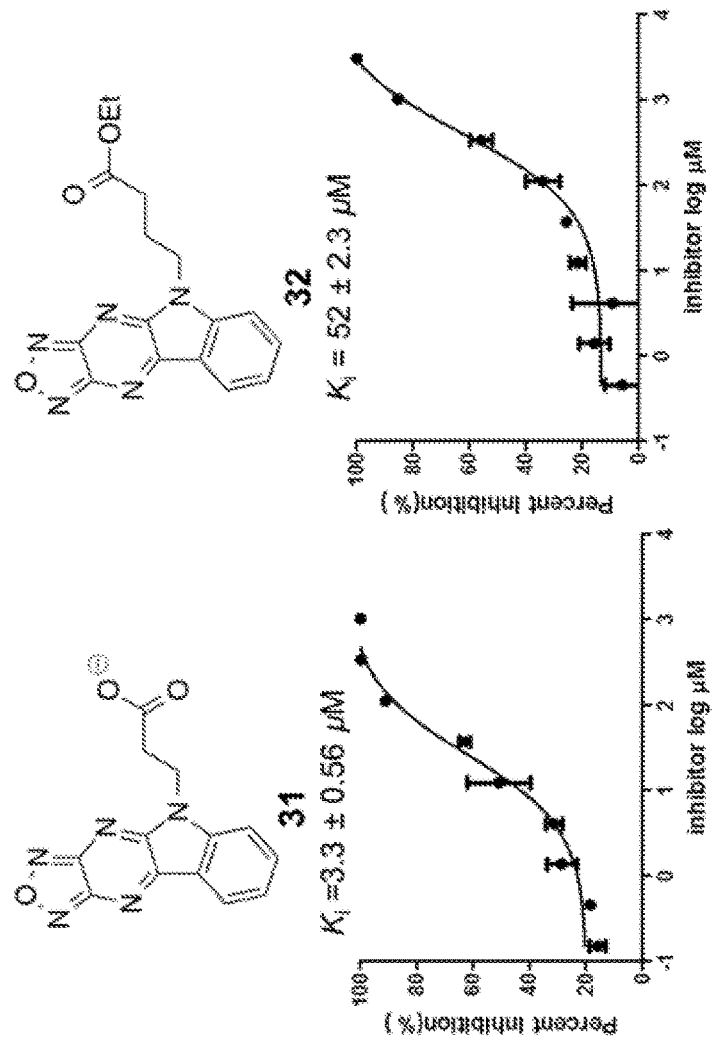
Figure 15:
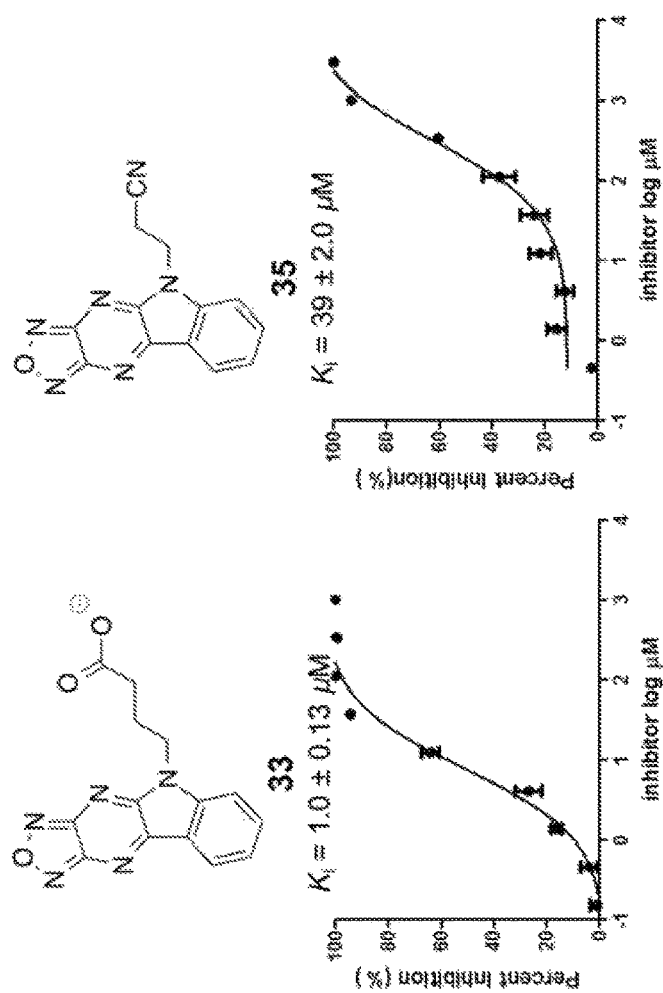
Figure 15:
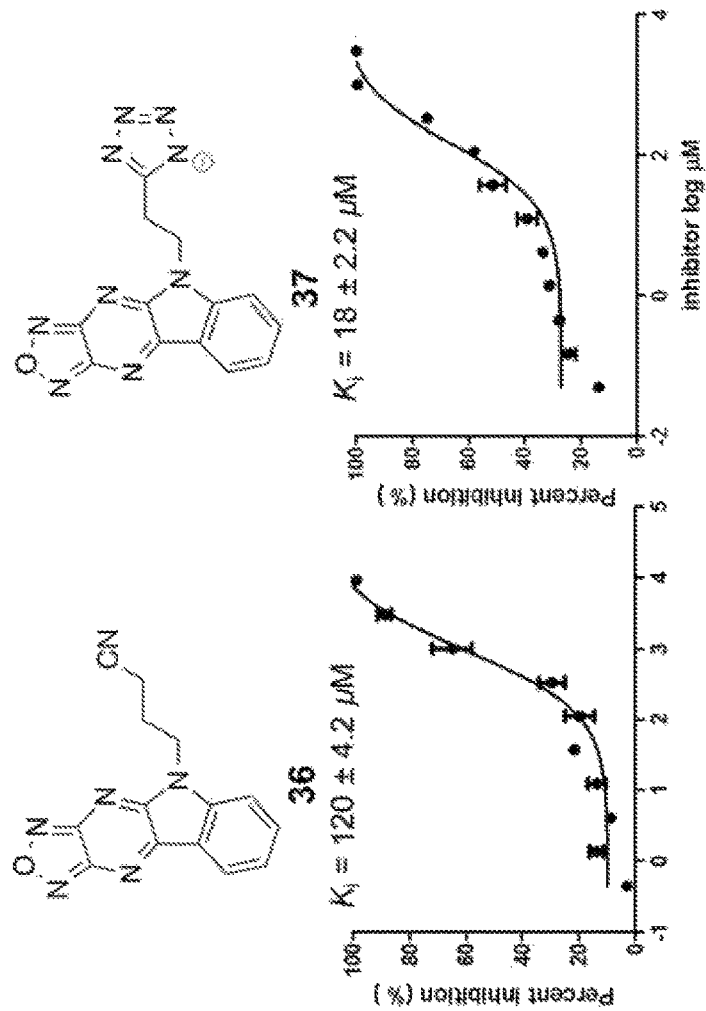
Figure 15:
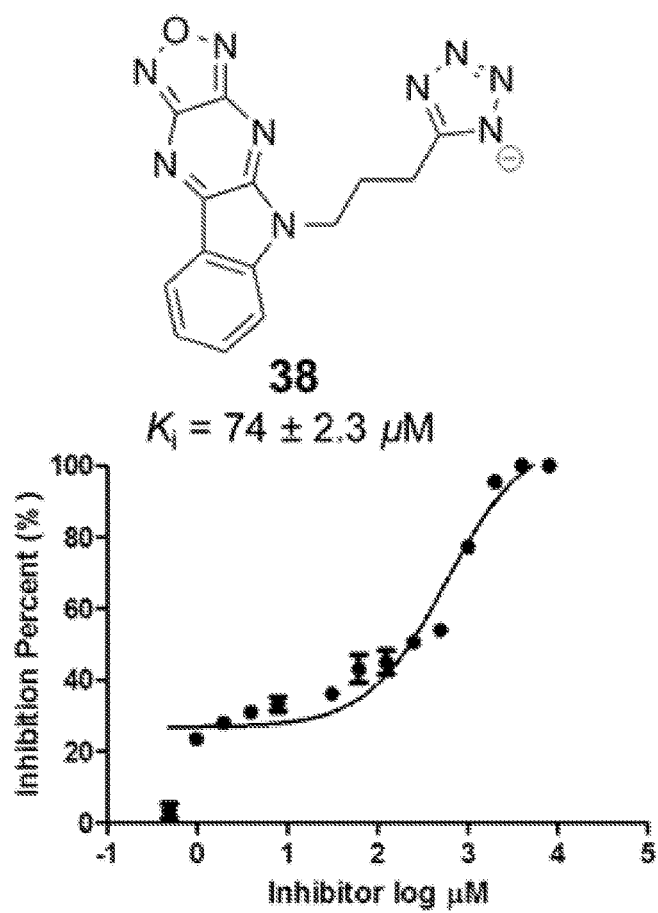

Compounds 27-38 were designed to evaluate the contribution of the 4-amino-1,2,5-oxadiazole ring to inhibitor potency (see Table 2). Without a side chain, compound 27 showed poor inhibitory potency. Compounds 29, 31, and 33, which carboxylic acid side chains were predicted to form charge-charge interactions with charge button K435, exhibited a much higher inhibitory potency. Their methyl or ethyl esters (compounds 28, 30, and 32) were poor inhibitors. The nitrile derivatives, 34-36, also exhibited poor inhibitory activity. When the nitrile group was converted to a tetrazole moiety (compounds 37 and 38), a bioisostere of carboxylic acid, the inhibitory potency was improved. Among these inhibitors, compound 33 exhibited the highest inhibitory potency for the β-catenin/Tcf PPI in the biochemical assays (see Table 8, FIG. 14, and FIG. 15).

TABLE 8

| Cmpd. | $K_i \pm SD\ (\mu M)$ | |
|---|---|---|
| No. | FP | AlphaScreen |
| 18 | 7.0 ± 4.1 | 1.7 ± 0.31 |
| 26 | 7.2 ± 5.1 | 2.7 ± 0.45 |
| 27 | 280 ± 12 | 120 ± 8.7 |
| 28 | 150 ± 7.8 | 63 ± 5.2 |
| 29 | 5.8 ± 1.5 | 4.1 ± 0.53 |
| 30 | 1.0E2 ± 9.1 | 1.0E2 ± 2.5 |
| 31 | 11 ± 3.6 | 3.3 ± 0.56 |
| 32 | 120 ± 4.1 | 52 ± 2.3 |
| 33 | 3.4 ± 1.2 | 1.0 ± 0.13 |
| 34 | 240 ± 14 | >130 |
| 35 | 47 ± 5.0 | 3 ± 2.0 |
| 36 | 160 ± 8.9 | 120 ± 4.2 |
| 37 | 17 ± 1.8 | 18 ± 2.2 |
| 38 | 51 ± 13 | 74 ± 2.3 |

Figure 16:
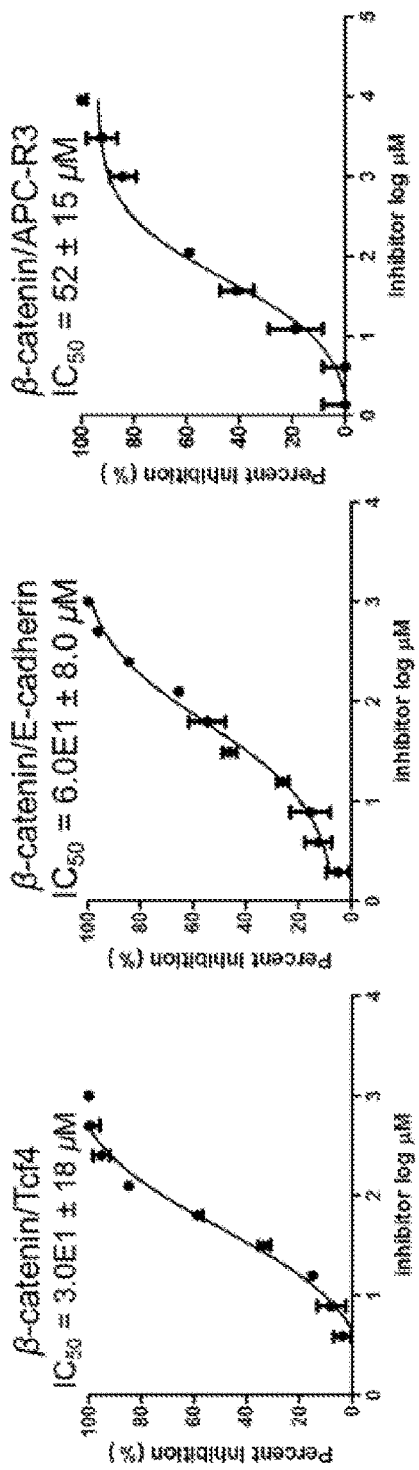
FIG. 16 shows representative data pertaining to the FP competitive inhibition assay to determine inhibitor selectivity of 18, 26, 29, 31, 33, and 37 for β-catenin/Tcf over β-catenin/cadherin and β-catenin/APC PPIs.
Figure 16:
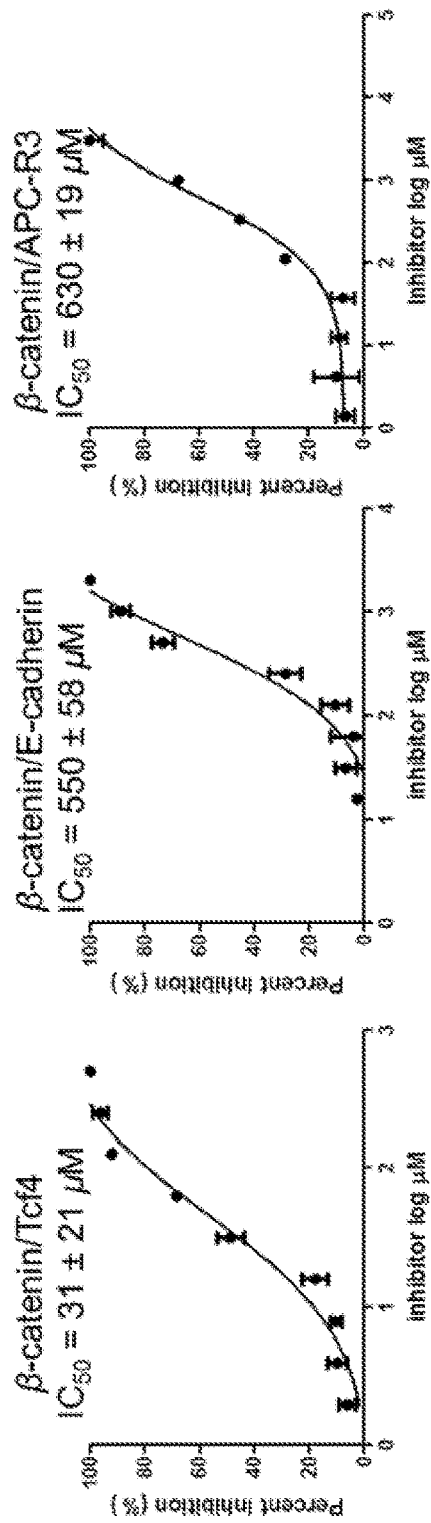
Figure 16:
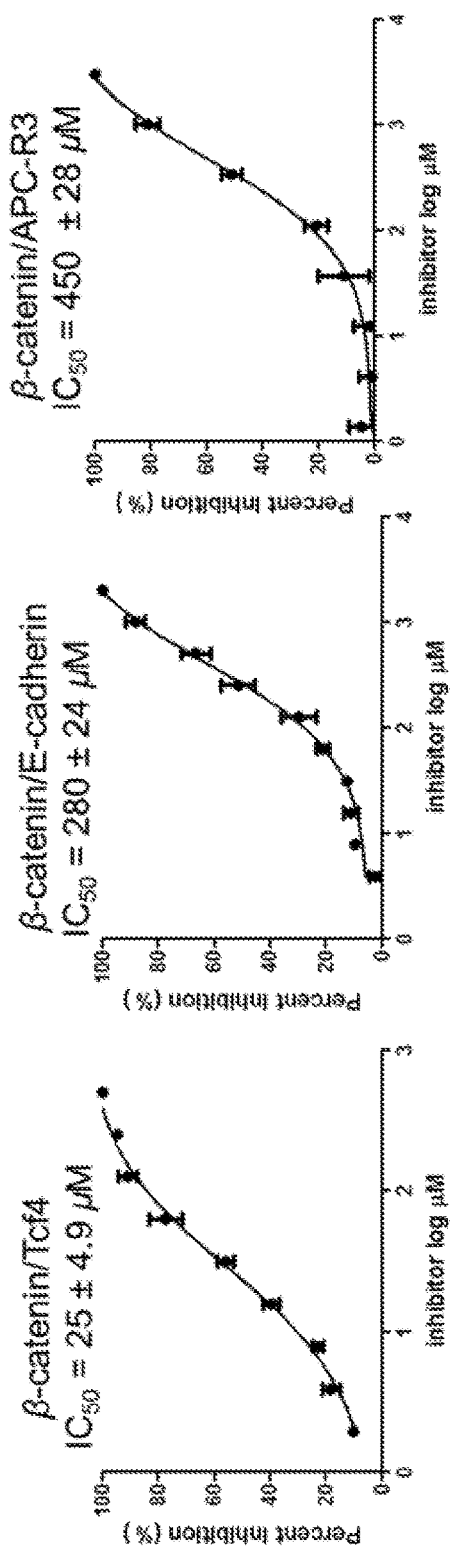
Figure 16:
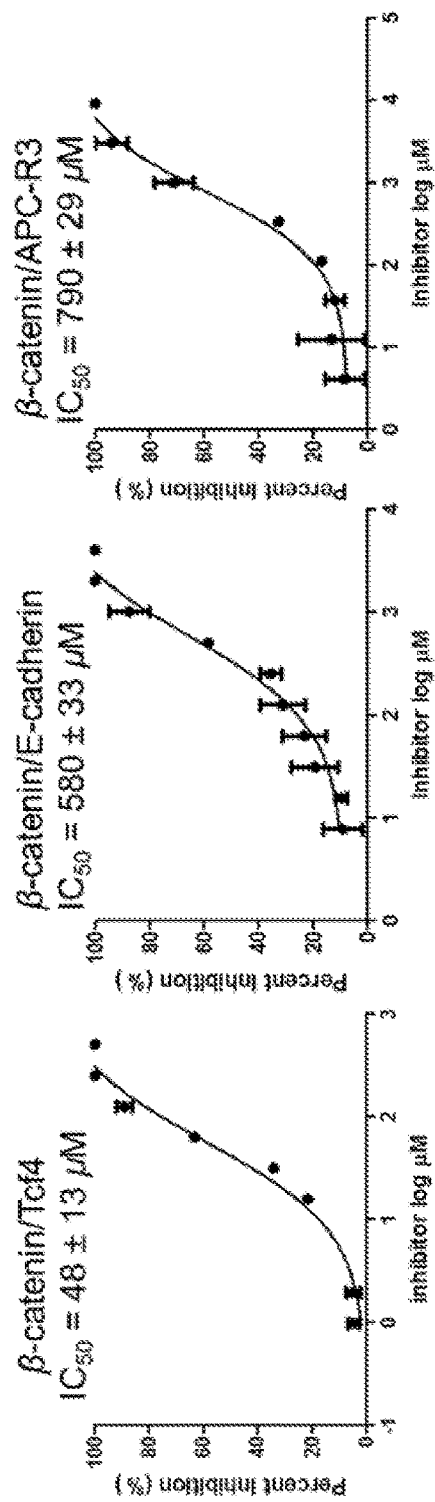
Figure 16:
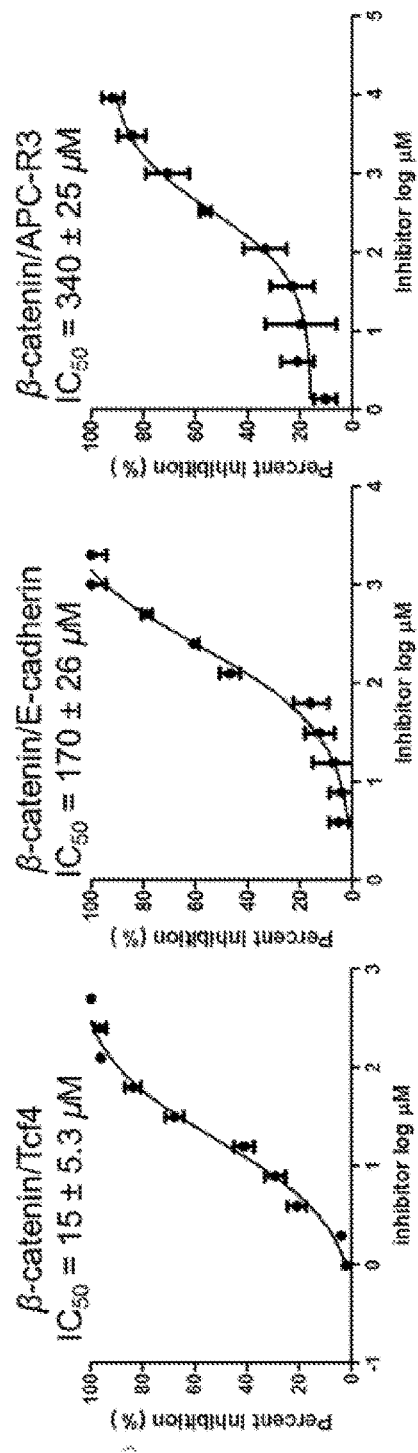
Figure 16:
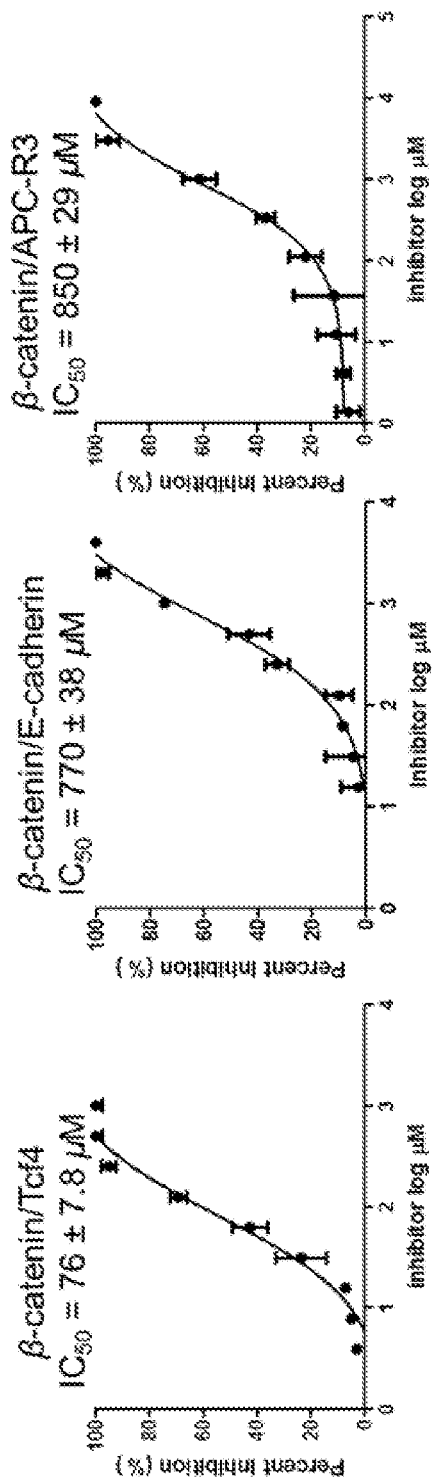
Figure 17B:
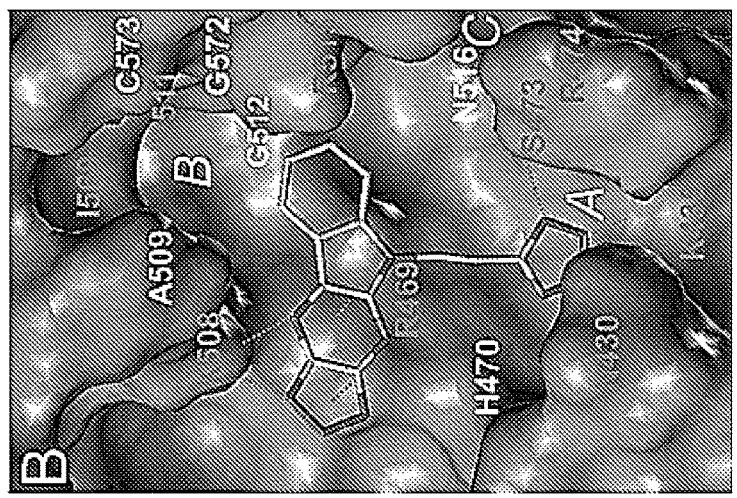
FIG. 17A and FIG. 17B show representative Glide docking models (FIG. 17A and FIG. 17B) and stick models (FIG. 17C and FIG. 17D) of compounds 33 and 37 with β-catenin.
Figure 17A:
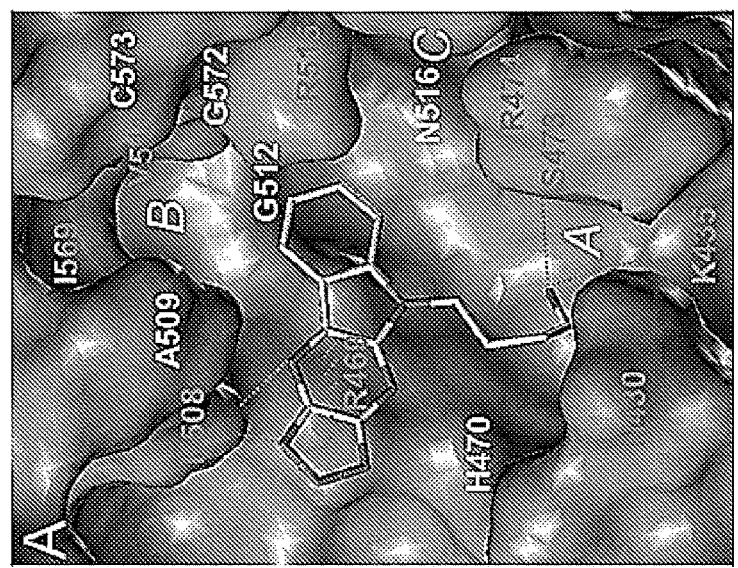
Figure 17D:
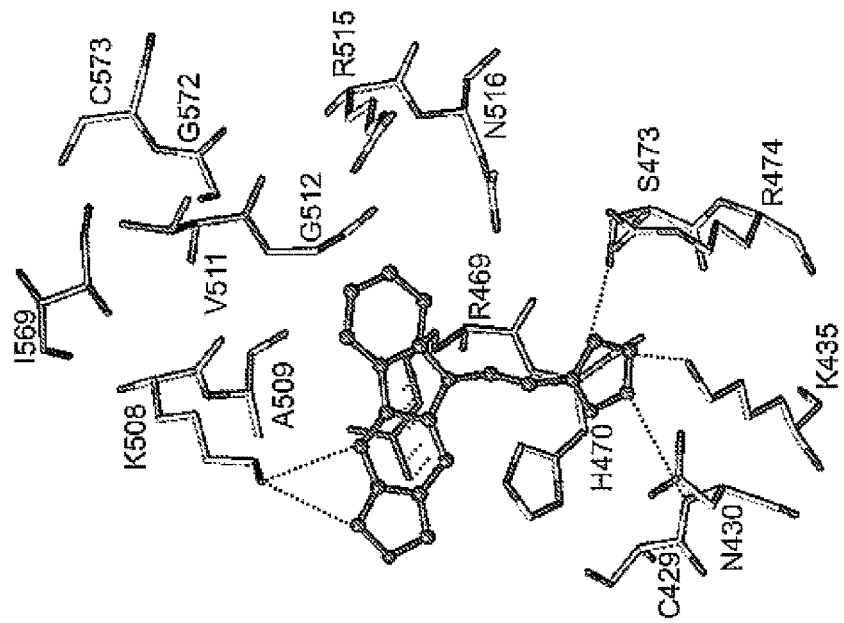
Figure 17C:
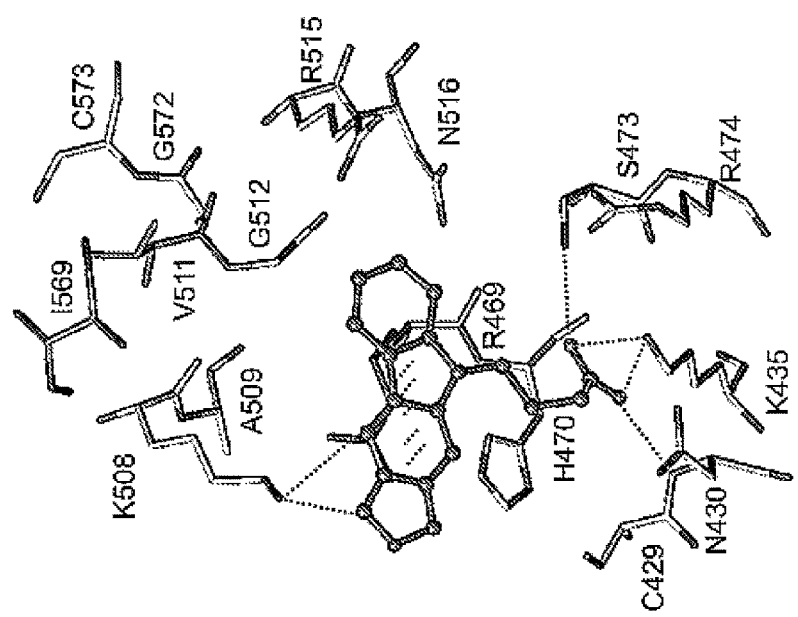

The FP selectivity assay (Zhang et al. (2013) *ACS Med. Chem. Lett.* 4, 306-311) was used to quantify inhibitor selectivities between β-catenin/Tcf, β-catenin/E-cadherin, and β-catenin/APC PPIs. The results are illustrated in Table 9 and FIG. 16. Compounds 26, 29, 31, 33, and 37 show dual selectivity for β-catenin/Tcf over β-catenin/cadherin and β-catenin/APC PPIs. Compound 18 exhibits marginal selectivity among these three PPIs, again implying off-target effects. The selectivity of known 6-catenin/Tcf inhibitors is also listed for comparison (Huang et al. (2014) *ACS Chem. Biol.* 9, 193-201; Zhang et al. (2013) *ACS Med. Chem. Lett.* 4, 306-311). The data in Table 9 reflect inhibitory potency under the assay conditions used. More analysis will be required to fully understand the selectivity of the inhibitors for β-catenin/Tcf over β-catenin/cadherin and β-catenin/APC PPIs.

TABLE 9

| | $K_i \pm SD\ (\mu M)$ | | |
|---|---|---|---|
| Cmpd. No. | β-catenin/Tcf4 | β-catenin/E-cadherin | β-catenin/APC-R3 |
| 18 | 3.01E1 ± 18 | 6.0E1 ± 8.0 | 52 ± 15 |
| 26 | 31 ± 21 | 550 ± 58 | 630 ± 19 |
| 29 | 25 ± 4.9 | 280 ± 24 | 450 ± 28 |
| 31 | 48 ± 13 | 580 ± 33 | 790 ± 29 |
| 33 | 15 ± 5.3 | 170 ± 26 | 340 ± 25 |
| 37 | 76 ± 7.8 | 770 ± 38 | 850 ± 29 |
| 1$^a$ | 77 ± 9.3 | 38 ± 1.6 | 110 ± 0.58 |
| 2$^a$ | 150 ± 19 | 41 ± 1.6 | 130 ± 0.38 |
| 3$^a$ | 3.0E1 ± 1.5 | 34 ± 0.75 | 340 ± 0.70 |
| 13$^a$ | 13 ± 2.4 | 3.0E2 ± 1.3 | 350 ± 1.9 |
| 14$^b$ | 6.3 ± 0.76 | 680 ± 6.8 | 210 ± 3.0 |

$^a$Roubinek et al. (1984) *Collect. Czech. Chem. Commun.* 49, 285-294;
$^b$Huang et al. (2014) *ACS Chem. Biol.* 9, 193-201.

Figure 18:
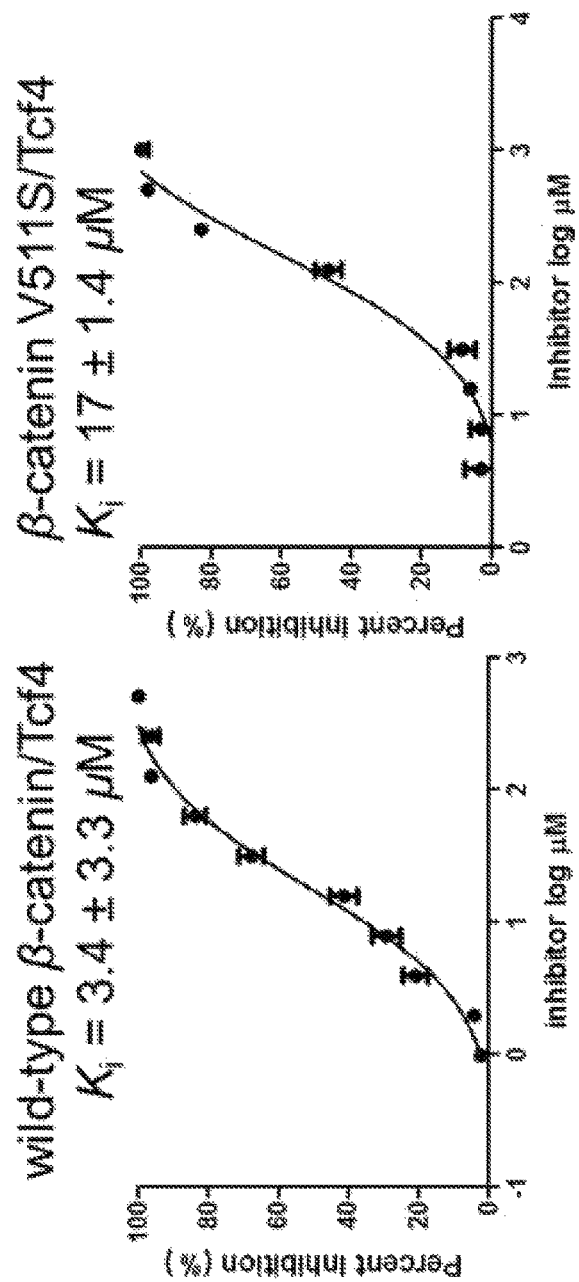
FIG. 18 shows representative data pertaining to site-directed mutagenesis to evaluate the binding mode of compounds 33 and 37 with β-catenin via FP competitive inhibition assays.
Figure 18:
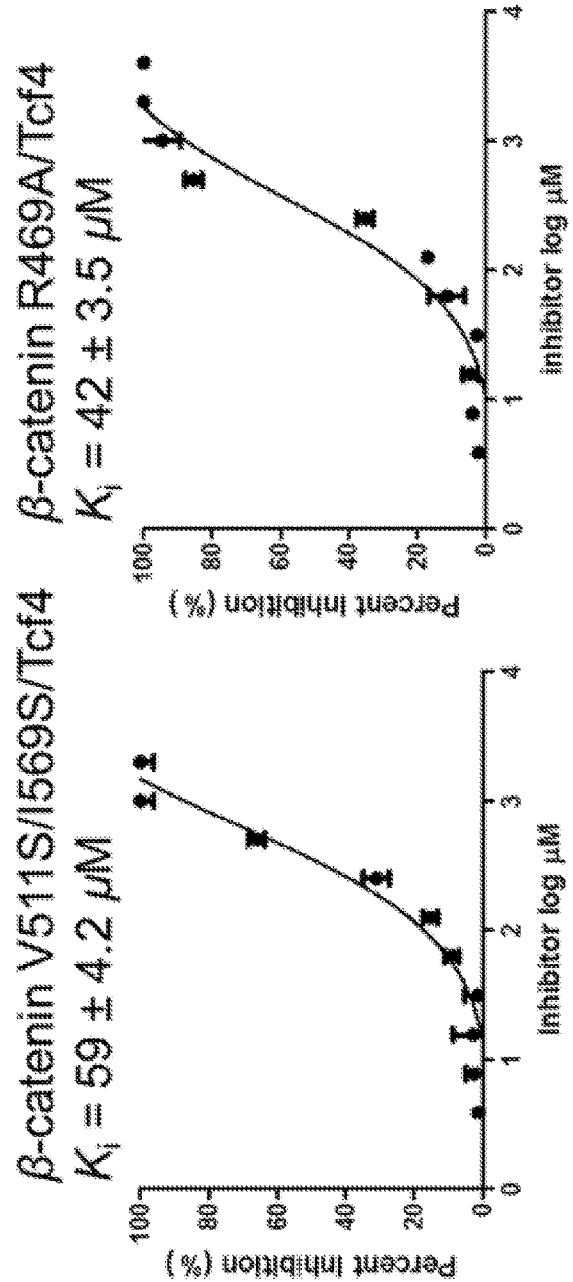
Figure 18:
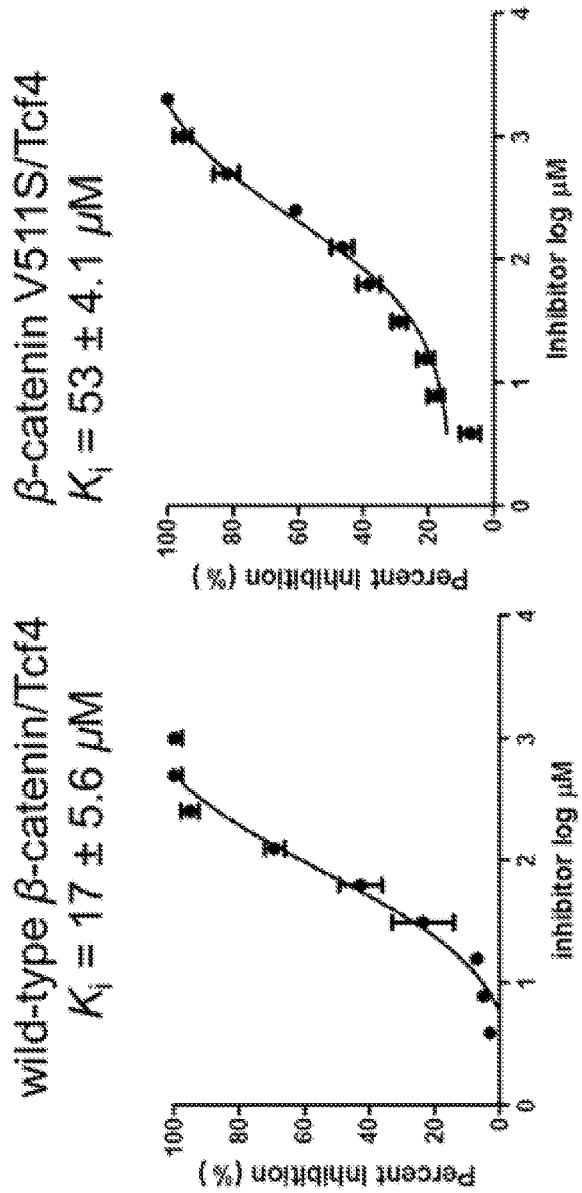
Figure 18:
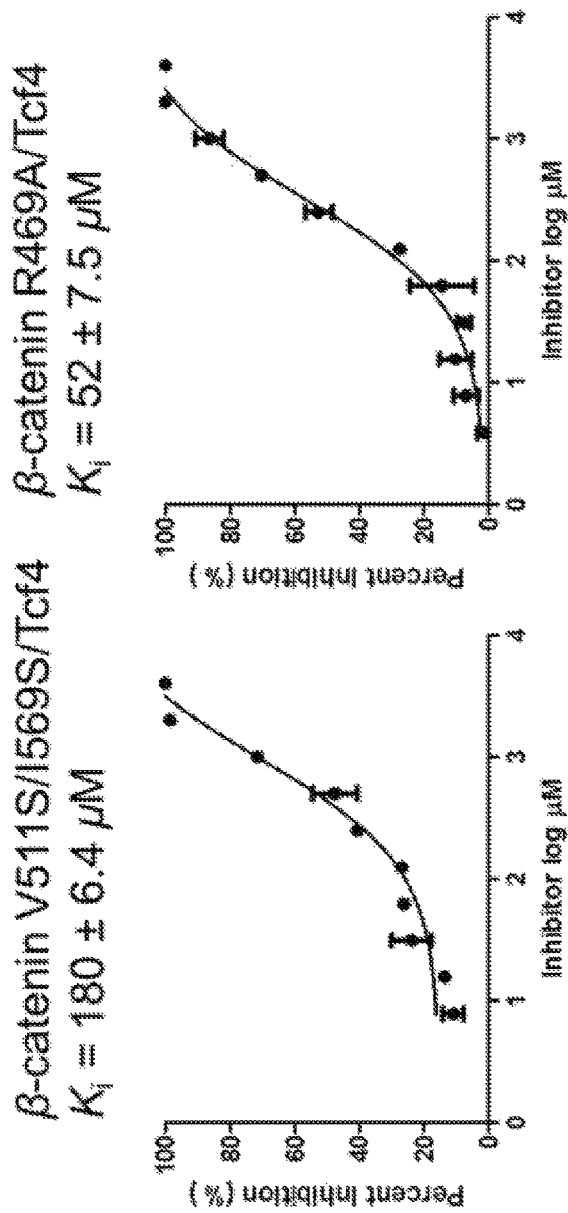

5. Biological Characterization of the Derivatives of 18 as β-Catenin/Tcf Inhibitors The Glide docking mode of 33 and 37 with β-catenin is shown in FIG. 17A, FIG. 17B, FIG. 17C, and FIG. 17D. The tetracyclic ring of 33 and 37 was predicted to form a cation-π interaction with the positively charged gaunidino group of R469. The benzene moiety of the tetracyclic ring was predicted to locate in hydrophobic pocket B. Two nitrogen atoms of the oxadiazolopyrazine ring of 33 and 37 were predicted to form H-bonds with K508. The carboxylic group of 33 and the tetrazole ring of 37 were predicted to form a salt bridge with K435 and H-bonds with the backbone NH group of N470 and the hydroxyl group of S473. Site-directed mutagenesis was performed to evaluate the contribution of three residues, R469, V511, and I516, to inhibitor potency. The results are illustrated in Table 10 and FIG. 18. The $K_i$ value of 33 for the wild-type β-catenin/wild-type Tcf4 interaction was 3.4±3.3 μM. The $K_i$ values of 33 for β-catenin V511S mutant/wild-type Tcf4, β-catenin V511S/I569S double mutant/wild-type Tcf4, and β-catenin R469A mutant/wild-type Tcf4 interactions were 17±1.4 μM, 59±4.2 μM, and 42±3.5 μM, respectively. The same trend was also observed for 37. Without wishing to be bound by theory, these results suggest the hydrophobicity in pocket B and the positively charged side chain of β-catenin R469 may be important for the inhibitory potency of 33 and 37.

TABLE 10

| Cmpd. | $K_i \pm SD\ (\mu M)$, β-catenin | | | |
|---|---|---|---|---|
| No. | Wild type | V511S | V511S/I569S | R469A |
| 33 | 3.4 ± 3.3 | 17 ± 1.4 | 59 ± 4.2 | 42 ± 3.5 |
| 37 | 17 ± 5.6 | 53 ± 4.1 | 180 ± 6.4 | 52 ± 7.5 |

Figure 19A:
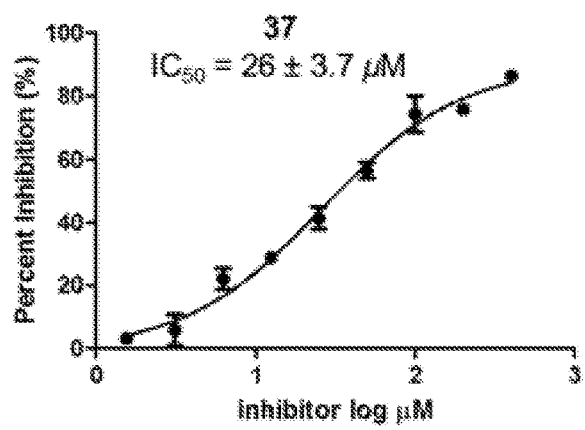
FIGS. 19A-C show representative data pertaining to the cell-based characterization of compound 37 as a β-catenin/Tcf inhibitor.
Figure 19B:
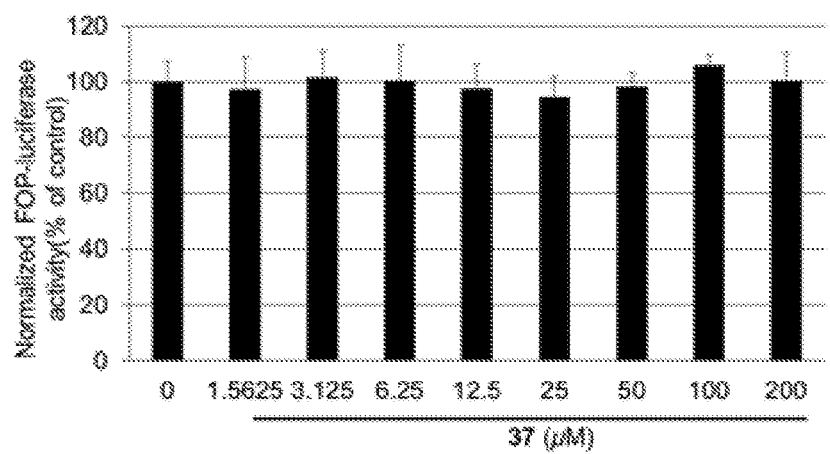
Figure 19C:
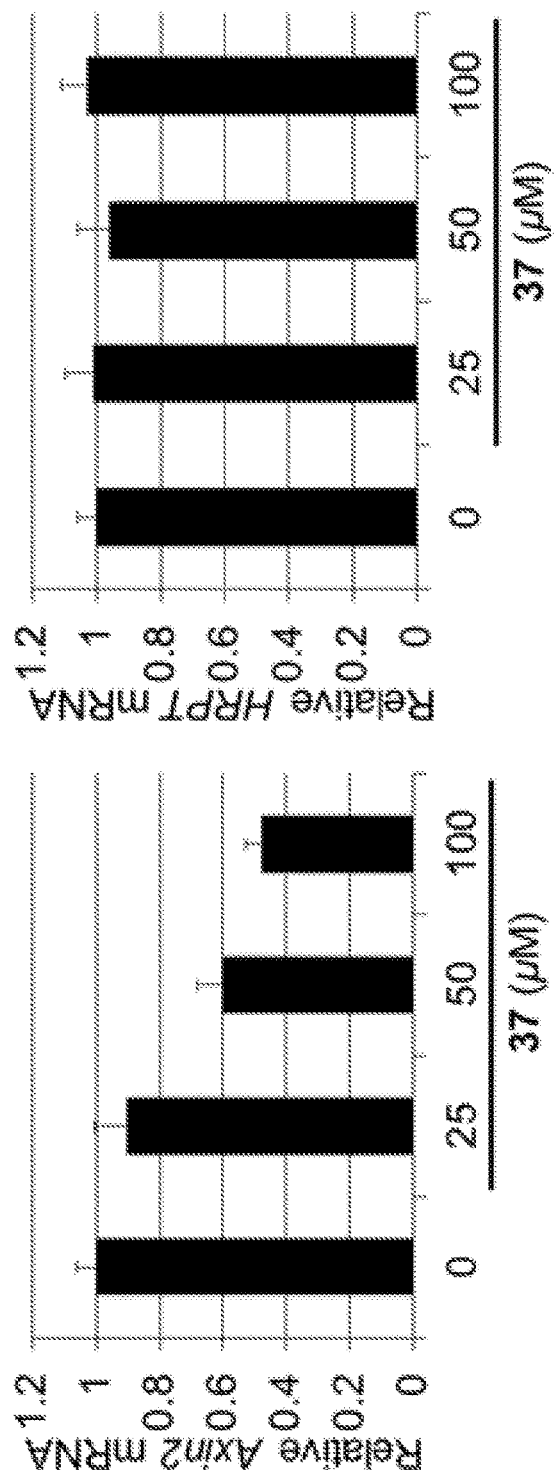

The Wnt-responsive luciferase reporter assay was performed with pcDNA3.1-β-catenin transfected HEK293 cells for 26, 30, 32, 33 and 37. Compounds 26, 30, 32 and 33 did not inhibit the transactivation of canonical Wnt signaling presumably due to low cell permeability. However, compound 37 suppressed the TOPFlash luciferase activity in a dose-dependent manner, as shown in FIG. 19A. This compound did not affect the FOPFlash luciferase activity even at 200 μM (FIG. 19B). Compound 37 also down-regulated the expression of Wnt-specific target gene AXIN2 in a dose-dependent manner in SW480 cells (FIG. 19C). The same trend was also observed for the inhibition of two other target genes, cyclin D1 and c-myc. This compound did not affect the expression of house-keeping gene HPRT in the parallel assay. The MTs cell viability assay was performed to assess the inhibitory effects of 26, 30, 32, 33, 35, and 37 on the growth of colorectal cell lines SW480 and HCT116. Compounds 26, 30, 32, and 33 did not exhibit the inhibitory activities. Compound 35 inhibited the growth of SW480 but not HCT116 cells. Compound 37 inhibited the growth of Wnt-activated cancer cells with the $IC_{50}$ values of 2.0E1±4.1 µM and 31±6.0 µM for SW480 and HCT116 cells, respectively, as shown in Table 11.

Referring to FIG. 19A and FIG. 19B, TOPFlash and FOPFlash luciferase reporter assay results of compound 37 using pcDNA3.1-β-catenin transfected HEK293 cells are shown. The data is expressed as mean±standard deviation (n=3).

Referring to FIG. 19C, a quantitative real time PCR study was used to determine the changes of mRNA expression of AXIN2 and HPRT in response to different concentrations of 37. Each set of data is expressed as mean±standard deviation (n=3).

TABLE 11

| Cmpd. No. | $K_i$ ± SD (µM), β-catenin | |
|---|---|---|
| | SW480 | HCT116 |
| 35 | 52 ± 3.7 | >2.0E2 |
| 37 | 2.0E1 ± 4.1 | 31 ± 6.0 |

H. REFERENCES

Cousins, G. R. L.; Poulsen S.-A.; Sanders, J. K. M. Dynamic combinatorial libraries of pseudo-peptide hydrazone macrocycles. *Chem. Commun.* 1999, 1575-1576.

Poulsen, S.-A. Direct screening of a dynamic combinatorial library using mass spectrometry. *J. Am. Soc. Mass Spectrom.* 2006, 17, 1074-1080.

Bhat, V. T.; Caniard, A. M.; Luksch, T.; Brenk, R.; Campopiano, D. J.; Greaney, M. F. Nucleophilic catalysis of acylhydrazone equilibration for protein-directed dynamic covalent chemistry. *Nat. Chem.* 2010, 2, 490-497.

Bunyapaiboonsri, T.; Ramström, O.; Lohmann, S.; Lehn, J.-M.; Peng, L.; Goeldner, M. Dynamic deconvolution of a pre-equilibrated dynamic combinatorial library of acetylcholinesterase inhibitors. *ChemBioChem* 2001, 2, 438-444.

Bunyapaiboonsri, T.; Ramström, H.; Ramström, O.; Haiech, J.; Lehn, J.-M. Generation of bis-cationic heterocyclic inhibitors of *Bacillus subtilis* HPr kinase/phosphatase from a ditopic dynamic combinatorial library. *J. Med. Chem.* 2003, 46, 5803-5811.

Mondal, M.; Radeva, N.; Köster, H.; Park, A.; Potamitis, C.; Zervou, M.; Klebe, G.; Hirsch, A. K. H. Structure-based design of inhibitors of the aspartic protease endothiapepsin by exploiting dynamic combinatorial chemistry. *Angew. Chem. Int. Ed.* 2014, 53, 3259-3263.

Jiang, Q.-Q.; Sicking W.; Ehlers, M.; Schmuck, C. Discovery of potent inhibitors of human β-tryptase from pre-equilibrated dynamic combinatorial libraries. *Chem. Sci.* 2015, ASAP. DOI: 10.1039/c4sc02943g.

Wang, L.; Zuercher, W. J.; Consler, T. G.; Lambert, M. H.; Miller, A. B.; Orband-Miller, L. A.; McKee, D. D.; Willson, T. M.; Nolte, R. T. X-ray crystal structures of the estrogen-related receptor-γ ligand binding domain in three functional states reveal the molecular basis of small molecule regulation. *J. Biol. Chem.* 2006, 281, 37773-37781.

Zhang, L.; Liu, W.; Hu, T.; Du, L.; Luo, C.; Chen, K.; Shen, X.; Jiang, H. Structural basis for catalytic and inhibitory mechanisms of β-hydroxyacyl-acyl carrier protein dehydratase (FabZ). *J. Biol. Chem.* 2008, 283, 5370-5379.

He, L.; Zhang, L.; Liu, X.; Li, X.; Zheng, M.; Li, H.; Yu, K.; Chen, K.; Shen, X.; Jiang, H.; Liu, H. Discovering potent inhibitors against the β-hydroxyacyl-acyl carrier protein dehydratase (FabZ) of *Helicobacter pylori*: structure-based design, synthesis, bioassay, and crystal structure determination. *J. Med. Chem.* 2009, 52, 2465-2481.

Dai, R.; Wilson, D. J.; Geders, T. W.; Aldrich, C. C.; Finzel, B. C. Inhibition of *Mycobacterium tuberculosis* transaminase BioA by aryl hydrazines and hydrazides. *ChemBioChem* 2014, 15, 575-586.

Mondal, M.; Radeva, N.; Köster, H.; Park, A.; Potamitis, C.; Zervou, M.; Klebe, G.; Hirsch, A. K. H. Structure-based design of inhibitors of the aspartic protease endothiapepsin by exploiting dynamic combinatorial chemistry. *Angew. Chem. Int. Ed.* 2014, 53, 3259-3263.

Baell, J. B.; Holloway, G. A. New substructure filters for removal of pan assay interference compounds (PAINS) from screening libraries and for their exclusion in bioassays. *J. Med. Chem.* 2010, 53, 2719-2740.

Malvezzi, A.; de Rezende, L.; Izidoro, M. A.; Cezari, M. H. S.; Juliano, L.; do Amaral A. T. Uncovering false positives on a virtual screening search for cruzain inhibitors. *Bioorg. Med. Chem. Lett.* 2008, 18, 350-354.

Narang, R.; Narasimhan, B.; Sharma, S. A review on biological activities and chemical synthesis of hydrazide derivatives. *Curr. Med. Chem.* 2012, 19, 569-612.

Clevers, H.; Nusse, R. Wnt/β-catenin signaling and disease. *Cell* 2012, 149, 1192-1205.

Klaus, A.; Birchmeier, W. Wnt signaling and its impact on development and cancer. *Nat. Rev. Cancer* 2008, 8, 387-398.

Tetsu, O.; McCormick, F. β-Catenin regulates expression of cyclin D1 in colon carcinoma cells. *Nature* 1999, 398, 422-426.

He, T.-C.; Sparks, A. B.; Rago, C.; Hermeking, H.; Zawel, L.; da Costa, L. T.; Morin, P. J.; Vogelstein, B.; Kinzler, K. W. Identification of c-MYC as a target of the APC pathway. *Science* 1998, 281, 1509-1512.

Kim, P. J.; Plescia, J.; Clevers, H.; Fearon, E. R.; Altieri, D. C. Survivin and molecular pathogenesis of colorectal cancer. *Lancet* 2003, 362, 205-209.

Malanchi, I.; Peinado, H.; Kassen, D.; Hussenet, T.; Metzger, D.; Chambon, P.; Huber, M.; Hohl, D.; Cano, A.; Birchmeier, W.; Huelsken, J. Cutaneous cancer stem cell maintenance is dependent on β-catenin signalling. *Nature* 2008, 452, 650-653.

Barker, N.; Ridgway, R. A.; van Es, J. H.; van de Wetering, M.; Begthel, H.; van den Born, M.; Danenberg, E.; Clarke, A. R.; Sansom, O. J.; Clevers, H. Crypt stem cells as the cells-of-origin of intestinal cancer. *Nature* 2009, 457, 608-611.

Yeung, J.; Esposito, M. T.; Gandillet, A.; Zeisig, B. B.; Griessinger, E.; Bonnet, D.; So, C. W. E. β-Catenin mediates the establishment and drug resistance of MLL leukemic stem cells. *Cancer Cell* 2010, 18, 606-618.

Kim, J.-S.; Crooks, H.; Foxworth, A.; Waldman, T. Proof-of-principle: oncogenic β-catenin is a valid molecular target for the development of pharmacological inhibitors. *Mol. Cancer Ther.* 2002, 1, 1355-1359.

Ashihara, E.; Kawata, E.; Nakagawa, Y.; Shimazaski, C.; Kuroda, J.; Taniguchi, K.; Uchiyama, H.; Tanaka, R.; Yokota, A.; Takeuchi, M.; Kamitsuji, Y.; Inaba, T.; Taniwaki, M.; Kimura, S.; Maekawa, T. β-Catenin small interfering RNA successfully suppressed progression of multiple myeloma in a mouse model. *Clin. Cancer Res.* 2009, 15, 2731-2738.

Scholer-Dahirel, A.; Schlabach, M. R.; Loo, A.; Bagdasarian, L.; Meyer, R.; Guo, R.; Woolfenden, S.; Yu, K. K.; Markovits, J.; Killary, K.; Sonkin, D.; Yao, Y.-M.; Warmuth, M.; Sellers, W. R.; Schlegel, R.; Stegmeier, F.; Mosher, R. E.; McLaughlin, M. E. Maintenance of adenomatous polyposis coli (APC)-mutant colorectal cancer is dependent on Wnt/β-catenin signaling. *Proc. Natl. Acad. Sci. U.S.A.* 2011, 108, 17135-17140.

Graham, T. A.; Ferkey, D. M.; Mao, F.; Kimelman, D.; Xu, W. Tcf4 can specifically recognize β-catenin using alternative conformations. *Nat. Struct. Biol.* 2001, 8, 1048-1052.

Poy, F.; Lepourcelet, M.; Shivdasani, R. A.; Eck, M. J. Structure of a human Tcf4-β-catenin complex. *Nat. Struct. Biol.* 2001, 8, 1053-1057.

Sampietro, J.; Dahlberg, C. L.; Cho, U. S.; Hinds, T. R.; Kimelman, D.; Xu, W. Crystal structure of a β-catenin/Tcf/Tcf4 complex. *Mol. Cell* 2006, 24, 293-300.

Sun, J.; Weis, W. I. Biochemical and structural characterization of β-catenin interactions with nonphosphorylated and CK2-phosphorylated Lef-1. *J. Mol. Biol.* 2011, 405, 519-530.

Graham, T. A.; Weaver, C.; Mao, F.; Kimelman, D.; Xu, W. Crystal structure of a β-catenin/Tcf complex. *Cell* 2000, 103, 885-896.

Knapp, S.; Zamai, M.; Volpi, D.; Nardese, V.; Avanzi, N.; Breton, J.; Plyte, S.; Flocco, M.; Marconi, M.; Isacchi, A.; Caiolfa, V. R. Thermodynamics of the high-affinity interaction of TCF4 with β-catenin. *J. Mol. Biol.* 2001, 306, 1179-1189.

Yu, B.; Huang, Z.; Zhang, M.; Dillard, D. R.; Ji, H. Rational design of small-molecule inhibitors for β-catenin/T-cell factor protein-protein interactions by bioisostere replacement. *ACS Chem. Biol.* 2013, 8, 524-529.

von Kries, J. P.; Winbeck, G.; Asbrand, C.; Schwarz-Romond, T.; Sochnikova, N.; Dell'Oro, A.; Behrens, J.; Birchmeier, W. Hot spots in β-catenin for interactions with LEF-1, conductin and APC. *Nat. Struct. Biol.* 2000, 7, 800-807.

Gail, R.; Frank, R.; Wittinghofer, A. Systematic peptide array-based delineation of the differential β-catenin interaction with Tcf4, E-cadherin, and adenomatous polyposis coli. *J. Biol. Chem.* 2005, 280, 7107-7117.

Xing, Y.; Clements, W. K.; Kimelman, D.; Xu, W. Crystal structure of a β-catenin/axin complex suggests a mechanism for the β-catenin destruction complex. *Genes Dev.* 2003, 17, 2753-2764.

Huber, A. H.; Weis, W. I. The structure of the β-catenin/E-cadherin complex and the molecular basis of diverse ligand recognition by β-catenin. *Cell* 2001, 105, 391-402.

Spink, K. E.; Fridman, S. G.; Weis, W. I. Molecular mechanisms of β-catenin recognition by adenomatous polyposis coli revealed by the structure of an APC-β-catenin complex. *EMBO J.* 2001, 20, 6203-6212.

Ha, N.-C.; Tonozuka, T.; Stamos, J. L.; Choi, H.-J.; Weis, W. I. Mechanism of phosphorylation-dependent binding of APC to β-catenin and its role in β-catenin degradation. *Mol. Cell* 2004, 15, 511-521.

Xing, Y.; Clements, W. K.; Le Trong, I.; Hinds, T. R.; Stenkamp, R.; Kimelman, D.; Xu, W. Crystal structure of a β-catenin/APC complex reveals a critical role for APC phosphorylation in APC function. *Mol. Cell* 2004, 15, 523-533.

Orsulic, S.; Huber, O.; Aberle, H.; Arnold, S.; Kemler, R. E-cadherin binding prevents β-catenin nuclear localization and β-catenin/LEF-1-mediated transactivation. *J. Cell Sci.* 1999, 112, 1237-1245.

Choi, H.-J.; Huber, A. H.; Weis, W. I. Thermodynamics of β-catenin-ligand interactions: the roles of the N- and C-terminal tails in modulating binding affinity. *J. Biol. Chem.* 2006, 281, 1027-1038;

Sun, J.; Weis, W. I. Biochemical and structural characterization of β-catenin interactions with nonphosphorylated and CK2-phosphorylated Lef-1. *J. Mol. Biol.* 2011, 405, 519-530.

Choi, H.-J.; Gross, J. C.; Pokutta, S.; Weis, W. I. Interactions of plakoglobin and f-catenin with desmosomal cadherins: basis of selective exclusion of α- and β-catenin from desmosomes. *J. Biol. Chem.* 2009, 284, 31776-31788.

Tickenbrock, L.; Kodmeier, K.; Rehmann, H.; Herrmann, C.; Müller, O. Differences between the interaction of β-catenin with non-phosphorylated and single-mimicked phosphorylated 20-amino acid residue repeats of the APC protein. *J. Mol. Biol.* 2003, 327, 359-367.

Liu, J.; Xing, Y.; Hinds, T. R.; Zheng, J.; Xu, W. The third 20 amino acid repeat is the tightest binding site of APC for β-catenin. *J. Mol. Biol.* 2006, 360, 133-144.

Lepourcelet, M.; Chen, Y.-N. P.; France, D. S.; Wang, H.; Crews, P.; Petersen, F.; Bruseo, C.; Wood, A. W.; Shivdasani, R. A. Small-molecule antagonists of the oncogenic Tcf/β-catenin protein complex. *Cancer Cell* 2004, 5, 91-102.

Halbedl, S.; Kratzer, M.-C.; Rahm, K.; Crosta, N.; Masters, K.-S.; Zippert, J.; Bräse, S.; Gradl, D. Synthesis of novel inhibitors blocking Wnt signaling downstream of β-catenin. *FEBS Lett.* 2013, 587, 522-527.

Baell, J.; Walters, M. A. Chemistry: Chemical con artists foil drug discovery. *Nature* 2014, 513, 481-483.

Trosset, J.-Y.; Dalvit, C.; Knapp, S.; Fasolini, M.; Veronesi, M.; Mantegani, S.; Gianellini, L. M.; Catana, C.; Sundström, M.; Stouten, P. F. W.; Moll, J. K. Inhibition of protein-protein interactions: the discovery of druglike β-catenin inhibitors by combining virtual and biophysical screening. *Proteins* 2006, 64, 60-67.

Gonsalves, F. C.; Klein, K.; Carson, B. B.; Katz, S.; Ekas, L. A.; Evans, S.; Nagourney, R.; Cardozo, T.; Brown, A. M.; DasGupta, R. An RNAi-based chemical genetic screen identifies three small-molecule inhibitors of the Wnt/wingless signaling pathway. *Proc. Natl. Acad. Sci. U.S.A.* 2011, 108, 5954-5963.

Baell, J. B. Observations on screening-based research and some concerning trends in the literature. *Future Med. Chem.* 2010, 2, 1529-1546.

Tomašić, T.; Mašič, L. P. Rhodanine as a privileged scaffold in drug discovery. *Curr. Med. Chem.* 2009, 16, 1596-1629.

Lee, E.; Mada, A.; David, G.; Garabedian, M. J.; DasGupta, R.; Logan, S. K. Inhibition of androgen receptor and β-catenin activity in prostate cancer. *Proc. Natl. Acad. Sci. U.S.A.* 2013, 110, 15710-15715.

Tian, W.; Han, X.; Yan, M.; Xu, Y.; Duggineni, S.; Lin, N.; Luo, G.; Li, Y. M.; Han, X.; Huang, Z.; An, J. Structure-based discovery of a novel inhibitor targeting the β-catenin/Tcf4 interaction. *Biochemistry* 2012, 51, 724-731.

Grossmann, T. N.; Yeh, J. T.-H.; Bowman, B. R.; Chu, Q.; Moellering, R. E.; Verdine, G. L. Inhibition of oncogenic Wnt signaling through direct targeting of β-catenin. *Proc. Natl. Acad. Sci. U.S.A.* 2012, 109, 17942-19747.

Huang, Z.; Zhang, M.; Burton, S. D.; Katsakhyan, L. N.; Ji. H. Targeting the Tcf4 $G^{13}ANDE^{17}$ binding site to selectivity disrupt β-catenin/T-cell factor protein-protein interactions. *ACS Chem. Biol.* 2014, 9, 193-201.

Zhang, M.; Huang, Z.; Yu, B.; Ji, H. New homogeneous high-throughput assays for inhibitors of β-catenin/Tcf protein-protein interactions *Anal. Biochem.* 2012, 424, 57-63.

Mysinger, M. M.; Weiss, D. R.; Ziarek, J. J.; Gravel, S.; Doak, A. K.; Karpiak, J.; Heveker, N.; Shoichet, B. K.; Volkman, B. F. Structure-based ligand discovery for the protein-protein interface of chemokine receptor CXCR4. *Proc. Natl. Acad. Sci. U.S.A.* 2012, 109, 5517-5522.

Roubinek, F.; Bydžovský, V.; Buděšinský, Z. Substituted 5- and 6-quinoxalinecarboxylic acids and their tuberculostatic activity. *Collect. Czech. Chem. Commun.* 1984, 49, 285-294.

Zhang, M.; Catrow, J. L.; Ji, H. High-throughput selectivity assays for small-molecule inhibitors of β-catenin/T-cell factor protein-protein interactions. *ACS Med. Chem. Lett.* 2013, 4, 306-311.

Guedat, P.; Jacq, X.; Colland, F.; Daviet, L.; Formstecher, E.; Rain, J.-C.; Colombo, M. Preparation of tetracyclic compounds as cysteine proteases inhibitors. U.S. Pat. No. 7,875,613, Jan. 25, 2011.

Gaillard, P.; Quattropani, A.; Pomel, V.; Rueckle, T.; Klicic, J.; Church, D. Preparation of pyrazine derivatives, particularly N-[3-(oxyphenylamino)quinoxalin-2-yl]sulfonamides, as PI3K inhibitors. U.S. Pat. No. 8,071,597, Dec. 6, 2011.

Korinek, V.; Barker, N.; Morin, P. J.; van Wichen, D.; de Weger, R.; Kinzler, K. W.; Vogelstein, B.; Clevers, H. Constitutive transcriptional activation by a β-catenin-Tcf complex in APC$^{-/-}$ colon carcinoma. *Science* 1997, 275, 1784-1787.

Ilyas, M.; Tomlinson, I. P. M.; Rowan, A.; Pignatelli, M.; Bodmer, W. F. β-Catenin mutations in cell lines established from human colorectal cancers. *Proc. Natl. Acad. Sci. U.S.A.* 1997, 94, 10330-10334.

Sparks, A. B.; Morin, P. J.; Vogelstein, B.; Kinzler, K. W. Mutational analysis of the APC/β-catenin/Tcf pathway in colorectal cancer. *Cancer Res.* 1998, 58, 1130-1134.

Leung, J. Y.; Kolligs, F. T.; Wu, R.; Zhai, Y.; Kuick, R.; Hanash, S.; Cho, K. R.; Fearon, E. R. Activation of AXIN2 expression by β-catenin-T cell factor. A feedback repressor pathway regulating Wnt signaling. *J. Biol. Chem.* 2002, 277, 21657-21665.

Jadhav, A.; Ferreira, R. S.; Klumpp, C.; Mott, B. T.; Austin, C. P.; Inglese, J.; Thomas, C. J.; Maloney, D. J.; Shoichet, B. K.; Simeonov A. Quantitative analyses of aggregation, autofluorescence, and reactivity artifacts in a screen for inhibitors of a thiol protease. *J. Med. Chem.* 2010, 53, 37-51.

Che, J.; King, F. J.; Zhou, B.; Zhou, Y. Chemical and biological properties of frequent screening hits. *J. Chem. Inf. Model.* 2012, 52, 913-926.

Yu, B.; Reynisson, J. Bond stability of the "undesirable" heteroatom-heteroatom molecular moieties for high-throughput screening libraries. *Eur. J. Med. Chem.* 2011, 46, 5833-5837.

Metz, J. T.; Huth, J. R.; Hajduk, P. J. Enhancement of chemical rules for predicting compound reactivity towards protein thiol groups. *J. Comput.-Aided Mol. Des.* 2007, 21, 139-144.

Huth, J. R.; Song, D.; Mendoza, R. R.; Black-Schaefer, C. L.; Mack, J. C.; Dorwin, S. A.; Ladror, U. S.; Severin, J. M.; Walter, K. A.; Bartley, D. M.; Hajduk, P. J. Toxicological evaluation of thiol-reactive compounds identified using a La assay to detect reactive molecules by nuclear magnetic resonance. *Chem. Res. Toxicol.* 2007, 20, 1752-1759.

Dahlin, J. L.; Nissink, J. W. M.; Strasser, J. M.; Francis, S.; Higgins, L.; Zhou, H.; Zhang, Z.; Walters, M. A. PAINS in the assay: chemical mechanisms of assay interference and promiscuous enzymatic inhibition observed during a sulfhydryl-scavenging HTS. *J. Med. Chem.* 2015, 58, 2091-2113.

Takabatake, T.; Miyazawa, T.; Hasegawa, M.; Foote, C. S. Reaction of 4,7-dimethylbenzofurazan with singlet oxygen. *Tetrahedron Lett.* 2001, 42, 987-989.

Okabe, K.; Wada, R.; Ohno, K.-i.; Uchiyama, S.; Santa, T.; Imai, K. Development of hydrophilic fluorogenic derivatization reagents for thiols: 4-(N-acetylaminosulfonyl)-7-fluoro-2, 1,3-benzoxadiazole and 4-(N-trichloroacetylaminosulfonyl)-7-fluoro-2,1,3-benzoxadiazole. *J. Chromatogr. A.* 2002, 982, 111-118.

Řeha, D.; Kabeláč, M.; Ryjáček, F.; Šponer, J.; Šponer, J. E.; Elstner, M.; Suhai, S.; Hobza, P. Intercalators. 1. Nature of stacking interactions between intercalators (ethidium, daunomycin, ellipticine, and 4',6-diaminide-2-phenylindole) and DNA base pairs. Ab initio quantum chemical, density functional theory, and empirical potential study. *J. Am. Chem. Soc.* 2002, 124, 3366-3376.

Reynisson, J.; Schuster, G. B.; Howerton, S. B.; Williams, L. D.; Barnett, R. N.; Cleveland, C. L.; Landman, U.; Harrit, N.; Chaires, J. B. Intercalation of trioxatriangulenium ion in DNA: binding, electron transfer, x-ray crystallography, and electronic structure. *J. Am. Chem. Soc.* 2003, 125, 2072-2083.

Ichikawa, T.; Kato T.; Takenishi T. New synthesis of adenine and 4-aminoimidazole-5-carboxamide. *J. Heterocyclic Chem.* 1965, 2, 253-255.

Trott, O.; Olson, A. J. AutoDock Vina: improving the speed and accuracy of docking with a new scoring function, efficient optimization, and multithreading. *J. Comput. Chem.* 2010, 31, 455-461.

Friesner, R. A.; Banks, J. L.; Murphy, R. B.; Halgren, T. A.; Klicic, J. J.; Mainz, D. T.; Repasky, M. P.; Knoll, E. H.; Shelley, M.; Perry, J. K.; Shaw, D. E.; Francis, P.; Shenkin, P. S. Glide: a new approach for rapid, accurate docking and scoring. 1. Method and assessment of docking accuracy. *J. Med. Chem.* 2004, 47, 1739-1749.

Morris, G. M.; Huey, R.; Lindstrom, W.; Sanner, M. F.; Belew, R. K.; Goodsell, D. S.; Olson, A. J. AutoDock4 and AutoDockTools4: Automated docking with selective receptor flexibility. *J. Comput. Chem.* 2009, 30, 2785-2791.

Helissey, P.; Desbène-Finck, S.; Giorgi-Renault, S. Alkylation of 5- and 6-methylindolo[2,3-b]quinoxalines: revised structures of the N,N'-dimethylated salts. *Eur. J. Org. Chem.* 2005, 410-415.

Thomas, K. R. J.; Tyagi, P. Synthesis, spectra, and theoretical investigations of the triarylamines based on 6H-indolo [2,3-b]quinoxaline. *J. Org. Chem.* 2010, 75, 8100-8111.

Ramström, O.; Lehn, J.-M. Drug discovery by dynamic combinatorial libraries. *Nat. Rev. Drug. Discov.* 2002, 1, 26-36.

Smith, M. C.; Gestwicki, J. E. Features of protein-protein interactions that translate into potent inhibitors: topology, surface area and affinity. *Expert Rev. Mol. Med.* 2012, 14, e16.

Nikolovska-Coleska, Z.; Wang, R.; Fang, X.; Pan, H.; Tomita, Y.; Li, P.; Roller, P. P.; Krajewski, K.; Saito, N. G.; Stuckey, J. A.; Wang, S. Development and optimization of a binding assay for the XIAP BIR3 domain using fluorescence polarization. *Anal. Biochem.* 2004, 332, 261-273.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

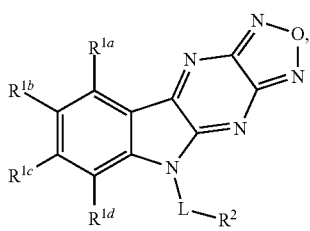

wherein each of $R^{1a}$, $R^{1b}$, $R^{1c}$, and $R^{1d}$ is independently hydrogen, halogen, —CN, C1-C4 alkyl, or C1-C4 haloalkyl;

wherein L is $(CH_2)_n$ or a moiety having a structure represented by a formula:

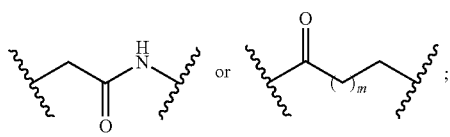

wherein m is an integer with a value of 0 or 1;
wherein n is an integer with a value of 0, 1, 2, 3, or 4; and
wherein $R^2$ is —CN or a moiety having a structure represented by a formula:

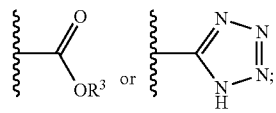

wherein $R^3$ is hydrogen or C1-C4 alkyl;
or a pharmaceutically acceptable salt thereof.

2. The compound of claim 1, wherein each of $R^{1a}$, $R^{1b}$, $R^{1c}$, and $R^{1d}$ is hydrogen.

3. The compound of claim 1, wherein each of $R^{1a}$, $R^{1b}$, and $R^{1d}$ is hydrogen; and wherein $R^{1c}$ is hydrogen, —F, —Cl, —Br, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$.

4. The compound of claim 1, wherein each of $R^{1a}$, $R^{1c}$, and $R^{1d}$ is hydrogen; and wherein $R^{1b}$ is hydrogen, —F, —Cl, —Br, —CN, methyl, —CH$_2$F, —CH$_2$Cl, —CH$_2$Br, —CHF$_2$, —CF$_3$, —CHCl$_2$, —CCl$_3$, —CHBr$_2$, or —CBr$_3$.

5. The compound of claim 1, wherein each of $R^{1a}$, $R^{1b}$, and $R^{1d}$ is hydrogen; and wherein $R^{1c}$ is —F, —Cl, —Br, —CN, or methyl.

6. The compound of claim 1, wherein each of $R^{1a}$, $R^{1c}$, and $R^{1d}$ is hydrogen; and wherein $R^{1b}$ is —F, —Cl, —Br, —CN, or methyl.

7. The compound of claim 1, wherein L is $(CH_2)_n$; and wherein n is an integer with a value of 0, 1, 2, 3, or 4.

8. The compound of claim 1, wherein L is a moiety having a structure represented by a formula:

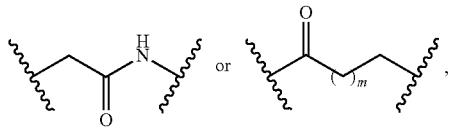

wherein m is an integer with a value of 0 or 1.

9. The compound of claim 1, wherein L is a moiety having a structure represented by a formula:

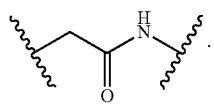 [SMILES: *CC(=O)N*]

10. The compound of claim 1, wherein L is a moiety having a structure represented by a formula:

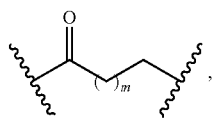

wherein m is an integer with a value of 0 or 1.

11. The compound of claim 1, wherein $R^2$ is —CN.

12. The compound of claim 1, wherein $R^2$ is a moiety having a structure represented by a formula:

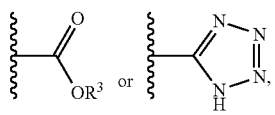

wherein $R^3$ is hydrogen or C1-C4 alkyl.

13. The compound of claim 1, wherein $R^2$ is a moiety having a structure represented by a formula:

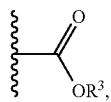

wherein $R^3$ is hydrogen, methyl, ethyl, propyl, or isopropyl.

14. The compound of claim 1, wherein $R^2$ is a moiety having a structure represented by a formula:

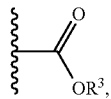

wherein $R^3$ is hydrogen.

15. The compound of claim 1, wherein $R^2$ is a moiety having a structure represented by a formula:

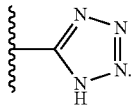

16. The compound of claim 1, wherein $R^3$ is hydrogen, methyl, ethyl, propyl, or isopropyl.

17. The compound of claim 1, having a structure represented by a formula:

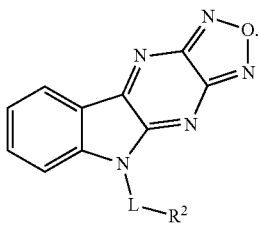

18. A method for the treatment of a disorder of uncontrolled cellular proliferation associated with a β-catenin/TCF dysfunction in a mammal comprising the step of administering to the mammal an effective amount of at least one compound having a structure represented by a formula:

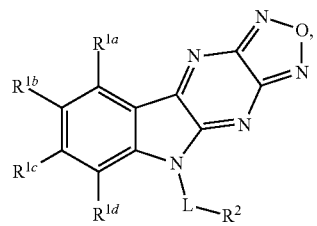

wherein each of $R^{1a}$, $R^{1b}$, $R^{1c}$, and $R^{1d}$ is independently hydrogen, halogen, —CN, C1-C4 alkyl, or C1-C4 haloalkyl;

wherein L is $(CH_2)_n$ or a moiety having a structure represented by a formula:

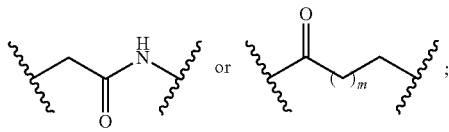

wherein m is an integer with a value of 0 or 1;

wherein n is an integer with a value of 0, 1, 2, 3, or 4; and wherein $R^2$ is —CN or a moiety having a structure represented by a formula:

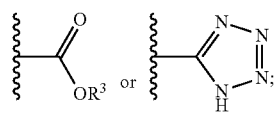

wherein $R^3$ is hydrogen or C1-C4 alkyl;

or a pharmaceutically acceptable salt thereof.

19. The method of claim 18, wherein the mammal is a human.

20. The method of claim 18, wherein the disorder is cancer.

21. The method of claim 18, wherein the disorder is fibrosis.

* * * * *

```
                        SEQUENCE LISTING

<160> NUMBER OF SEQ ID NOS: 4

<210> SEQ ID NO 1
<211> LENGTH: 46
<212> TYPE: PRT
<213> ORGANISM: Artificial Sequence
<220> FEATURE:
<223> OTHER INFORMATION: Synthetic Construct

<400> SEQUENCE: 1

Gly Gly Gly Asp Asp Leu Gly Ala Asn Asp Glu Leu Ile Ser Phe Lys
1               5                   10                  15

Asp Glu Gly Glu Gln Glu Glu Lys Ser Ser Glu Asn Ser Ser Ala Glu
            20                  25                  30

Arg Asp Leu Ala Asp Val Lys Ser Ser Leu Val Asn Glu Lys
        35                  40                  45

<210> SEQ ID NO 2
<211> LENGTH: 46
<212> TYPE: PRT
<213> ORGANISM: Artificial Sequence
<220> FEATURE:
<223> OTHER INFORMATION: Synthetic Construct

<400> SEQUENCE: 2

Gly Gly Gly Asp Asp Leu Gly Ala Asn Asp Glu Leu Ile Ser Phe Lys
1               5                   10                  15

Asp Glu Gly Glu Gln Glu Glu Lys Ser Ser Glu Asn Ser Ser Ala Glu
            20                  25                  30

Arg Asp Leu Ala Asp Val Lys Ser Ser Leu Val Asn Glu Lys
        35                  40                  45

<210> SEQ ID NO 3
<211> LENGTH: 55
<212> TYPE: PRT
<213> ORGANISM: Artificial Sequence
<220> FEATURE:
<223> OTHER INFORMATION: Synthetic Construct

<400> SEQUENCE: 3

Asp Thr Asp Pro Thr Ala Pro Pro Tyr Asp Ser Leu Leu Val Phe Asp
1               5                   10                  15

Tyr Glu Gly Ser Gly Ser Glu Ala Ala Ser Leu Ser Ser Leu Asn Ser
            20                  25                  30

Ser Glu Ser Asp Lys Asp Gln Asp Tyr Asp Tyr Leu Asn Glu Trp Gly
        35                  40                  45

Asn Arg Phe Lys Lys Leu Ala
    50                  55

<210> SEQ ID NO 4
<211> LENGTH: 43
<212> TYPE: PRT
<213> ORGANISM: Artificial Sequence
<220> FEATURE:
<223> OTHER INFORMATION: Synthetic Construct
```

```
<400> SEQUENCE: 4

Gln Arg Val Gln Val Leu Pro Asp Ala Asp Thr Leu Leu His Phe Ala
1               5                   10                  15

Thr Glu Ser Thr Pro Asp Gly Phe Ser Cys Ser Ser Ser Leu Ser Ala
            20                  25                  30

Leu Ser Leu Asp Glu Pro Phe Ile Gln Lys Asp
            35                  40
```